US011337932B2

(12) United States Patent
Mohr et al.

(10) Patent No.: US 11,337,932 B2
(45) Date of Patent: May 24, 2022

(54) TRANSDERMAL THERAPEUTIC SYSTEM CONTAINING ASENAPINE AND POLYSILOXANE OR POLYISOBUTYLENE

(71) Applicant: LTS LOHMANN Therapie-Systeme AG, Andernach (DE)

(72) Inventors: Patrick Mohr, Bad Breisig (DE); René Rietscher, Neuwied (DE); René Eifler, Koblenz (DE); Olga Bourquain, Dürrholz (DE)

(73) Assignee: LTS LOHMANN Therapie-Systeme AG, Andernach (DE)

( * ) Notice: Subject to any disclaimer, the term of this patent is extended or adjusted under 35 U.S.C. 154(b) by 73 days.

(21) Appl. No.: 16/470,322

(22) PCT Filed: Dec. 19, 2017

(86) PCT No.: PCT/EP2017/083640
§ 371 (c)(1),
(2) Date: Jun. 17, 2019

(87) PCT Pub. No.: WO2018/115010
PCT Pub. Date: Jun. 28, 2018

(65) Prior Publication Data
US 2020/0085759 A1 Mar. 19, 2020

(30) Foreign Application Priority Data

Dec. 20, 2016 (EP) .................................. 16205502
Jun. 28, 2017 (EP) .................................. 17178268

(51) Int. Cl.
A61K 9/70 (2006.01)
A61K 31/407 (2006.01)

(52) U.S. Cl.
CPC .......... A61K 9/7069 (2013.01); A61K 9/7053 (2013.01); A61K 31/407 (2013.01)

(58) Field of Classification Search
None
See application file for complete search history.

(56) References Cited

U.S. PATENT DOCUMENTS

| 4,145,434 | A | 3/1979 | Van Der Burg |
| 4,158,059 | A | 6/1979 | Van Der Burg |
| 5,112,842 | A | 5/1992 | Zierenberg et al. |
| 5,446,070 | A | 8/1995 | Mantelle |
| 5,656,286 | A | 8/1997 | Miranda et al. |
| 5,763,476 | A | 6/1998 | Delbressine et al. |
| 5,830,497 | A | 11/1998 | Yamanaka et al. |
| 6,190,690 | B1 | 2/2001 | Park et al. |
| 6,235,306 | B1 | 5/2001 | Miranda et al. |
| 6,620,429 | B1 | 9/2003 | Mueller |
| 6,638,528 | B1 | 10/2003 | Kanios |
| 6,669,953 | B1 | 12/2003 | Kamiyama |
| 6,797,280 | B1 | 9/2004 | Kitazono et al. |
| 6,964,962 | B2 | 11/2005 | Wong et al. |
| 7,641,703 | B2 | 1/2010 | Guerin et al. |
| 7,650,848 | B2 | 1/2010 | Brennan et al. |
| 7,744,918 | B2 | 6/2010 | Yamaguchi et al. |
| 7,875,729 | B2 | 1/2011 | Zhu et al. |
| 7,884,096 | B2 | 2/2011 | Buntinx |
| 7,956,202 | B2 | 6/2011 | Kemperman et al. |
| 7,964,739 | B2 | 6/2011 | Kemperman |
| 7,973,043 | B2 | 7/2011 | Migaly |
| 7,988,991 | B2 | 8/2011 | Tateishi et al. |
| 8,022,228 | B2 | 9/2011 | Heeres |
| 8,173,637 | B2 | 5/2012 | Liu et al. |
| 8,202,525 | B2 | 6/2012 | Crain et al. |
| 8,227,623 | B2 | 7/2012 | Kemperman et al. |
| 8,288,564 | B2 | 10/2012 | Wang et al. |
| 8,304,431 | B2 | 11/2012 | Buntinx |
| 8,309,120 | B2 | 11/2012 | Koch et al. |
| 8,318,813 | B2 | 11/2012 | Sanfilippo |
| 8,372,414 | B2 | 2/2013 | Crain et al. |
| 8,409,609 | B2 | 4/2013 | Inosaka et al. |
| 8,420,117 | B2 | 4/2013 | Chono et al. |
| 8,426,610 | B2 | 4/2013 | Kemperman et al. |
| 8,431,552 | B2 | 4/2013 | Chen |

(Continued)

FOREIGN PATENT DOCUMENTS

CN 1121854 C 9/2003
CN 102746209 A 10/2012
(Continued)

OTHER PUBLICATIONS

Co-pending, U.S. Appl. No. 17/195,267, inventors Mohr, P., et al., filed Mar. 8, 2021 (Not yet Published).

(Continued)

Primary Examiner — Nannette Holloman
(74) Attorney, Agent, or Firm — Sterne, Kessler, Goldstein & Fox P.L.L.C.

(57) ABSTRACT

The present invention relates to a transdermal therapeutic system (TTS) for the transdermal administration of asenapine comprising a self-adhesive layer structure comprising a therapeutically effective amount of asenapine, said self-adhesive layer structure comprising: A) a backing layer; B) an asenapine-containing layer comprising: 1. asenapine in the form of the free base; and 2. a polymer selected from the group consisting of polysiloxanes and polyisobutylenes in an amount of more than 50% by weight based on the total weight of the asenapine-containing layer; and C) optionally an additional skin contact layer.

19 Claims, 8 Drawing Sheets

(56) References Cited

U.S. PATENT DOCUMENTS

| | | |
|---|---|---|
| 8,512,742 B2 | 8/2013 | Amano et al. |
| 8,580,281 B2 | 11/2013 | Morimoto et al. |
| 8,580,972 B2 | 11/2013 | Bosch i Llado et al. |
| 8,591,941 B2 | 11/2013 | Kanios et al. |
| 8,614,274 B2 | 12/2013 | Jackson et al. |
| 8,617,577 B2 | 12/2013 | Crain et al. |
| 8,624,052 B2 | 1/2014 | Johnson et al. |
| 8,632,802 B2 | 1/2014 | Kanios |
| 8,652,776 B2 | 2/2014 | Laved et al. |
| 8,653,280 B2 | 2/2014 | Dalmases et al. |
| 8,658,687 B2 | 2/2014 | Faassen et al. |
| 8,703,175 B2 | 4/2014 | Kanios et al. |
| 8,741,319 B2 | 6/2014 | Crain et al. |
| 8,779,161 B2 | 7/2014 | Katkam et al. |
| 8,846,093 B2 | 9/2014 | Govil et al. |
| 8,933,114 B2 | 1/2015 | Ventimiglia et al. |
| 8,945,063 B2 | 2/2015 | Wotton et al. |
| 8,986,677 B2 | 3/2015 | Altschul et al. |
| 9,011,910 B2 | 4/2015 | Schwarz |
| 9,017,737 B2 | 4/2015 | Kikuchi et al. |
| 9,050,348 B2 | 6/2015 | Kydonieus et al. |
| 9,073,890 B2 | 7/2015 | Suzuki et al. |
| 9,095,516 B2 | 8/2015 | Middelbeek et al. |
| 9,119,794 B2 | 9/2015 | Middelbeek et al. |
| 9,145,421 B2 | 9/2015 | Aryan et al. |
| 9,169,262 B2 | 10/2015 | Blatter et al. |
| 9,180,191 B2 | 11/2015 | Sheehan et al. |
| 9,198,877 B2 | 12/2015 | Jackson et al. |
| 9,205,060 B2 | 12/2015 | Kamakura et al. |
| 9,226,902 B2 | 1/2016 | Tang |
| 9,267,151 B2 | 2/2016 | Guerrero et al. |
| 9,295,726 B2 | 3/2016 | Kulakofsky et al. |
| 9,303,036 B2 | 4/2016 | Blatter et al. |
| 9,328,387 B2 | 5/2016 | Laved et al. |
| 9,370,495 B2 | 6/2016 | Toshimitsu et al. |
| 9,393,367 B2 | 7/2016 | Wotton et al. |
| 9,421,178 B2 | 8/2016 | Fogel et al. |
| 9,427,420 B2 | 8/2016 | Fogel et al. |
| 9,447,066 B2 | 9/2016 | Okumura et al. |
| 9,447,109 B2 | 9/2016 | Frigoli et al. |
| 9,457,014 B2 | 10/2016 | Lawton et al. |
| 9,457,018 B2 | 10/2016 | Scheel-Krüger et al. |
| 9,486,453 B2 | 11/2016 | Javitt |
| 9,499,816 B2 | 11/2016 | Mann |
| 9,500,642 B2 | 11/2016 | Blackman et al. |
| 9,505,771 B2 | 11/2016 | Bertran et al. |
| 9,511,051 B2 | 12/2016 | Suzuki et al. |
| 9,526,718 B2 | 12/2016 | Lee et al. |
| 9,533,994 B2 | 1/2017 | Solà Carandell et al. |
| 9,844,515 B2 | 12/2017 | Fleschhut et al. |
| 10,071,090 B2 | 9/2018 | Stinchcomb et al. |
| 10,898,449 B2 | 1/2021 | Mohr et al. |
| 10,980,753 B2 | 4/2021 | Mohr et al. |
| 11,033,512 B2 | 6/2021 | Mohr et al. |
| 2003/0109546 A1 | 6/2003 | Fenton |
| 2003/0228354 A1 | 12/2003 | Muraoka et al. |
| 2004/0033254 A1 | 2/2004 | Song et al. |
| 2004/0202704 A1 | 10/2004 | Sharma et al. |
| 2005/0004106 A1 | 1/2005 | Romano |
| 2005/0171086 A1 | 8/2005 | Brodney et al. |
| 2005/0209250 A1 | 9/2005 | Romano |
| 2005/0215571 A1 | 9/2005 | Romano |
| 2005/0245539 A1 | 11/2005 | Mendla et al. |
| 2005/0256112 A1 | 11/2005 | Brodney et al. |
| 2006/0019969 A1 | 1/2006 | Baeyens |
| 2006/0084692 A1 | 4/2006 | Erik et al. |
| 2006/0128688 A1 | 6/2006 | Tonnaer |
| 2006/0150989 A1 | 7/2006 | Migaly |
| 2006/0177493 A1 | 8/2006 | Altenschopfer et al. |
| 2006/0204486 A1 | 9/2006 | Pyke et al. |
| 2006/0229299 A1 | 10/2006 | Bruinvels |
| 2006/0286160 A1 | 12/2006 | Satoda et al. |
| 2006/0292210 A1 | 12/2006 | Inosaka et al. |
| 2007/0015763 A1 | 1/2007 | Romano |
| 2007/0148218 A1 | 6/2007 | Gordon |
| 2007/0191350 A1 | 8/2007 | Field et al. |
| 2007/0203119 A1 | 8/2007 | Danjou et al. |
| 2007/0259952 A1 | 11/2007 | Svensson |
| 2008/0020028 A1 | 1/2008 | Shevchuk et al. |
| 2008/0045512 A1 | 2/2008 | Duplantier et al. |
| 2008/0090892 A1 | 4/2008 | Casteel et al. |
| 2008/0103155 A1 | 5/2008 | Mendla et al. |
| 2008/0131490 A1 | 6/2008 | Hanatani et al. |
| 2008/0138388 A1 | 6/2008 | Aida et al. |
| 2008/0226697 A1 | 9/2008 | Yamaguchi et al. |
| 2008/0226698 A1 | 9/2008 | Tang et al. |
| 2008/0306133 A1 | 12/2008 | Van Der Sterren et al. |
| 2009/0004255 A1 | 1/2009 | Uchida et al. |
| 2009/0042950 A1 | 2/2009 | Pandya |
| 2009/0075974 A1 | 3/2009 | Yamaguchi et al. |
| 2009/0111837 A1 | 4/2009 | Cox et al. |
| 2009/0148504 A1 | 6/2009 | Kamiyama et al. |
| 2009/0169605 A1 | 7/2009 | Maeda et al. |
| 2009/0209608 A1 | 8/2009 | Czarnik |
| 2010/0004259 A1 | 1/2010 | Liu et al. |
| 2010/0178323 A1 | 7/2010 | Kydonieus et al. |
| 2010/0234288 A1 | 9/2010 | Jain et al. |
| 2010/0297181 A1 | 11/2010 | Hanada et al. |
| 2011/0105519 A1 | 5/2011 | Mendla et al. |
| 2011/0106006 A1 | 5/2011 | Martin et al. |
| 2011/0166194 A1 | 7/2011 | Blumberg et al. |
| 2011/0178068 A1 | 7/2011 | Almarsson et al. |
| 2011/0262442 A1 | 10/2011 | Hamilton et al. |
| 2011/0269777 A1 | 11/2011 | Bachurin et al. |
| 2011/0306596 A1 | 12/2011 | Rao et al. |
| 2012/0010242 A1 | 1/2012 | Buntinx |
| 2012/0122793 A1 | 5/2012 | Johnson et al. |
| 2012/0157420 A1 | 6/2012 | Schneider |
| 2012/0201804 A1 | 8/2012 | Williams et al. |
| 2012/0237561 A1 | 9/2012 | Faassen et al. |
| 2012/0315318 A1 | 12/2012 | Toshimitsu et al. |
| 2013/0053357 A1 | 2/2013 | Kuma et al. |
| 2013/0071412 A1 | 3/2013 | Leighton et al. |
| 2013/0143867 A1 | 6/2013 | Fogel et al. |
| 2013/0203766 A1 | 8/2013 | Mendla et al. |
| 2013/0217681 A1 | 8/2013 | Weizman et al. |
| 2013/0224110 A1 | 8/2013 | Bynoe |
| 2013/0245004 A1 | 9/2013 | Fogel et al. |
| 2013/0245253 A1 | 9/2013 | Marx et al. |
| 2013/0274466 A1 | 10/2013 | Gorin et al. |
| 2013/0344125 A1 | 12/2013 | Govender et al. |
| 2014/0018348 A1 | 1/2014 | Javitt |
| 2014/0037710 A1 | 2/2014 | Hashimoto et al. |
| 2014/0080911 A1 | 3/2014 | Stefanelli et al. |
| 2014/0121202 A1 | 5/2014 | Johnson et al. |
| 2014/0163083 A1 | 6/2014 | Blatter et al. |
| 2014/0206667 A1 | 7/2014 | Gallagher |
| 2014/0221742 A1 | 8/2014 | Bandy et al. |
| 2014/0221942 A1 | 8/2014 | Scasso et al. |
| 2014/0271866 A1 | 9/2014 | Ryoo |
| 2014/0271923 A1 | 9/2014 | Reid |
| 2014/0276478 A1 | 9/2014 | Liao et al. |
| 2014/0276479 A1 | 9/2014 | Nguyen et al. |
| 2014/0287529 A1 | 9/2014 | Leider |
| 2014/0315886 A1 | 10/2014 | Suzuki et al. |
| 2014/0336391 A1 | 11/2014 | Sharma et al. |
| 2014/0350064 A1 | 11/2014 | Chen |
| 2014/0350081 A1 | 11/2014 | Hill et al. |
| 2015/0037335 A1 | 2/2015 | Westbrook |
| 2015/0099015 A1 | 4/2015 | Tsai |
| 2015/0099741 A1 | 4/2015 | Li et al. |
| 2015/0111834 A1 | 4/2015 | Cheng et al. |
| 2015/0141274 A1 | 5/2015 | Friedman et al. |
| 2015/0202183 A1 | 7/2015 | Suzuki et al. |
| 2015/0224120 A1 | 8/2015 | Clelland et al. |
| 2015/0231154 A1 | 8/2015 | Theobald et al. |
| 2015/0231250 A1 | 8/2015 | Sonobe et al. |
| 2015/0250716 A1 | 9/2015 | Watkins |
| 2015/0272946 A1 | 10/2015 | Sato et al. |
| 2015/0292014 A1 | 10/2015 | Zhu et al. |
| 2015/0320739 A1 | 11/2015 | Mendla et al. |
| 2015/0328163 A1 | 11/2015 | Gujjar et al. |
| 2015/0329497 A1 | 11/2015 | Pinkerton et al. |
| 2015/0343144 A1 | 12/2015 | Altschul et al. |

(56) References Cited

U.S. PATENT DOCUMENTS

| | | |
|---|---|---|
| 2015/0359566 A1 | 12/2015 | Sillender |
| 2016/0022571 A1 | 1/2016 | Schwarz et al. |
| 2016/0024011 A1 | 1/2016 | Zeid et al. |
| 2016/0030362 A1 | 2/2016 | Liao et al. |
| 2016/0101075 A1 | 4/2016 | Fogel et al. |
| 2016/0199313 A1 | 7/2016 | LeDonne et al. |
| 2016/0235677 A1 | 8/2016 | Hoerr et al. |
| 2016/0303102 A1 | 10/2016 | Albayrak |
| 2016/0310502 A1 | 10/2016 | Vanover et al. |
| 2016/0317465 A1 | 11/2016 | Shinoda et al. |
| 2017/0007537 A1 | 1/2017 | Reddy et al. |
| 2017/0079932 A1 | 3/2017 | Emgenbroich et al. |
| 2017/0202830 A1 | 7/2017 | Stinchcomb et al. |
| 2018/0028461 A1 | 2/2018 | Singh et al. |
| 2018/0028464 A1 | 2/2018 | Komoda et al. |
| 2018/0193283 A1 | 7/2018 | Mohr et al. |
| 2018/0207108 A1 | 7/2018 | Sonobe et al. |
| 2019/0336454 A1 | 11/2019 | Mohr et al. |
| 2020/0179298 A1 | 6/2020 | Mohr et al. |
| 2020/0188317 A1 | 6/2020 | Mohr et al. |

FOREIGN PATENT DOCUMENTS

| | | |
|---|---|---|
| CN | 102858372 A | 1/2013 |
| CN | 102952144 A | 3/2013 |
| CN | 102976929 A | 3/2013 |
| CN | 102976998 A | 3/2013 |
| CN | 103113379 A | 5/2013 |
| CN | 103120688 A | 5/2013 |
| CN | 101851242 B | 7/2013 |
| CN | 103183680 A | 7/2013 |
| CN | 102229613 B | 8/2013 |
| CN | 102657635 B | 8/2013 |
| CN | 103254202 A | 8/2013 |
| CN | 103760258 A | 4/2014 |
| CN | 103760280 A | 4/2014 |
| CN | 103772400 A | 5/2014 |
| CN | 103772401 A | 5/2014 |
| CN | 103772402 A | 5/2014 |
| CN | 103864802 A | 6/2014 |
| CN | 103893139 A | 7/2014 |
| CN | 103083284 B | 8/2014 |
| CN | 103099799 B | 8/2014 |
| CN | 103965206 A | 8/2014 |
| CN | 104000800 A | 8/2014 |
| CN | 104098580 A | 10/2014 |
| CN | 104133010 A | 11/2014 |
| CN | 104133012 A | 11/2014 |
| CN | 104297366 A | 1/2015 |
| CN | 104447770 A | 3/2015 |
| CN | 104447771 A | 3/2015 |
| CN | 104487072 A | 4/2015 |
| CN | 104507472 A | 4/2015 |
| CN | 103342707 B | 9/2015 |
| CN | 104974167 A | 10/2015 |
| CN | 104974168 A | 10/2015 |
| CN | 105377245 A | 3/2016 |
| CN | 103254201 B | 4/2016 |
| CN | 103351393 B | 4/2016 |
| CN | 104098580 B | 4/2016 |
| CN | 105566336 A | 5/2016 |
| CN | 105693735 A | 6/2016 |
| CN | 105813636 A | 7/2016 |
| CN | 103864802 B | 8/2016 |
| EP | 0569096 A1 | 11/1993 |
| EP | 0730865 B1 | 12/2001 |
| EP | 1547650 A1 | 6/2005 |
| EP | 1181935 B1 | 9/2005 |
| EP | 1576985 A1 | 9/2005 |
| EP | 1684681 A1 | 8/2006 |
| EP | 1765310 A2 | 3/2007 |
| EP | 2236138 A1 | 10/2010 |
| EP | 2468750 A1 | 6/2012 |
| EP | 2154134 B1 | 10/2012 |
| EP | 2599847 A1 | 6/2013 |
| EP | 2878298 A1 | 6/2015 |
| EP | 3020782 A1 | 5/2016 |
| EP | 3031458 A1 | 6/2016 |
| EP | 3329914 A1 | 6/2018 |
| EP | 3329915 A1 | 6/2018 |
| EP | 3338768 A1 | 6/2018 |
| JP | 5301190 B2 | 9/2013 |
| JP | 2014214109 A | 11/2014 |
| JP | 2016056142 A | 4/2016 |
| JP | 2017178799 A | 10/2017 |
| KR | 20130120648 A | 11/2013 |
| KR | 20160107610 A | 9/2016 |
| KR | 20160108258 A | 9/2016 |
| RU | 2352336 C2 | 4/2009 |
| RU | 2450805 C2 | 5/2012 |
| WO | WO-8600806 A1 | 2/1986 |
| WO | WO-9518603 A1 | 7/1995 |
| WO | WO-9854186 A1 | 12/1998 |
| WO | WO-9932108 A1 | 7/1999 |
| WO | WO-0064418 A2 | 11/2000 |
| WO | WO-03013482 A1 | 2/2003 |
| WO | WO-03066039 A1 | 8/2003 |
| WO | WO-2004017941 A2 | 3/2004 |
| WO | WO-2004039322 A2 | 5/2004 |
| WO | WO-2005084654 A2 | 9/2005 |
| WO | WO-2006000222 A2 | 1/2006 |
| WO | WO-2006023497 A2 | 3/2006 |
| WO | WO-2006079547 A2 | 8/2006 |
| WO | WO-200610613 5 A1 | 10/2006 |
| WO | WO-2006106136 A1 | 10/2006 |
| WO | WO-2007017750 A1 | 2/2007 |
| WO | WO-2007046554 A1 | 4/2007 |
| WO | WO-2007124757 A2 | 11/2007 |
| WO | WO-2007137224 A2 | 11/2007 |
| WO | WO-2007145996 A2 | 12/2007 |
| WO | WO-2007137224 A3 | 1/2008 |
| WO | WO-2008003460 A1 | 1/2008 |
| WO | WO-2008066180 A1 | 6/2008 |
| WO | WO-2008078482 A1 | 7/2008 |
| WO | WO-2008141438 A1 | 11/2008 |
| WO | WO-2009000890 A2 | 12/2008 |
| WO | WO-2009017453 A1 | 2/2009 |
| WO | WO-2009102962 A2 | 8/2009 |
| WO | WO-2009135091 A1 | 11/2009 |
| WO | WO-2010011232 A1 | 1/2010 |
| WO | WO-2010060742 A1 | 6/2010 |
| WO | WO-2010073326 A1 | 7/2010 |
| WO | WO-2010074182 A1 | 7/2010 |
| WO | WO-2010074183 A1 | 7/2010 |
| WO | WO-2010080757 A2 | 7/2010 |
| WO | WO-2010110914 A2 | 9/2010 |
| WO | WO-2010112530 A1 | 10/2010 |
| WO | WO-2010119455 A2 | 10/2010 |
| WO | WO-2010124187 A2 | 10/2010 |
| WO | WO-2010127674 A1 * | 11/2010 ........... A61K 9/7023 |
| WO | WO-2011012654 A1 | 2/2011 |
| WO | WO-2011047341 A2 | 4/2011 |
| WO | WO-2011085188 A1 | 7/2011 |
| WO | WO-2011087755 A2 | 7/2011 |
| WO | WO-2011101799 A1 | 8/2011 |
| WO | WO-2011107855 A2 | 9/2011 |
| WO | WO-2011143755 A1 | 11/2011 |
| WO | WO-2012038975 A2 | 3/2012 |
| WO | WO-2012065102 A2 | 5/2012 |
| WO | WO-2012066565 A2 | 5/2012 |
| WO | WO-2012114325 A1 | 8/2012 |
| WO | WO-2012123325 A1 | 9/2012 |
| WO | WO-2012163665 A1 | 12/2012 |
| WO | WO-2013024492 A2 | 2/2013 |
| WO | WO-2013027052 A1 | 2/2013 |
| WO | WO-2013035109 A1 | 3/2013 |
| WO | WO-2013041435 A1 | 3/2013 |
| WO | WO-2013041604 A1 | 3/2013 |
| WO | WO-2013061247 A1 | 5/2013 |
| WO | WO-2013114400 A2 | 8/2013 |
| WO | WO-2013150032 A1 | 10/2013 |
| WO | WO-2013190481 A1 | 12/2013 |
| WO | WO-2014064076 A1 | 5/2014 |
| WO | WO-2014078377 A1 | 5/2014 |

(56) References Cited

FOREIGN PATENT DOCUMENTS

| WO | WO-2014080378 A1 | 5/2014 |
|----|----|----|
| WO | WO-2014084401 A1 | 6/2014 |
| WO | WO-2014127786 A1 | 8/2014 |
| WO | WO-2014152965 A2 | 9/2014 |
| WO | WO-2014160026 A2 | 10/2014 |
| WO | WO-2014160155 A2 | 10/2014 |
| WO | WO-2014160167 A1 | 10/2014 |
| WO | WO-2014207664 A2 | 12/2014 |
| WO | WO-2015027342 A1 | 3/2015 |
| WO | WO-2014207664 A3 | 4/2015 |
| WO | WO-2015071831 A1 | 5/2015 |
| WO | WO-2015120317 A1 | 8/2015 |
| WO | WO-2015127416 A1 | 8/2015 |
| WO | WO-2015127556 A1 | 9/2015 |
| WO | WO-2015127557 A1 | 9/2015 |
| WO | WO-2015127558 A1 | 9/2015 |
| WO | WO-2015154025 A1 | 10/2015 |
| WO | WO-2015154030 A1 | 10/2015 |
| WO | WO-2015177212 A1 | 11/2015 |
| WO | WO-2015191554 A1 | 12/2015 |
| WO | WO-2016009063 A1 | 1/2016 |
| WO | WO-2016020573 A1 | 2/2016 |
| WO | WO-2016023658 A1 | 2/2016 |
| WO | WO-2016060564 A1 | 4/2016 |
| WO | WO-2016062285 A1 | 4/2016 |
| WO | WO-2016089737 A1 | 6/2016 |
| WO | WO-2016090228 A1 | 6/2016 |
| WO | WO-2016114655 A1 | 7/2016 |
| WO | WO-2016130408 A1 | 8/2016 |
| WO | WO-2016138138 A1 | 9/2016 |
| WO | WO-2016140087 A1 | 9/2016 |
| WO | WO-2016166679 A1 | 10/2016 |
| WO | WO-2016170102 A1 | 10/2016 |
| WO | WO-2016176519 A1 | 11/2016 |
| WO | WO-2016207466 A1 | 12/2016 |
| WO | WO-2017018321 A1 | 2/2017 |
| WO | WO-2017018322 A1 | 2/2017 |
| WO | WO-2017131034 A1 | 8/2017 |

OTHER PUBLICATIONS

Health Canada, "A Report on Mental Illnesses in Canada," Health Canada Editorial Board Mental Illnesses, Canada, pp. 1-91 (Oct. 2002).
Health Canada, "A Report on Mental Illnesses in Canada," Health Canada Editorial Board Mental Illnesses, Canada, pp. 92-111 (Oct. 2002).
Acosta, F.J., et al., "Medication Adherence in Schizophrenia," World Journal of Psychiatry 2(5):74-82, Baishideng Publishing Group, United States (Oct. 2012).
Amato, D., et al., "Neuroadaptations to Antipsychotic Drugs: Insights From Pre-clinical and Human Post-mortem Studies," Neuroscience and Biobehavioral Reviews 76 (Pt B):317-335, Pergamon Press, United States (May 2017).
Andree, B., et al., "Central 5-HT2A and D2 Dopamine Receptor Occupancy After Sublingual Administration of ORG 5222 in Healthy Men," Psychopharmacology 131:339-345, Springer-Verlag, Germany (1997).
"Saphris®/Sycrest® (asenapine) Bipolar I disorder, MSD," Monograph, 2011, 58 Pages.
"Asenapine maleate," Sicherheitsdatenblatt, Sigma-Aldrich, 2014, 7 Pages.
"Australian Public Assessment Report for Asenapine," Australian Government, Department of Health and Aging, Apr. 2011, 154 pages.
Balaraman, R., and Gandhi, H., "Asenapine, a New Sublingual Atypical Antipsychotic," Journal of Pharmacology & Pharmacotherapeutics 1(1):60-61, Medknow Publications and Media, India (Jan. 2010).
Bartlett, J.A., and Maarschalk, K., "Understanding the Oral Mucosal Absorption and Resulting Clinical Pharmacokinetics of Asenapine," AAPS PharmSciTech 13(4):1110-1115, Springer, United States (Dec. 2012).

Benson, H.A.E., and Watkinson, A.C., eds., "Transdermal and Topical Drug Delivery: Principles and Practice," 448 pages, John Wiley & Sons, Inc., United States (2012).
National Institute for Health and Care Excellence, "Bipolar disorder: assessment and management-clinical guideline," Published: Sep. 24, 2014, 46 Pages.
Bishara D and Taylor D., "Asenapine Monotherapy in the Acute Treatment of Both Schizophrenia and Bipolar I Disorder," Neuropsychiatric Disease and Treatment, 5:483-490, Dove Medical Press, New Zealand (2009).
Brisch R., et al., "The Role of Dopamine in Schizophrenia From a Neurobiological and Evolutionary Perspective: Old Fashioned, but Still in Vogue," Frontiers in Psychiatry, 5:47, Frontiers Research Foundation, Switzerland (May 2014).
Broekkamp, C.L., et al., "Behavioural Pharmacology of Trans-5-chloro-2-methyl-2,3,3a,12b-tetrahydro-1h-dibenz[2,3:6,7]oxepino-[4,5-c]pyrrolidine Maleate, a Compound Interacting With Dopaminergic and Serotonergic Receptors," Drug Discovery, 40 (5):544-549, Editio Cantor, Germany (May 1990).
Buchanan R. W., et al., "Asenapine Versus Olanzapine in People With Persistent Negative Symptoms of Schizophrenia," Journal of Clinical Psychopharmacology, 32(1):36-45, Williams And Wilkins, United States (Feb. 2012).
Byers A., et al., "Asenapine Versus Placebo for Schizophrenia," The Cochrane Database of Systematic Reviews, 2015 (11):CD011458, Wiley, United Kingdom (Nov. 2015).
Caresano C., et al., "Cost-effectiveness of Asenapine in the Treatment of Patients With Bipolar I Disorder With Mixed Episodes in an Italian Context," Advances in Therapy, 31 (8):873-890, Springer Healthcare Communications, United States (Aug. 2014).
Cazorla P., et al., "Safety and Tolerability of Switching to Asenapine From Other Antipsychotic Agents: Pooled Results From Two Randomized Multicenter Trials in Stable Patients With Persistent Negative Symptoms in Schizophrenia," Neuropsychiatric Disease and Treatment, 8:247-257, Dove Medical Press, New Zealand (2012).
Chapel S., et al., "Exposure-response Analysis in Patients With Schizophrenia to Assess the Effect of Asenapine on QTc Prolongation," Journal of Clinical Pharmacology, 49(11):1297-1308, Wiley, United Kingdom (Nov. 2009).
Cipriani, A., et al., "Comparative Efficacy and Acceptability of Antimanic Drugs in Acute Mania: a Multiple-treatments Meta-analysis," Lancet, 378(9799):1306-1315, Elsevier, United Kingdom (Oct. 2011).
Citrome L., "Asenapine for Schizophrenia and Bipolar Disorder: a Review of the Efficacy and Safety Profile for This Newly Approved Sublingually Absorbed Second-generation Antipsychotic," International Journal of Clinical Practice, 63 (12):1762-1784, Wiley, United Kingdom (Dec. 2009).
Citrome L., "Asenapine Review, Part I: Chemistry, Receptor Affinity Profile, Pharmacokinetics and Metabolism," Expert Opinion on Drug Metabolism & Toxicology, 10 (6):893-903, Informa Healthcare, United Kingdom (Jun. 2014).
Citrome L., "Asenapine Review, Part II: Clinical Efficacy, Safety and Tolerability," Expert Opinion on Drug Safety, 13 (6):803-830, Taylor & Francis, United Kingdom (Jun. 2014).
Chrome L., "Role of Sublingual Asenapine in Treatment of Schizophrenia," Neuropsychiatric Disease and Treatment, 7:325-339, Dove Medical Press, New Zealand (2011).
NCT01549041, "Once-Daily Asenapine for Schizophrenia," ClinicalTrials.gov, 3 pages.
Correll C.U., et al., "Cardiometabolic Risk of Second-generation Antipsychotic Medications During First-time Use in Children and Adolescents," JAMA, 302 (16): 1765-1773, American Medical Association, United States (Oct. 2009).
Correll C.U., et al., "Lower Risk for Tardive Dyskinesia Associated With Second-generation Antipsychotics: a Systematic Review of 1-year Studies," The American Journal of Psychiatry, 161(3):414-425, American Psychiatric Association, United States (Mar. 2004).
Correll C.U., et al., "What Are We Looking for in New Antipsychotics?," The Journal of Clinical Psychiatry, 72( Suppl 1):9-13, Physicians Postgraduate Press, United States (2011).

(56) References Cited

OTHER PUBLICATIONS

Costall, B., et al., "Actions of Org 5222 as a Novel Psychotropic Agent," Pharmacology Biochemistry and Behavior, 35(3):607-615, Elsevier, United States (Mar. 1990).

Cramer J. A and Rosenheck R., "Compliance With Medication Regimens for Mental and Physical Disorders," Psychiatric Services 49 (2): 196-201, American Psychiatric Association, United States (Feb. 1998).

Davidson M., et al., "Cognitive Effects of Antipsychotic Drugs in First-episode Schizophrenia and Schizophreniform Disorder: a Randomized, Open-label Clinical Trial (EUFEST)," The American Journal of Psychiatry, 166 (6):675-682, American Psychiatric Association, United States (Jun. 2009).

De Hert M., et al., "Metabolic and Cardiovascular Adverse Effects Associated With Antipsychotic Drugs," Nature Reviews Endocrinology, 8(2): 114-126, Nature Publishing Group, United Kingdom (Oct. 2011).

Dogterom, P., et al., "Asenapine Safety, Tolerability, and Pharmacokinetics After Single and Multiple Doses in Healthy Volunteers," Clinical Pharmacology in Drug Development, 1(4):131-143, Wiley, United States (Oct. 2012).

Dogterom, P., et al., "The Effect of Food on the High Clearance Drug Asenapine After Sublingual Administration to Healthy Male Volunteers," European Journal of Clinical Pharmacology, 71(1):65-74, Springer, Germany (Jan. 2015).

"Draft Guidance on Asenapine Maleate—Contains Nonbinding Recommendations," 4 pages (2013).

Dubovsky S.L., et al., "Short-term Safety and Pharmacokinetic Profile of Asenapine in Older Patients With Psychosis," International Journal of Geriatric Psychiatry, 27(5):472-482, John Wiley, United Kingdom (May 2012).

"Evaluation of Medicines for Human Use," European Medicine Agency, An agency of the European Union, 2010, 88 pages.

Fagiolini, A., et al., "Asenapine for the Treatment of Manic and Mixed Episodes Associated With Bipolar I Disorder: From Clinical Research to Clinical Practice," Expert Opinion on Pharmacotherapy, 14(4):489-504, Informa Healthcare, United Kingdom (Mar. 2013).

Findling R.L., et al., "Long-term Safety of Asenapine in Pediatric Patients Diagnosed With Bipolar I Disorder: a 50-week Open-label, Flexible-dose Trial," Paediatric Drugs, 18 (5):367-378, Springer International, Switzerland (Oct. 2016).

Fleischhacker W.W., et al., "Schizophrenia—time to Commit to Policy Change," Schizophrenia Bulletin, 40 (Suppl 3):S165-S194, Oxford University Press, United Kingdom (Apr. 2014).

Fleming, K., el al., "P.3.C.073 Effects of Asenapine on Cognitive Function in Acute Schizophrenia: a Placebo- and Risperidone-controlled Trial," European Neuropsychopharmacology, 17(4):S466-S467, Elsevier, Netherlands (Oct. 2007).

Fountoulakis K.N., et al., "The International College of Neuropsychopharmacology (CINP) Treatment Guidelines for Bipolar Disorder in Adults (CINP-BD-2017), Part 1: Background and Methods of the Development of Guidelines," International Journal of Neuropsychopharmacology, 20(2):98-120, Oxford University Press, United Kingdom (2017).

Fountoulakis K.N., et al., "The International College of Neuro-Psychopharmacology (CINP) Treatment Guidelines for Bipolar Disorder in Adults (CINP-BD-2017), Part 3: The Clinical Guidelines," The International Journal of Neuropsychopharmacology, 20(2):180-195, Oxford University Press, United Kingdom (Feb. 2017).

Franberg, O., et al., "Asenapine, a Novel Psychopharmacologic Agent: Preclinical Evidence for Clinical Effects in Schizophrenia," Psychopharmacology, 196(3):417-429, Springer-Verlag, Germany (Feb. 2008).

Friberg, L.E., et al., "Modeling and Simulation of the Time Course of Asenapine Exposure Response and Dropout Patterns in Acute Schizophrenia," Clinical Pharmacology & Therapeutics, 86(1):84-91, Wiley, United States (Jul. 2009).

Geddes J., et al., "Atypical Antipsychotics in the Treatment of Schizophrenia: Systematic Overview and Meta-regression Analysis," BMJ (Clinical researched.), 321 (7273): 1371-1376, British Medical Association, United Kingdom (Dec. 2000).

Gerrits, M., et al., "Effect of Absorption Site on the Pharmacokinetics of Sublingual Asenapine in Healthy Male Subjects," Biopharmaceutics & Drug Disposition, 31(5-6):351-357, Wiley, United Kingdom (Jul. 2010).

Gerrits, M.G., et al., "Valproate Reduces the Glucuronidation of Asenapine Without Affecting Asenapine Plasma Concentrations," The Journal of Clinical Pharmacology, 52(5):757-765, Wiley, United Kingdom (May 2012).

Goodwin G.M., et al., "Evidence-based Guidelines for Treating Bipolar Disorder: Revised Second Edition-recommendations From the British Association for Psychopharmacology," Journal of Psychopharmacology ,23(4):346-388, Sage Publications, United States (Jun. 2009).

Grunder, G., et al., "Therapeutic Plasma Concentrations of Antidepressants and Antipsychotics: Lessons From PET Imaging," Pharmacopsychiatry, 44(6):236-248, Georg Thieme Verlag, Germany (Sep. 2011).

Grunze H., et al., "The World Federation of Societies of Biological Psychiatry (Wfsbp) Guidelines for the Biological Treatment of Bipolar Disorders: Update 2012 on the Long-term Treatment of Bipolar Disorder," The World Journal of Biological Psychiatry, 14 (3):154-219, Informa Healthcare, United Kingdom (Apr. 2013).

Hagg S., et al., "Associations Between Venous Thromboembolism and Antipsychotics. A Study of the Who Database of Adverse Drug Reactions," Drug Safety, 31 (8):685-694, Springer International, New Zealand (2008).

Hiemke C., et al., "AGNP Consensus Guidelines for Therapeutic Drug Monitoring in Psychiatry: Update 2011.," Pharmacopsychiatry, 44 (6):195-235, Georg Thieme Verlag, Germany (Sep. 2011).

Hirschfeld, R.M, "Differential Diagnosis of Bipolar Disorder and Major Depressive Disorder," Journal of Affective Disorders, 169 Suppl 1:S12-S16, Elsevier/North-Holland Biomedical Press, Netherlands (Dec. 2014).

International Search Report and Written Opinion for International Application No. PCT/EP2018/066950, European Patent Office, Netherlands, dated Aug. 27, 2018, 9 pages.

Jones P.B., et al., "Randomized Controlled Trial of the Effect on Quality of Life of Second—Vs First-generation Antipsychotic Drugs in Schizophrenia: Cost Utility of the Latest Antipsychotic Drugs in Schizophrenia Study (Cutlass 1)," Archives of General Psychiatry, 63 (10):1079-1087, American Medical Association, United States (Oct. 2006).

Judd L.L and Akiskal H. S., "The Prevalence and Disability of Bipolar Spectrum Disorders in the US Population: Re-analysis of the ECA Database Taking Into Account Subthreshold Cases," Journal of Affective Disorders, 73 (1-2):123-131, Elsevier/North-Holland Biomedical Press, Netherlands (Jan. 2003).

Kahn, R.S., et al., "Schizophrenia," Nature Reviews Disease Primers, 1:1-23, Nature Publishing Group, United Kingdom (Nov. 2015).

Kaminsky, B.M., et al., "Alternate Routes of Administration of Antidepressant and Antipsychotic Medications," Annals of Pharmacotherapy, 49(7):2 pages, Sage, United States (Jul. 2015).

Kane J.M., et al., "Efficacy and Safety of Asenapine in a Placebo- and Haloperidol-controlled Trial in Patients With Acute Exacerbation of Schizophrenia," Journal of Clinical Psychopharmacology, 30 (2):106-115, Williams And Wilkins, United States (Apr. 2010).

Kane, J.M., et al., "Non-adherence to Medication in Patients with Psychotic Disorders: Epidemiology, Contributing Factors and Management Strategies," World Psychiatry, 12(3):216-226, Masson Italy, Italy (Oct. 2013).

Kapil R.P., et al., "Once-weekly Transdermal Buprenorphine Application Results in Sustained and Consistent Steady-state Plasma Levels," Journal of Pain and Symptom Management, 46 (1):65-75, Elsevier, United States (Jul. 2013).

"Asenapin," KBV, Wirkstoff Aktuell, 4 pages (2013).

Kemp, D.E., et al., "Weight Change and Metabolic Effects of Asenapine in Patients With Schizophrenia and Bipolar Disorder," The Journal of Clinical Psychiatry, 75(3):238-245, Physicians Postgraduate Press, United States (Mar. 2014).

Kessler R.C., et al., "Prevalence, Severity, and Comorbidity of 12-month Dsm-iv Disorders in the National Comorbidity Survey

(56) References Cited

OTHER PUBLICATIONS

Replication," Archives of General Psychiatry, 62 (6):617-627, American Medical Association, United States (Jun. 2005).
Ketter T.A., et al., "Long-term Safety and Tolerability of Asenapine: a Double-blind, Uncontrolled, Long-term Extension Trial in Adults With an Acute Manic or Mixed Episode Associated With Bipolar I Disorder," Journal of Affective Disorders, 207:384-392, Elsevier/North-Holland Biomedical Press, Netherlands (Jan. 2017).
Kikkert, M.J., et al., "Medication Adherence in Schizophrenia: Exploring Patients', Carers' and Professionals' Views," Schizophrenia Bulletin, 32(4):786-794, Oxford University Press, United States (Oct. 2006).
Kinoshita, T., et al., "Efficacy and Safety of Asenapine in Asian Patients With an Acute Exacerbation of Schizophrenia: a Multicentre, Randomized, Double-blind, 6-week, Placebo-controlled Study," Psychopharmacology, 233(14):2663-2674, Springer-Verlag, Germany (Jul. 2016).
Lachaine J., et al., "Cost-effectiveness of asenapine in the treatment of bipolar disorder in Canada," BMC Psychiatry, 14:16, (2014).
Lachaine J., et al., "Cost-effectiveness of asenapine in the treatment of schizophrenia in Canada," Journal of Medical Economics, 17 (4):296-304, Taylor & Francis, United Kingdom (2014).
Landbloom R., et al., "Asenapine for the Treatment of Adults With an Acute Exacerbation of Schizophrenia: Results From a Randomized, Double-blind, Fixed-dose, Placebo-controlled Trial With Olanzapine as an Active Control," CNS Spectrums, 22 (4):333-341, Cambridge University Press, United Kingdom (Aug. 2017).
Landbloom, R.L., et al., "Asenapine: Efficacy and Safety of 5 and 10mg Bid in a 3-week, Randomized, Double-blind, Placebo-controlled Trial in Adults With a Manic or Mixed Episode Associated With Bipolar I Disorder," Journal of Affective Disorders, 190:103-110, Elsevier/North-Holland Biomedical Press, Netherlands (Jan. 2016).
Lehman A.F., et al., "Practice Guideline for the Treatment of Patients With Schizophrenia," Second Edition, Work Group on Schizophrenia, APA Practice Guidelines, 2010, 184 pages.
Leucht S., et al., "Comparative Efficacy and Tolerability of 15 Antipsychotic Drugs in Schizophrenia: a Multiple-treatments Meta-analysis," Lancet 382 (9896):951-962, Elsevier, United Kingdom (Sep. 2013).
Leucht S., et al., "New Generation Antipsychotics Versus Low-potency Conventional Antipsychotics: a Systematic Review and Meta-analysis," Lancet 361 (9369): 1581-1589, Elsevier, United Kingdom (May 2003).
Lieberman J. A., et al., "Effectiveness of Antipsychotic Drugs in Patients With Chronic Schizophrenia," The New United Kingdom Journal of Medicine, 353 (12):1209-1223, Massachusetts Medical Society, United States (Sep. 2005).
Lincoln, M.J., "Asenepine for schizophrenia and bipolar 1 disorder," Bipolar Disorders 8(12):1-6, Dec. 2009.
Makdisi J., et al., "Pityriasis Rosea-like Drug Reaction to Asenapine," Journal of Drugs in Dermatology: JDD, 12 (9):1050-1051, Physicians Continuing Education Corporation, United States (Sep. 2013).
Maletic, V., et al., "Integrated Neurobiology of Bipolar Disorder," Frontiers in Psychiatry, 5:98, Frontiers Research Foundation, Switzerland (2014).
Mutalik, S., "Nano-Carrier Based Transdermal Formulation of an Antipsychotic Drug: Development and In Vitro and In Vivo Evaluations," Conference: AAPS Annual Meeting and Exposition, Oct. 2015, 1 page.
Martin-Blanco, A., et al., "Asenapine in the Treatment of Borderline Personality Disorder: an Atypical Antipsychotic Alternative," International Clinical Psychopharmacology, 29(2):120-123, Lippincott Williams And Wilkins, United Kingdom (Mar. 2014).
Mauri M.C., et al., "Clinical Pharmacology of Atypical Antipsychotics: an Update," EXCLI Journal, 13:1163-1191, University of Mainz, Germany (Oct. 2014).
McCormick, U., et al., "Diagnosis and Treatment of Patients With Bipolar Disorder: a Review for Advanced Practice Nurses," Journal of the American Association of Nurse Practitioners, 27(9):530-542, Wolters Kluwer, United States (Sep. 2015).
McGrath J., et al., "Schizophrenia: a Concise Overview of Incidence, Prevalence, and Mortality," Epidemiologic Reviews, 30:67-76, Oxford University Press on Behalf of Johns Hopkins Bloomberg School of Public Health, United States (2008).
McIntyre R.S and Wong R., "Asenapine: a Synthesis of Efficacy Data in Bipolar Mania and Schizophrenia," Clinical Schizophrenia & Related Psychoses, 5 (4):217-220, Walsh Medical Media, United States (Jan. 2012).
McIntyre, R.S., et al., "A 3-week, Randomized, Placebo-controlled Trial of Asenapine in the Treatment of Acute Mania in Bipolar Mania and Mixed States," Bipolar Disorder, 11(7):1-15, Wiley-Blackwell Munksgaard, Denmark, (Nov. 2009).
McIntyre, R.S., et al., "Asenapine in the Treatment of Acute Mania in Bipolar I Disorder: a Randomized, Double-blind, Placebo-controlled Trial," Journal of Affective Disorders, 122(1-2):27-38, Elsevier/North-Holland Biomedical Press, Netherlands (Apr. 2010).
Meltzer, H.Y., "Chapter 58: Mechanism of Action of Atypical Antipsychotic Drugs," 2002, 14 pages.
Merikangas K.R., et al., "Lifetime and 12-month Prevalence of Bipolar Spectrum Disorder in the National Comorbidity Survey Replication," Archives of General Psychiatry, 64 (5):543-552, American Medical Association, United States (May 2007).
Merikangas K.R., et al., "Prevalence and Correlates of Bipolar Spectrum Disorder in the World Mental Health Survey Initiative," Archives of General Psychiatry, 68 (3):241-251, American Medical Association, United States (Mar. 2011).
Meyer J.M., "Understanding Depot Antipsychotics: an Illustrated Guide to Kinetics," CNS Spectrums, 18 (Suppl 1):58-67, Cambridge University Press, United Kingdom (Dec. 2013).
Minassian A and Young J.W., "Evaluation of the Clinical Efficacy of Asenapine in Schizophrenia," Expert Opinion on Pharmacotherapy, 11 (12):2107-2115, Informa Healthcare, United Kingdom (Aug. 2010).
Miyake, N., et al., "New Serotonin/Dopamine Antagonists for the Treatment of Schizophrenia," Clinical Schizophrenia & Related Psychoses, 6(3):122-133, (Oct. 2012).
Mura G., et al., "Schizophrenia: from Epidemiology to Rehabilitation," Clinical Practice and Epidemiology in Mental Health: CP & EMH, 8:52-66, Bentham Open, United Arab Emirates, (2012).
"Sycrest® (Asenapin)," Neue Arzneimittel, 2011, 2 pages.
Nivoli A.M., et al., "New Treatment Guidelines for Acute Bipolar Mania: a Critical Review," Journal of Affective Disorders, 140 (2):125-141, Elsevier/North-Holland Biomedical Press, Netherlands (Oct. 2012).
Office Action dated Aug. 15, 2019, in U.S. Appl. No. 15/847,360, inventor Mohr, Patrick et al., filed Dec. 19, 2017, 20 pages.
Peeters, P., et al., "Asenapine Pharmacokinetics in Hepatic and Renal Impairment," Clinical Pharmacokinetics, 50(7):471-481, Adis, part of Springer Science+Business Media, Switzerland (Jul. 2011).
"5.5 Pharmacokinetics—Sublingual: 5.5.1 Single Dose Pharmacokinetics," 2008, 279 pages.
Picchioni, M.M., "Schizophrenia," The BMJ 335:91-95, Clinical Review (Jul. 2007).
Pompili M., et al., "The Role of Asenapine in the Treatment of Manic or Mixed States Associated With Bipolar I Disorder," Neuropsychiatric Disease and Treatment, 7:259-265, Dove Medical Press, New Zealand (2011).
Potkin, S., et al., "Asenapine in Schizophrenia: an Overview of Clinical Trials in the Olympia Program," Schizophrenia Research, 102(1):258-258, Elsevier B.V., Netherlands (Jun. 2008).
Potkin S.G., et al., "Efficacy and Tolerability of Asenapine in Acute Schizophrenia: a Placebo- and Risperidone-controlled Trial," The Journal of Clinical Psychiatry, 68(10): 1492-1500, Physicians Postgraduate Press, United States (Oct. 2007).
Potkin, S.G., et al., "Long-term Effects of Asenapine or Olanzapine in Patients With Persistent Negative Symptoms of Schizophrenia: a Pooled Analysis," Schizophrenia Research, 150(2-3):442-449, Elsevier Science Publisher B.V., Netherlands (Nov. 2013).
Rado, J and Janicak, P.G, "Pharmacological and Clinical Profile of Recently Approved Second-generation Antipsychotics: Implica-

(56) References Cited

OTHER PUBLICATIONS tions for Treatment of Schizophrenia in Older Patients," Drugs Aging, 29(10):783-791, Springer International, New Zealand (Oct. 2012).
"Receptor Binding Profiles of Atypical Antipsychotics: Mechanisms of Therapeutic Actions and Adverse Side Effects," Presented at the 2012 NEI Global Psychopharmacology Congress, 1 page.
Regier D.A., et al., "The De Facto US Mental and Addictive Disorders Service System. Epidemiologic Catchment Area Prospective 1-year Prevalence Rates of Disorders and Services," Archives of General Psychiatry, 50 (2):85-94, American Medical Association, United States (Feb. 1993).
Reynolds G.P., "Receptor Mechanisms of Antipsychotic Drug Action in Bipolar Disorder—Focus on Asenapine," Therapeutic Advances in Psychopharmacology, 1 (6):197-204, Sage, United Kingdom (Dec. 2011).
Ross, C.A., et al., "Neurobiology of Schizophrenia," Neuron, 52(1):139-153, Cell Press, United States (Oct. 2006).
"Product Information Saphris®️ (asenapine maleate)," 25 pages.
"Saphris®️ (asenapine) 2.5 mg Sublingual Tablets for the Acute Treatment of Manic or Mixed Episodes of Bipolar I Disorder in Pediatric Patients (ages 10-17) Now Available in Pharmacies throughout the U.S," accessed from PRNewswire, 2015, 8 pages.
Saphris (asenapine) Sublingual Tablets, Jul. 30, 2009 PDAC, Briefing Book, vol. 1, U.S. Food and Drug Administration, 1068 Pages.
"Product Monograph Saphris®️ (asenapine sublingual tablets)—Antypsychotic," 2016, 49 Pages.
Sawyer, L., et al., "Cost-effectiveness of Asenapine in the Treatment of Bipolar I Disorder Patients With Mixed Episodes," Journal of Medical Economics, 17(7):508-519, Taylor & Francis, United Kingdom (Jul. 2014).
Scheidemantel, T., et al., "Asenapine for Bipolar Disorder," Neuropsychiatric Disease and Treatment, 11:3007-3017, Dove Medical Press, New Zealand (2015).
"Schizophrenia: Core Interventions in the Treatment and Management of Schizophrenia in Adults in Primary and Secondary Care (update)," NICE guideline, Draft for consultation, Sep. 2008, 39 Pages.
Schoemaker, J., et al., "Long-Term Assessment of Asenapine vs. Olanzapine in Patients with Schizoaffective Disorder," Pharmacopsychiatry, 43(4):e1-e10, Georg Thieme Verlag KG, Germany (2010).
Shahid, M., et al., "Asenapine: a Novel Psychopharmacologic Agent With a Unique Human Receptor Signature," Journal of Psychopharmacology, 23(1):2 pages, Sage Publications, United States (Feb. 2008).
Shreya, A.B., et al., "Nano-transfersomal Formulations for Transdermal Delivery of Asenapine Maleate: in Vitro and in Vivo Performance Evaluations," Journal of Liposome Research, 26(3):221-232, Informa Healthcare, United Kingdom (Sep. 2016).
Simeone J.C., el al., "An Evaluation of Variation in Published Estimates of Schizophrenia Prevalence From 1990-2013: A Systematic Literature Review," BMC Psychiatry, 15:193, BioMed Central, United Kingdom (Aug. 2015).
Smith E.N., et al., "Asenapine Augmentation and Treatment-resistant Schizophrenia in the High-secure Hospital Setting," Therapeutic Advances in Psychopharmacology, 4 (5):193-197, Sage, United Kingdom (Oct. 2014).
Smyth A.M., et al., "The Neuroimmunology of Schizophrenia," Clinical Psychopharmacology and Neuroscience, 11(3):107-117, Korean College of Neuropsychopharmacology, Korea, (Dec. 2013).

"Stellenwert Von Asenapin (Sycrest®️) in Der Behandlung Von Bipolaren Storungen—Clinical Experience Program (CEP): Erste Praktische Erfahrungen in Der Schweiz," Aug. 2013, 12 pages.
"Sycrest®️ 10 mg Sublingualtabletten," Fachinformation (zusammenfassung der merkmale des arzneimittels, 2012, 6 pages.
Szegedi A., et al., "Effects of Asenapine on Depressive Symptoms in Patients With Bipolar I Disorder Experiencing Acute Manic or Mixed Episodes: a Post Hoc Analysis of Two 3-week Clinical Trials," BMC Psychiatry, 11:101, BioMed Central, United Kingdom (Jun. 2011).
Tarazi, F.I and Stahl, S.M, "Iloperidone, Asenapine and Lurasidone: a Primer on Their Current Status," Expert Opinion on Pharmacotherapy, 13(13):1911-1922, Informa Healthcare, United Kingdom (Sep. 2012).
Tiihonen J., et al., "11-year Follow-up of Mortality in Patients With Schizophrenia: aPopulation-based Cohort Study (Fin11 Study)," Lancet (London, United Kingdom), 374 (9690):620-627, Elsevier, United Kingdom (Aug. 2009).
Van De Wetering-Krebbers S.F., et al., "Metabolism and Excretion of Asenapine in Healthy Male Subjects," Drug Metabolism and Disposition: the Biological Fate of Chemicals, 39 (4):580-590, American Society for Pharmacology and Experimental Therapeutics, United States (Apr. 2011).
Weber, J and McCormack, P.L., "Asenapine," CNS Drugs, 23(9):781-792, Springer, Germany (Sep. 2009).
"Zusammenfassung Der Merkmale Des Arzneimittels," 1 Anhang I, 2010, 44 pages.
Office Action dated Jan. 31, 2020, in U.S. Appl. No. 15/847,360, inventor Mohr, Patrick et al., filed Dec. 19, 2017, 22 pages.
Office Action dated Sep. 20, 2019, in U.S. Appl. No. 16/445,582, inventor Mohr, Patrick et al., filed Jun. 19, 2019, 15 pages.
Final Office Action dated Feb. 20, 2020, in U.S. Appl. No. 16/445,582, inventor Mohr, Patrick et al., filed Jun. 19, 2019, 25 pages.
Office Action dated Jul. 8, 2020, in U.S. Appl. No. 16/445,582, inventor Mohr, Patrick et al., filed Jun. 19, 2019, 25 pages.
Final Office Action dated Sep. 2, 2020, in U.S. Appl. No. 16/445,582, inventor Mohr, Patrick et al., filed Jun. 19, 2019, 34 pages.
Office Action dated Jun. 9, 2020, in U.S. Appl. No. 16/788,128, inventor Mohr, Patrick et al., filed Feb. 11, 2020, 18 pages.
Final Office Action dated Aug. 19, 2020, in U.S. Appl. No. 16/788,128, inventor Mohr, Patrick et al., filed Feb. 11, 2020, 26 pages.
International Search Report and Written Opinion for International Application No. PCT/EP2019/066226, European Patent Office, Netherlands, dated Sep. 18, 2019, 11 pages.
International Search Report and Written Opinion for International Application No. PCT/EP2019/066270, European Patent Office, Netherlands, dated Aug. 29, 2019, 12 pages.
Russian Office Action dated Mar. 2, 2021, in Russian Patent Application No. 2019119938, inventors Mohr, P., et al., filed Dec. 19, 2017, 12 pages (with English Translation).
Co-pending, U.S. Appl. No. 17/250,162, inventors Mohr, P., et al., International Filing Date: Jun. 19, 2019 (Not yet Published).
Co-pending Application, U.S. Appl. No. 17/250,163, inventors Mohr, P., et al., International Filing Date: Jun. 19, 2019 (Not yet Published).
Kharkevich, D. A., ed., "Pharmacology," 10th Revised and Extended Edition, Textbook, pp. 72-73, Geotar-Media, Russia (2010).
Voloshinets, V.A., "Effect of alkyl substituents on the reactivity of alkyl acrylic monomers in radical copolymerization," The Sixth All-Russian Kargin Conference: "Polymers—2014," vol. 11, Collection of theses of poster presentations in 2 parts. Part one, Moscow, Jan. 27 Jan. 31, 2014, p. 334 (Jan. 2014).
Office Action dated Nov. 20, 2018, in U.S. Appl. No. 15/847,360, Inventor Mohr, Patrick et al., filed Dec. 19, 2017, 8 pages.

* cited by examiner

TRANSDERMAL THERAPEUTIC SYSTEM CONTAINING ASENAPINE AND POLYSILOXANE OR POLYISOBUTYLENE

TECHNICAL FIELD OF THE INVENTION

The present invention relates to a transdermal therapeutic system (TTS) for the transdermal administration of asenapine to the systemic circulation, and processes of manufacture, method of treatments and uses thereof.

BACKGROUND OF THE INVENTION

The active agent asenapine (3aRS,12bRS)-rel-5-chloro-2,3,3a,12b-tetrahydro-2-methyl-1H-dibenz[2,3:6,7]oxepino[4,5-c]pyrrole) is an atypical antipsychotic belonging to the dibenzo-oxepino pyrrole family, the tetracyclic structure of which is unrelated to those of other antipsychotics such as Olanzapine, Quetiapine or Clozapine (tricyclic structure), Risperidone, Ziprasidone or Aripiprazole (bicyclic structure). Asenapine is an antagonist at the dopamine D2 and serotonin 5-HT2A receptors with high affinity to the latter and has been developed by Schering-Plough/Organon for the treatment of schizophrenia and acute mania associated with bipolar disorder.

Currently, asenapine is commercially available in the form of sublingual tablets, which is administered in dosage strengths of 5 mg or 10 mg twice daily (BID) under the brand names Sycrest (Swissmedic) and Saphris (Schering-Plough).

The sublingual administration route avoids the first-pass metabolism of an oral administration in order to increase bioavailability, which is at 35% when taken sublingually and <2% if ingested. However, sublingual administration is associated with bitter or unpleasant taste as well as tongue/oral mucosal numbness induced by a local anesthetic effect, nausea and headaches. Further, eating, drinking and smoking are not allowed immediately after sublingual dosing for 10 min. These inconveniences may lead to reduced patient compliance and improper administration such as dose reduction, dose skipping, irregular drug intake or a complete abstinence from the intended asenapine intake. Sublingual administration is also difficult to monitor in institutionalized psychiatric patients and may not be suitable for children, elderly and other patients with difficulty in swallowing, or for those not capable of taking medication on their own.

The disadvantages of sublingual administration could be avoided by transdermal administration of asenapine. In this regard, passive transport of asenapine would be desirable. Passive transport of active agents from a transdermal therapeutic system (TTS) through the skin makes use of the driving force based on the concentration gradient between the concentration of active agent in the transdermal system and on the outer surface of the skin and the concentration in the blood stream. Such passive transport is advantageous in view of complexity of the TTS and the convenience of administration compared to TTS making use of active transportation such as iontophoresis or microporation.

Transdermal delivery of asenapine has been investigated, hut it appears that passive transdermal delivery of asenapine is challenging, e.g., in terms of the active ingredient utilization. Furthermore, transdermal delivery of asenapine may be accompanied by skin irritation problems. Up to date, no commercial asenapine TTS is available.

Thus, there is thus a need in the art for a transdermal therapeutic system for the transdermal administration of asenapine.

OBJECTS AND SUMMARY OF THE INVENTION

It is an object of the present invention to provide a TTS overcoming the above-mentioned disadvantages of current asenapine administration.

Thus, it is an object of the present invention to provide a TTS, and in particular a matrix-type TTS, for the transdermal administration of asenapine providing a permeation rate which is sufficient for achieving a therapeutically effective dose.

It is a further object of the present invention to provide a TTS, and in particular a matrix-type TTS, for the transdermal administration of asenapine providing therapeutically effective amounts of asenapine for at least 20 hours, preferably at least 1 day, during an administration period to the skin of the patient for at least 20 hours, preferably at least 1 day.

It is a further object of certain embodiments of the present invention to provide a TTS, and in particular a matrix-type TTS, for the transdermal administration of asenapine, wherein therapeutically effective amounts of asenapine are provided for 1 day by said transdermal therapeutic system during an administration period to the skin of the patient of 1 day, allowing a once a day exchange of the TTS in an around the clock treatment.

It is a further object the present invention to provide a TTS, and in particular a matrix-type TTS, for the transdermal administration of asenapine, wherein the fluctuation in asenapine blood plasma concentration is reduced when compared to sublingual administration, in particular in steady state.

It is another object of the present invention to provide a TTS, and in particular a matrix-type TTS, for the transdermal administration of asenapine with an improved bioavailability of asenapine.

It is a further object of the present invention to provide a TTS, and in particular a matrix-type TTS, for the transdermal administration of asenapine with a high active ingredient utilization.

It is another object of the present invention to provide a TTS, in particular a matrix-type TTS, for the transdermal administration of asenapine without causing significant skin irritation problems.

It is another object of the present invention to provide a TTS, and in particular a matrix-type TTS, for the transdermal administration of asenapine which complies with the needs of a convenient application in view of size and thickness and/or which is easy and cost-efficient to manufacture.

These objects and others are accomplished by the present invention, which according to a first aspect relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing layer comprising:
1. asenapine in the form of the free base; and
2. a polymer selected from the group consisting of polysiloxanes and polyisobutylenes in an amount of more than 50% by weight based on the total weight of the asenapine-containing layer;

and

C) optionally an additional skin contact layer.

In a preferred embodiment, the amount of the polymer ranges from 55 to 98%, preferably from 70 to 98% or from 80 to 98% by weight, more preferably from 92 to 98% by weight based on the total weight of the asenapine-containing layer. In a further preferred embodiment, the polymer is a polysiloxane.

In preferred embodiment, the present invention relates to a transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      1. asenapine in the form of the free base; and
      2. a polysiloxane in an amount of from 92 to 98% by weight based on the total weight of the asenapine-containing layer;
and
   C) optionally an additional skin contact layer.

In a preferred embodiment, the asenapine-containing layer further comprises at least one excipient selected from the group consisting of crystallization inhibitors, solubilizers, fillers, substances for skincare, pH regulators, preservatives, tackifiers, softeners, stabilizers, and permeation enhancers. Preferably, the asenapine-containing layer comprises a stabilizer in an amount of 0.01 to 1.0% by weight based on the total weight of the asenapine-containing layer, and/or a crystallization inhibitor in an amount of 0.5 to 10% by weight based on the total weight of the asenapine-containing layer.

According to certain embodiments of the invention, the transdermal therapeutic system according to the invention is for use in a method of treatment, in particular for use in a method of treating schizophrenia and/or bipolar disorder.

Thus, according to certain embodiments of the invention, the transdermal therapeutic system according to the invention is for use in a method of treating schizophrenia and/or bipolar disorder wherein the transdermal therapeutic system according to the invention is applied to the skin of the patient for a dosing interval of from 20 to 30 hours, preferably of about 24 hours.

According to other embodiments, the present invention relates to a method of treatment, in particular to a method of treating schizophrenia and/or bipolar disorder, including applying a transdermal therapeutic system according to the invention to the skin of a patient.

According to certain other embodiments of the invention, the transdermal therapeutic system according to the invention is for use in a method of treating psychosis in general, and in particular for use in a method of treating one or more conditions selected from schizophrenia, bipolar disorder, posttraumatic stress disorder, major depressive disorder, dementia related psychosis, agitation and manic disorder, in particular during administration for an extended period of time, e.g. during an administration period of from 20 to 30 hours, preferably about 24 h. Such modes of administration preferably require once a day exchange of the TTS in an around-the-clock treatment, i.e. a dosing interval of about 24 hours.

Thus, according to certain other embodiments, the invention relates to a method of treating schizophrenia and/or bipolar disorder, wherein the transdermal therapeutic system according to the invention is applied to the skin of the patient for a dosing interval of from 20 to 30 hours, preferably of about 24 hours.

According to certain other embodiments of the invention, the present invention relates to a method of treating psychosis in general, and in particular to a method of treating one or more conditions selected from schizophrenia, bipolar disorder, posttraumatic stress disorder, major depressive disorder, dementia related psychosis, agitation and manic disorder, in particular during administration for an extended period of time, e.g. during an administration period of from 20 to 30 hours, preferably of about 24 hours. Such modes of administration preferably require a once a day exchange of the TTS in an around-the-clock treatment, i.e. a dosing interval of about 24 hours.

Furthermore, the present invention relates to a process for manufacturing an asenapine-containing layer for use in a transdermal therapeutic system according to the invention comprising the steps of:
   1) combining at least the components
      1. asenapine in the form of asenapine base;
      2. a polymer selected from the group consisting of polysiloxanes and polyisobutylenes in an amount of more than 50% by weight based on the total weight of the asenapine-containing layer; and
      3. optionally at least one additive;
      to obtain a coating composition;
   2) coating the coating composition onto the backing layer or release liner or any intermediate liner; and
   3) drying the coated coating composition to form the asenapine-containing layer.

The preferred embodiments regarding the transdermal therapeutic system of the invention described above and hereinafter are also relevant in the context of the above defined process of the invention.

According to certain embodiments, the invention also relates to a transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing matrix layer comprising:
      1. asenapine in the form of the free base;
      2. a polysiloxane in an amount of at least 50% by weight based on the total weight of the asenapine-containing layer; and
      3. a stabilizer; and
      4. a crystallization inhibitor;
and
   C) optionally an additional skin contact layer.

According to certain embodiments, the invention also relates to a transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing matrix layer comprising:
      1. asenapine in the form of the free base in an amount of 2 to 7% by weight based on the total weight of the asenapine-containing layer;
      2. a polysiloxane in an amount of from 85 to 98% by weight based on the total weight of the asenapine-containing layer; and
      3. a stabilizer in an amount of from 0.01 to 1.0% by weight based on the total weight of the asenapine-containing layer; and 4. a crystallization inhibitor in an amount of from 0.5 to 10% by weight based on the total weight of the asenapine-containing layer;
and
C) optionally an additional skin contact layer.
wherein the area weight of the matrix layer ranges from 70 to 100 g/m².

In a preferred embodiment, the asenapine-containing matrix layer comprises:
1. asenapine in the form of the free base in an amount of 2 to 7% by weight based on the total weight of the asenapine-containing matrix layer;
2. a polysiloxane in an amount of from 92 to 98% by weight based on the total weight of the asenapine-containing layer;
3. a stabilizer in an amount of from 0.01 to 1.0% by weight based on the total weight of the asenapine-containing layer; and/or
4. a crystallization inhibitor in an amount of from 0.5 to 10% by weight based on the total weight of the asenapine-containing layer.

According to certain preferred embodiments, the invention also relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing matrix layer comprising:
1. asenapine in the form of the free base;
2. a polysiloxane in an amount of at least 50% by weight based on the total weight of the asenapine-containing layer; and
3. tocopherol; and
4. polyvinylpyrrolidone;
and
C) optionally an additional skin contact layer.

According to certain embodiments the invention also relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing matrix layer comprising:
1. asenapine in the form of the free base in an amount of 2 to 7% by weight based on the total weight of the asenapine-containing layer;
2. a polysiloxane in an amount of from 85 to 98% by weight based on the total weight of the asenapine-containing layer; and
3. tocopherol in an amount of from 0.01 to 1.0% by weight based on the total weight of the asenapine-containing layer; and
4. polyvinylpyrrolidone in an amount of from 0.5 to 10% by weight based on the total weight of the asenapine-containing layer;
and
C) optionally an additional skin contact layer;
wherein the area weight of the matrix layer ranges from 70 to 100 g/m².

In a preferred embodiment, the asenapine-containing matrix layer comprises:
1. asenapine in the form of the free base in an amount of 2 to 7% by weight based on the total weight of the asenapine-containing matrix layer;
2. a polysiloxane in an amount of 92 to 98% by weight based on the total weight of the asenapine-containing matrix layer;
3. tocopherol in an amount of 0.01 to 1.0% by weight based on the total weight of the asenapine-containing matrix layer; and/or
4. polyvinylpyrrolidone in an amount of 0.5 to 10% by weight based on the total weight of the asenapine-containing matrix layer;
wherein the area weight of the matrix layer ranges from 70 to 100 g/m².

According to a second aspect, the present invention relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing layer comprising:
1. asenapine in an amount of from 2 to 7% by weight based on the total weight of the asenapine-containing layer; and
2. at least one silicone polymer in an amount of from 85 to 98% by weight based on the total weight of the asenapine-containing layer;
and
C) optionally an additional skin contact layer.

It is to understood that the amount provided for the at least silicone polymer refers to the total amount of the at least one silicone polymer, i.e. the total amount of the one or more silicone polymers. For example, if two silicone polymers are present in the asenapine-containing layer, the amount of from 85 to 98% by weight refers to the total amount of the two silicone polymers.

In a preferred embodiment of this second aspect, the present invention relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing matrix layer comprising:
1. asenapine in an amount of 2 to 7% by weight based on the total weight of the asenapine-containing layer;
2. at least one silicone polymer in an amount of from 85 to 98% by weight based on the total weight of the asenapine-containing layer; and
3. a stabilizer in an amount of from 0.01 to 1.0% by weight based on the total weight of the asenapine-containing layer; and
4. a crystallization inhibitor in an amount of from 0.5 to 10% by weight based on the total weight of the asenapine-containing layer;
and
C) optionally an additional skin contact layer.

As indicated above, the amount of the at least one silicone polymer is the total amount of silicone polymer(s) contained in the asenapine-containing layer. Preferences regarding the area weight, the stabilizer, the crystallization inhibitor, the asenapine and the silicone polymer will be provided further below. For example, it is preferred that the area weight of the asenapine-containing layer ranges from 50 to 120 g/m², more preferably from 70 to 100 g/m². Further, it is preferred that the stabilizer is tocopherol, ascorbyl palmitate, or a combination thereof, and the crystallization inhibitor is polyvinylpyrrolidone. Furthermore, it is preferred that the asenapine is in the form of the free base. Moreover, the silicone polymer is preferably obtainable by polycondensation of silanol endblocked polydimethylsiloxane with a silicate resin. More preferably, the ratio of the silanol endblocked polydimethylsiloxane to the silicate resin is in the range of from 70:30 to 50:50, preferably from 56:44 to 54:46, e.g. about 55:45. Particularly preferably, the residual functionality of the at least one silicone polymer is capped with trimethylsiloxy groups. This provides amine compatibility of the silicone polymer.

In another preferred embodiment of the second aspect of the invention and its preferred embodiments defined above, the present invention relates to a transdermal therapeutic system as defined above for use in a method of treating a human patient, preferably for use in a method of treating bipolar disorder and/or schizophrenia, in particular acute manic or mixed episodes of bipolar disorder. Preferably, the transdermal therapeutic system is applied to the skin of the patient for a dosing interval of from 20 to 30 hours, preferably about 24 hours.

The present invention also relates to a process for manufacturing an asenapine-containing layer for use in a transdermal therapeutic system according to the second aspect of the invention comprising the steps of:
1) combining at least the components
   1. asenapine in an amount of from 2 to 7% by weight based on the total weight of the asenapine-containing layer;
   2. at least one silicone polymer in an amount of from 85 to 98% by weight based on the total weight of the asenapine-containing layer;
   3. optionally a stabilizer; and
   4. optionally a crystallization inhibitor;
   to obtain a coating composition;
2) coating the coating composition onto the hacking layer or release liner or any intermediate liner; and
3) drying the coated coating composition to form the asenapine-containing layer.

The above defined preferences of the transdermal therapeutic system according to the second aspect of the invention also apply to the above process of the invention.

According to a third aspect, the present invention relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing layer comprising:
   1. asenapine in an amount of from 2 to 15% by weight based on the total weight of the asenapine-containing layer; and
   2. at least one polyisobutylene in an amount of from 70 to 98% by weight based on the total weight of the asenapine-containing layer;
and
C) optionally an additional skin contact layer.

It is to be understood that the amount provided for the at least polyisobutylene refers to the total amount of the at least one polyisobutylene, i.e. the total amount of the one or more polyisobutylenes. For example, if two polyisobutylenes are present in the asenapine-containing layer, which is preferred according to the invention, the amount of from 85 to 98% by weight refers to the total amount of the two polyisobutylenes.

In a preferred embodiment of this third aspect, the present invention relates to a transdermal therapeutic system for the transdermal administration of asenapine comprising a self-adhesive layer structure comprising a therapeutically effective amount of asenapine, said self-adhesive layer structure comprising:
A) a backing layer;
B) an asenapine-containing matrix layer comprising:
   1. asenapine in an amount of from 2 to 15% by weight based on the total weight of the asenapine-containing layer; and
   2. at least one polyisobutylene in an amount of from 70 to 98% by weight based on the total weight of the asenapine-containing layer; and
   3. a hydrophilic polymer in an amount of from 1 to 20% by weight based on the total weight of the asenapine-containing layer;
and
C) optionally an additional skin contact layer.

As indicated above, the amount of the at least one polyisobutylene is the total amount of polyisobutylene(s) contained in the asenapine-containing layer. Preferences regarding the area weight, the hydrophilic polymer, the asenapine and the polyisobutylene will be provided further below. For example, it is preferred that the area weight of the asenapine-containing layer ranges from 40 to 250 g/m². The hydrophilic polymer allows that the TTS takes up water, which is advantageous for the skin permeation properties. Preferably, the hydrophilic polymer is polyvinylpyrrolidone. Furthermore, it is preferred that the asenapine is in the form of the free base. The amount of asenapine is preferably in the range of from 4 to 12% by weight, preferably from 6 to 10% by weight based on the total weight of the asenapine-containing layer. Moreover, it is preferred that the at least one polyisobutylene is a combination of a low molecular weight polyisobutylene and a high molecular weight polyisobutylene in a ratio of from 99:1 to 50:50, preferably from 90:10 to 60:40, more preferably from 85:15 to 70:30. Particularly preferably, the low molecular weight polyisobutylene has a viscosity average molecular weight of from 38,000 to 42,000 g/mol and/or a weight average molecular weight of from 34,000 to 40,000 g/mol, and the high molecular weight polyisobutylene has a viscosity average molecular weight of from 1,100,000 to 1,120,000 g/mol and/or a weight average molecular weight of from 1,540,000 to 1,560,000 g/mol. The amount of the at least one polyisobutylene is preferably from 70 to 90% by weight, based on the total weight of the asenapine-containing layer.

In another preferred embodiment of the third aspect of the invention and its preferred embodiments defined above, the present invention relates to a transdermal therapeutic system as defined above for use in a method of treating a human patient, preferably for use in a method of treating bipolar disorder and/or schizophrenia, in particular acute manic or mixed episodes of bipolar disorder. In one preferred embodiment, the transdermal therapeutic system is applied to the skin of the patient for a dosing interval of from 20 to 30 hours, preferably about 24 hours. In this context, the asenapine-containing layer of the transdermal therapeutic system preferably has an area weight of from 40 to 125 g/m², more preferably from 60 to 100 g/m². In another preferred embodiment, the transdermal therapeutic system is applied to the skin of the patient for a dosing interval of at least 72 hours, preferably about 84 hours. In this context, the asenapine-containing layer of the transdermal therapeutic system preferably has an area weight of from more than 125 to 250 g/m², more preferably from 150 to 250 g/m². It has surprisingly been found by the inventors of the present invention that depending on the area weight of the TTS, it may be suitable for use in different dosing intervals with the preferences indicated above.

The present invention also relates to a process for manufacturing an asenapine-containing layer for use in a transdermal therapeutic system according to the third aspect of the invention comprising the steps of:
1) combining at least the components
   1. asenapine in an amount of from 2 to 15% by weight based on the total weight of the asenapine-containing layer;
   2. at least one polyisobutylene in an amount of from 70 to 98% by weight based on the total weight of the asenapine-containing layer; and
   3. optionally a hydrophilic polymer;
   to obtain a coating composition;
2) coating the coating composition onto the backing layer or release liner or any intermediate liner; and
3) drying the coated coating composition to form the asenapine-containing layer.

The above defined preferences of the transdermal therapeutic system according to the third aspect of the invention also apply to the above process of the invention.

Within the meaning of this invention, the term "transdermal therapeutic system" (TTS) refers to a system by which the active agent (asenapine) is administered to the systemic circulation via transdermal delivery and refers to the entire individual dosing unit that is applied to the skin of a patient, and which comprises a therapeutically effective amount of asenapine in a self-adhesive layer structure and optionally an additional adhesive overlay on top of the asenapine-containing self-adhesive layer structure. The self-adhesive layer structure may be located on a release liner (a detachable protective layer), thus, the TTS may further comprise a release liner. Within the meaning of this invention, the term "TTS" in particular refers to a system providing passive transdermal delivery excluding active transport as in methods including iontophoresis or microporation.

Within the meaning of this invention, the term "asenapine-containing self-adhesive layer structure" or "self-adhesive layer structure comprising a therapeutically effective amount of asenapine" refers to the active agent-containing structure providing the area of release for asenapine during administration. The adhesive overlay adds to the overall size of the TTS, but does not add to the area of release. The asenapine-containing self-adhesive layer structure comprises a backing layer, at least one asenapine-containing layer, and optionally at least one additional skin contact layer.

Within the meaning of this invention, the term "therapeutically effective amount" refers to a quantity of active agent in the TTS sufficient to provide, if administered by the TTS to a patient, asenapine blood levels of a similar range (i.e. of about 10% to about 1000% as measured as an AUC) when compared to blood levels obtained in steady state administration of twice daily 5 mg sublingual asenapine over a predefined extended period of time (e.g. 1, 3.5 and 7 days). A TTS usually contains more active in the system than is in fact provided to the skin and the systemic circulation. This excess amount of active agent is usually necessary to provide enough driving force for the passive transportation from the TTS to the systemic circulation. However, it is preferred according to the invention that the TTS provides a high active ingredient utilization.

Within the meaning of this invention, the terms "active", "active agent", and the like, as well as the term "asenapine" refer to asenapine in any pharmaceutically acceptable chemical and morphological form and physical state. These forms generally include asenapine in its free base form, protonated or partially protonated asenapine, asenapine salts and in particular acid addition salts formed by addition of an inorganic or organic acid such as asenapine hydrochloride or asenapine maleate, hydrates, complexes and so on, as well as asenapine in the form of particles which may be micronized, crystalline and/or amorphous, and any mixtures of the aforementioned forms. The asenapine, where contained in a medium such as a solvent, may be dissolved or dispersed or in part dissolved and in part dispersed.

Within the meaning of this invention, the term "asenapine in form of the free base" refers to asenapine in any pharmaceutically acceptable chemical and morphological form and physical state. Preferably, the term does not include asenapine in the form of asenapine salts. In particular, the term does not include asenapine in protonated form or in the form of asenapine salts.

Unless otherwise indicated, in particular the amount of asenapine in the self-adhesive layer structure relates to the amount of asenapine included in the TTS during manufacture of the TTS and is calculated based on asenapine in the form of the free base. For example, when a) 0.1 mmol (equal to 28.6 mg) asenapine base or b) 0.1 mmol (equal to 40.2 mg) asenapine maleate is included in the TTS during manufacture, the amount of asenapine in the self-adhesive layer structure is, within the meaning of the invention, in both cases 0.1 mmol or 28.6 mg.

The asenapine starting material included in the TTS during manufacture of the TTS may be in the form of particles. Asenapine may preferably be present in the self-adhesive layer structure in the form of particles.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. asenapine) is not totally dissolved. Dispersing in the sense of the invention comprises the dissolution of a part of the starting material (e.g. asenapine particles), depending on the solubility of the starting material (e.g. the solubility of asenapine in the coating composition).

There are two main types of TTS using passive active agent delivery, i.e. matrix-type TTS and reservoir-type TTS. In matrix-type TTS the active agent is included in a matrix, while in a reservoir-type TTS the active agent is included in a liquid or semi-liquid reservoir.

Within the meaning of this invention, "matrix-type TTS" refers to a system or structure, wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. Accordingly, the asenapine-containing layer may in one embodiment be an asenapine-containing matrix layer, wherein preferably the asenapine is homogeneously distributed within a polymer matrix. Furthermore, the asenapine-containing matrix layer may optionally comprise a rate-controlling membrane, so as to control the release of the active agent from the TTS. Furthermore, in certain embodiments, the asenapine-containing matrix layer may comprise two matrix layers, which may be laminated together or which may be separated by a rate-controlling membrane controlling the release of the active agent. Thus, the term asenapine-containing matrix layer covers both monolayer and multilayer systems, optionally comprising a rate-controlling membrane. Preferably, the asenapine-containing matrix layer is a monolayer comprising the active agent homogeneously dissolved and/or dispersed within a polymer matrix. The release of the active agent in a matrix-type TTS is mainly controlled by the matrix including the active agent itself. Matrix-type TTS are advantageous in that, compared to reservoir type TTS, usually no rate controlling membranes are necessary and no dose dumping can occur due to membrane rupture. In summary, matrix-type transdermal therapeutic systems (TTS) are typically less complex in manufacture and easy and convenient to use by patients.

TTS with an active agent-containing reservoir are referred to by the term "reservoir-type TTS". In such a system, the release of the active agent is often controlled by a rate-controlling membrane. Accordingly, the asenapine-containing layer may in one embodiment be an asenapine-containing reservoir layer, which preferably comprises a liquid or semi-liquid reservoir comprising the asenapine, and a polymer layer, wherein the reservoir and the polymer layer may optionally be separated by a rate-controlling membrane. In the reservoir, the asenapine is preferably dissolved in a solvent such as ethanol or water or in silicone oil. The polymer layer preferably serves as skin contact layer and has adhesive properties. Reservoir-type TTS are not to be understood as being of matrix-type within the meaning of the invention. In particular, within the meaning of this invention, microreservoir-systems (biphasic systems having an inner active-containing phase in an outer matrix-phase), considered in the art to be a mixture between a matrix-type TTS and a reservoir-type TTS, are considered to be of matrix-type within the meaning of the invention. Matrix-type TTS may in particular be in the form of a "drug-in-adhesive"-type TTS referring to a system wherein the active is homogeneously dissolved and/or dispersed within a pressure-sensitive adhesive matrix.

Within the meaning of this invention, the term "asenapine-containing layer" refers to any monolayer or multilayer system containing the active agent and a polymer. The term covers asenapine-containing matrix layers and asenapine-containing reservoir layers. If the asenapine-containing layer is an asenapine-containing matrix layer, said layer is preferably present in a matrix-type TTS, and the asenapine is homogeneously dissolved and/or dispersed within a polymer matrix. If the polymer is a pressure-sensitive adhesive, the matrix layer may also represent the skin contact layer, i.e. the adhesive layer, of the TTS. Alternatively, an additional skin contact layer may be present as adhesive layer, wherein said additional skin contact layer is typically active agent-free. The skin contact layer may be present on the asenapine-containing matrix layer or separated from the asenapine-containing matrix layer by a rate-controlling membrane. Preferably, the asenapine-containing matrix layer has sufficient adhesive properties, so that it also represents the skin contact layer and no additional skin contact layer is present. If the asenapine-containing layer is an asenapine-containing reservoir layer, said layer is typically present in a reservoir-type TTS, and the layer comprises the asenapine in a reservoir and a polymer layer. Optionally, a rate-controlling membrane separates the reservoir from the polymer layer. The polymer layer typically serves as skin contact layer of the TTS. The polymer layer is typically active agent-free. Alternatively, an additional skin contact layer may be present as adhesive layer. The skin contact layer is typically active agent-free. Adhesive properties of reservoir-type TTS may also be obtained with an asenapine-containing reservoir layer comprising a structure with a peripheral adhesive, wherein the reservoir and optionally the rate-controlling membrane are applied onto an adhesive layer having a larger area and diameter than the reservoir and the membrane such that the protruding adhesive layer will provide the adhesive properties.

As used herein, the asenapine-containing layer is preferably an asenapine-containing matrix layer, and it is referred to the final, preferably solidified layer. Preferably, an asenapine-containing matrix layer is obtained after coating and drying the solvent-containing coating composition as described herein. The asenapine-containing matrix layer may also be manufactured by laminating two or more such solidified layers (e.g. dried layers) of the same composition to provide the desired area weight. The matrix layer may be self-adhesive (in the form of a pressure sensitive adhesive matrix) or the TTS may comprise an additional skin contact layer of a pressure sensitive adhesive for providing sufficient tack. Preferably, the matrix layer is a pressure sensitive adhesive matrix.

Within the meaning of this invention, the term "pressure-sensitive adhesive" refers to a material that in particular adheres with finger pressure, is permanently tacky, exerts a strong holding force and should be removable from smooth surfaces without leaving a residue. Examples of useful pressure-sensitive adhesives comprising polysiloxanes which are commercially available include the standard BIO-PSA series (7-4400, 7-4500 and 7-4600 series), the amine compatible (endcapped) BIO-PSA series (7-4100, 7-4200 and 7-4300 series), the Soft Skin Adhesives series (7-9800) and the BIO-PSA Hot Melt Adhesive manufactured by Dow Coming. Preferred pressure-sensitive adhesives comprising polysiloxane are heptane-solvated pressure-sensitive adhesives including BIO-PSA 7-4201 and BIO-PSA 7-4301. Also polyisobutylenes may act as pressure-sensitive adhesives. Suitable polyisobutylenes according to the invention are available under the tradename Oppanol®. Combinations of high-molecular weight polyisobutylenes (B100/B80) and low-molecular weight polyisobutylenes (B10, B11, B12, B13) may also be used. A pressure-sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix or in the form of an additional layer, i.e. a pressure sensitive adhesive skin contact layer. An adhesive overlay may still be employed to advance adhesion.

Within the meaning of this invention, the term "skin contact layer" refers to a layer included in the TTS to be in direct contact with the skin of the patient during administration. When the TTS comprises a skin contact layer, the other layers do not contact the skin and do not necessarily have self-adhesive properties. The area of release is provided by the area of the asenapine-containing layer. A skin contact layer may be used to enhance adherence. The sizes of an additional skin contact layer and the asenapine-containing layer are usually coextensive and correspond to the area of release. Typically, if an additional skin contact layer is present, the skin contact layer is active agent-free.

Within the meaning of this invention, the term "area weight" refers to the dry weight of a specific layer, e.g. of the matrix layer, provided in g/m². The area weight values are subject to a tolerance of ±10%, preferably ±7.5%, due to manufacturing variability.

If not indicated otherwise "%" refers to weight-%.

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2,000, preferably above 5,000 and more preferably above 10,000 Dalton. Correspondingly, compounds with a molecular weight below 2,000, preferably below 5,000 or more preferably below 10,000 Dalton are usually referred to as oligomers.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer and an adhesive layer.

Within the meaning of this invention, the term "backing layer" refers to a layer which supports e.g. the asenapine-containing layer or forms the backing of the adhesive overlay. The least one backing layer of the TTS is preferably occlusive, i.e. substantially impermeable to the active agent contained in the layer during the period of storage and administration and thus prevents active loss or cross-contamination in accordance with regulatory requirements.

The TTS according to the present invention can be characterized by certain parameters as measured in an in vitro skin permeation test.

The in vitro permeation test is performed in a Franz diffusion cell, with human or animal skin and preferably with dermatomed split-thickness human skin with a thickness of 800 μm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylenglycol, PEG 400 so that a receptor medium may e.g. contain 60 vol-% phosphate buffer pH 5.5, 30 vol-% dipropylenglycol and 10 vol-% acetonitrile.

Where not otherwise indicated, the in vitro permeation test is performed with dermatomed split-thickness human skin with a thickness of 800 μm and an intact epidermis, and with phosphate buffer pH 5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in μg/cm² and relates to the amount of active permeated in a sample interval at certain elapsed time. E.g., in an in vitro permeation test as described above, wherein the amount of active permeated into the receptor medium has been measured, e.g., at hours 0, 2, 4, 8, 12 and 24, the "permeated amount" of active can be given e.g. for the sample interval from hour 8 to hour 12 and corresponds to the measurement at hour 12.

The permeated amount can also be given as a "cumulative permeated amount", corresponding to the cumulated amount of active permeated at a certain point in time. E.g., in an in vitro permeation test as described above, wherein the amount of active permeated into the receptor medium has been measured, e.g., at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in μg/cm²-hr (corresponding to μg/(cm²*h)) and is calculated from the permeated amount in said sample interval as measured by in vitro permeation test as described above in μg/cm², divided by the hours of said sample interval. E.g. the skin permeation rate in an in vitro permeation test as described above, wherein the amount of active permeated into the receptor medium has been measured, e.g., at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been measured, e.g., at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters "permeated amount" and "skin permeation rate" (as well as "cumulative permeated amount" and "cumulative skin permeation rate") refer to mean values calculated from 3 in vitro permeation test experiments.

The TTS according to the present invention can also be characterized by certain parameters as measured in an in vivo clinical study.

Within the meaning of this invention, the parameter "mean release rate" refers to the mean release rate in μg/hr, in mg/hr, in μg/day or in mg/day over the period of administration (e.g., 1 day) by which the active agent is released through the human skin into the systemic circulation and is based on the AUC obtained over said period of administration in a clinical study. The mean release rate is a parameter used to identify the dose or the strength of a TTS. Since, in contrast to e.g. intravenous or oral administration and (as also described above) a TTS usually contains more active in the system than is in fact provided to the skin and the systemic circulation, the amount of active contained in the TTS is not meaningful as a parameter for the dose. This is why for a TTS the dose or strength is usually characterized by the mean release rate, which describes more accurately the amount of active delivered to the subject over time.

For a continuous drug treatment, the frequency of drug administration is preferably kept sufficiently high so as to maintain a therapeutically effective blood plasma concentration. In other words, the interval between two dosage form administrations, also called dosing interval, needs to be adapted accordingly. Within the meaning of the present invention, the term "dosing interval" refers to the period of time between two consecutive TTS administrations, i.e. the interval between two consecutive points in time a TTS is applied to the skin of the patient. Once applied, the TTS is usually maintained on the skin of the patient for the entire dosing interval and only removed at the end of the dosing interval, at which time a new TTS is applied to the skin. E.g., if the dosing interval is 24 hours or 1 day, the TTS is applied to and maintained on the skin of the patient for 24 hours or 1 day. After 24 hours or 1 day, the TTS is removed from the skin and a new TTS is applied. Thus, a dosing interval of 24 hours or 1 day allows a once-a-day TTS exchange mode in an around-the-clock treatment.

Within the meaning of this invention, the term "extended period of time" relates to a period of at least 20 hours or at least 24 hours, preferably from 20 to 48 hours, more preferably from 20 to 30 hours, most preferably about 24 hours.

Within the meaning of this invention, the term "room temperature" refers to the unmodified temperature found indoors in the laboratory where the experiments are conducted and usually lies within 15 to 35° C., and is preferably from 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention the term "pharmacokinetic parameters" refers to parameters describing the blood plasma curve, e.g. $C_{max}$, $C_t$ and $AUC_{t1-t2}$ obtained in a clinical study, e.g. by single-dose, multi-dose or steady state administration of the active agent TTS, e.g. the asenapine TTS, to healthy human subjects. The pharmacokinetic parameters of the individual subjects are summarized using arithmetic and geometric means, e.g. a mean $C_{max}$, a mean AUCt and a mean $AUC_{INF}$, and additional statistics such as the respective standard deviations and standard errors, the minimum value, the maximum value, and the middle value when the list of values is ranked (Median). In the context of the present invention, pharmacokinetic parameters, e.g. the $C_{max}$, $C_t$ and $AUC_{t1-t2}$ refer to arithmetic or geometric mean values and preferably refer to geometric mean values. It cannot be precluded that the absolute mean values obtained for a certain TTS in a clinical study vary to a certain extent from study to study. To allow a comparison of absolute mean values between studies, a reference formulation, e.g. in the future any product based on the invention, may be used as internal standard. A comparison of the AUC per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least ten individual healthy human subjects.

Within the meaning of this invention, the term "geometric mean" refers to the mean of the log transformed data back-transformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "$AUC_{t1-t2}$" is provided in (ng/ml) hr and relates to the area under the plasma concentration-time curve from hour t1 to t2 and is calculated by the linear trapezoidal method.

Within the meaning of this invention, the parameter "$C_{max}$" is provided in (ng/ml) and relates to the maximum observed blood plasma concentration of the active agent.

Within the meaning of this invention, the parameter "$C_t$" is provided in (ng/ml) and relates to the blood plasma concentration of the active agent observed at hour t.

Within the meaning of this invention, the parameter "$t_{max}$" is provided in hr and relates to the time point at which the $C_{max}$ value is reached. In other words, $t_{max}$ is the time point of the maximum observed plasma concentration.

Within the meaning of this invention, the term "mean plasma concentration" is provided in (ng/ml) and is a mean of the individual plasma concentrations of active agent, e.g. asenapine, at each point in time.

Within the meaning of this invention, the term "coating composition" refers to a composition comprising all components of the asenapine-containing layer, preferably the asenapine-containing matrix layer in a solvent, which may be coated onto the backing layer or release liner to form the active agent-containing layer upon drying.

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, heptane, in particular n-heptane, toluene and mixtures thereof.

Within the meaning of this invention, and unless otherwise specified, the term "about" refers to an amount that is ±10% of the disclosed amount. In some embodiments, the term "about" refers to an amount that is ±5% of the disclosed amount. In some embodiments, the term "about" refers to an amount that is ±2% of the disclosed amount.

DETAILED DESCRIPTION

TTS Structure

Figure 1:
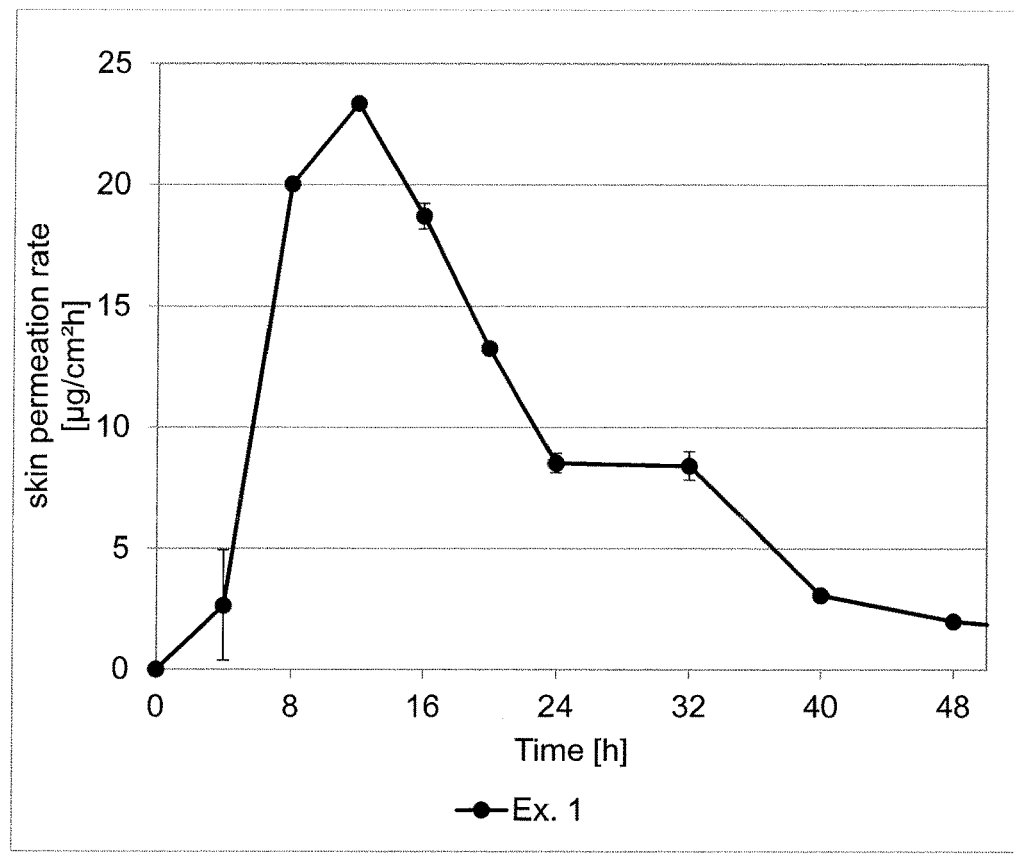
FIG. 1 depicts the asenapine skin permeation rate of TTS prepared according to Example 1.

The present invention relates to a transdermal therapeutic system for the transdermal administration of asenapine comprising a self-adhesive layer structure comprising a therapeutically effective amount of asenapine. Several aspects of the invention in this regard have been described above.

Preferably, the self-adhesive layer structure according to the present invention comprises A) a backing layer, and B) an asenapine-containing layer comprising 1. asenapine in the form of the free base and 2. a polymer selected from the group consisting of polysiloxanes and polyisobutylenes in an amount of more than 50% by weight based on the total weight of the asenapine-containing layer; and C) optionally an additional skin contact layer.

Thus, according to one embodiment of the invention, the transdermal therapeutic system for the transdermal administration of asenapine comprises a self-adhesive layer structure containing a therapeutically effective amount of asenapine, said self-adhesive layer structure comprising:
A) a backing layer;
B) an asenapine-containing layer comprising:
  1. asenapine in the form of the free base; and
  2. a polymer selected from the group consisting of polysiloxanes and polyisobutylenes in an amount of more than 50% by weight based on the total weight of the asenapine-containing layer;
and
C) optionally an additional skin contact layer.

In one embodiment, the backing layer is substantially asenapine-impermeable. Such a backing layer may also be referred to as occlusive backing layer.

The TTS according to the present invention may be a matrix-type TTS or a reservoir-type TTS, and preferably is a matrix-type TTS.

In a matrix-type TTS according to the invention, the asenapine is included in an asenapine-containing matrix layer. Thus, the asenapine-containing layer is preferably an asenapine-containing matrix layer as defined in detail above. The self-adhesive layer structure in such a matrix-type TTS can include one or more further layers such as an additional skin contact layer. Preferably, the skin contact layer is active agent-free. The skin contact layer and the asenapine-containing matrix layer may comprise the same polymer or different polymers. Any of the asenapine-containing matrix layer and the further layer(s) may be directly contacting each other or separated by a membrane such as a rate controlling membrane. If an asenapine-containing matrix layer is prepared by laminating two asenapine-containing matrix layers, which are of substantially the same composition, the resulting double layer is to be regarded as one matrix layer.

In a reservoir-type TTS according to the present invention, the asenapine is included in a liquid or semi-liquid reservoir. Thus, the asenapine-containing layer may also be an asenapine-containing reservoir layer comprising a reservoir comprising the asenapine and a polymer layer, wherein the reservoir and the polymer layer may optionally be separated from each other by a rate-controlling membrane. The self-adhesive layer structure in such a reservoir-type TTS can include one or more further layers such as an additional skin contact layer. Preferably, the skin contact layer is active agent-free. Any of the asenapine-containing reservoir layer and the further layer(s) may be directly contacting each other or separated by a membrane such as a rate controlling membrane.

In one specific embodiment, the self-adhesive layer structure according to the invention comprises an additional skin contact layer. The additional skin contact layer is self-adhesive and provides for adhesion between the self-adhesive layer structure and the skin of the patient during administration.

In another embodiment, the self-adhesive layer structure according to the invention does not comprise an additional skin contact layer. Sufficient adhesion between the self-adhesive layer structure and the skin of the patient during administration is then provided for by other means, e.g. by the asenapine-containing layer, preferably the asenapine-containing matrix layer. Alternatively, or additionally, an adhesive overlay may be used.

Thus, according to certain embodiments of the invention, the TTS may further comprise an adhesive overlay. This adhesive overlay is in particular larger than the asenapine-containing self-adhesive layer structure and is attached thereto for enhancing the adhesive properties of the overall transdermal therapeutic system. Said adhesive overlay comprises also a backing layer. The area of said adhesive overlay adds to the overall size of the TTS but does not add to the area of release. The adhesive overlay comprises a self-adhesive polymer or a self-adhesive polymer mixture selected from the group of acrylic polymers, polyisobutylenes, styrene-isoprene-styrene copolymers, polysiloxanes, and mixtures thereof, which may be identical to or different from any polymer or polymer mixture included in the active agent-containing self-adhesive layer structure.

The self-adhesive layer structure according to the invention is normally located on a detachable protective layer (release liner) from which it is removed immediately before application to the surface of the patient's skin. Thus, the TTS may further comprise a release liner. A TTS protected this way is usually stored in a blister pack or a seam-sealed pouch. The packaging may be child resistant and/or senior friendly.

Asenapine-Containing Layer

As outlined in more detail above, the TTS according to the present invention comprises a self-adhesive layer structure comprising an asenapine-containing layer.

In one embodiment, the asenapine-containing layer comprises:
1. asenapine in the form of the free base; and
2. a polymer selected from the group consisting of polysiloxanes and polyisobutylenes in an amount of more than 50% by weight based on the total weight of the asenapine-containing layer.

In one embodiment of the invention, the asenapine-containing layer is a matrix layer. In another embodiment, the asenapine-containing layer is a reservoir layer. It is preferred that the asenapine-containing layer is an asenapine-containing matrix layer.

In one embodiment of the invention, the asenapine-containing layer is obtainable by incorporating the asenapine in the form of the free base. As a result, the asenapine-containing layer of the TTS according to the invention typically comprises asenapine in the form of the free base. In addition, the asenapine may partly be present in protonated form. However, it is preferred that at least 50 mol %, preferably at least 75 mol % of the asenapine in the asenapine-containing layer are present in the form of the free base. In a particular preferred embodiment, at least 90 mol %, preferably at least 95 mol %, more preferably at least 99 mol % of the asenapine in the asenapine-containing layer are present in the form of the free base. Preferably, the asenapine-containing layer does not comprise asenapine maleate. In certain embodiments, the asenapine-containing layer is free of asenapine salts.

In one embodiment of the invention, the amount of asenapine in the asenapine-containing layer ranges from 1 to 10% by weight, preferably from 2 to 7% by weight based on the total weight of the asenapine-containing layer.

In one embodiment of the invention, the amount of asenapine in the asenapine-containing layer ranges from 3 to 21 mg, preferably from 3.5 to 14 mg.

In one embodiment, the polymer in the asenapine-containing layer is selected from the group consisting of polysiloxanes and polyisobutylenes. Preferably, the polymer in the asenapine-containing layer is a polysiloxane. In certain embodiments of the invention, the polymer is a pressure-sensitive adhesive polymer. In this case, the asenapine-containing layer is preferably a matrix layer, which has adhesive properties, so that no additional skin contact layer is required. The matrix layer composition may comprise a second polymer or may comprise two or more further polymers.

In one embodiment of the invention, the amount of the polymer, which is selected from the group consisting of polysiloxanes and polyisobutylene, is from 55 to 98%, preferably from 70 to 98% or from 80 to 98% by weight based on the total weight of the asenapine-containing layer. In a preferred embodiment of the invention, the asenapine-containing layer comprises the polymer, which is selected from the group consisting of polysiloxanes and polyisobutylenes, in an amount of from 80 to 96% by weight, preferably from 90 to 96% by weight. It is to be understood that also mixtures of polymers may be present in the asenapine-containing layer. Thus, in addition to a polymer selected from the group consisting of polysiloxanes and polyisobutylenes in an amount of more than 50% by weight based on the total weight of the asenapine-containing layer, a further polymer, e.g., an additional polysiloxane or polyisobutylene, an acrylic polymer or a styrene-isoprene-styrene copolymer, or a mixture thereof may be present. It is preferred that the asenapine-containing layer comprises at least 55%, preferably at least 70% by weight of a polysiloxane or polyisobutylene and optionally at least one additional polymer, which may be selected from other polymers including polysiloxanes, polyisobutylenes, acrylic polymers and styrene-isoprene-styrene copolymers. Particularly preferred is an asenapine-containing layer comprising a polysiloxane in an amount from 55 to 98%, preferably from 70 to 98% or from 80 to 98% by weight based on the total weight of the asenapine-containing layer. In an especially preferred embodiment of the invention, the asenapine-containing layer comprises a polysiloxane in an amount of from 80 to 96% by weight, preferably from 90 to 96% by weight.

Without wishing to be bound by theory, it is believed that the advantageous properties of the TTS according to the present invention, such as the good in vitro skin permeation, suitability for 24 hours dosing intervals as well as high active ingredient utilization are inter alia achieved by the fact that asenapine is present in the form of the free base and by the selection of the polymer in the asenapine-containing layer, which is selected from the group consisting of polysiloxanes and polyisobutylenes and is present in an amount of more than 50% by weight based on the total weight of the asenapine-containing layer. In particular, it has been found that it is advantageous if at least 90 mol % of the total amount of asenapine in the asenapine-containing layer is present in the form of the free base, and the asenapine-containing layer further comprises a polymer selected from the group consisting of polysiloxanes and polyisobutylenes in an amount of more than 50%, preferably at least 55%, more preferably at least 70% by weight based on the total weight of the asenapine-containing layer. Polysiloxanes are particularly advantageous for providing TTS suitable for 24 hours dosing intervals.

It has been found that it is not necessarily required that a peilneation enhancer is present in the asenapine-containing layer, but that nevertheless good in vitro skin permeation can be achieved. In one embodiment, the asenapine-containing therefore does not comprise a permeation enhancer. In one preferred embodiment, the asenapine-containing layer does not comprise isopropyl palmitate. In one preferred embodiment, the asenapine-containing layer does not comprise a permeation enhancer selected from oleic acids, oleic alcohols, and triglycerides. In another embodiment, the asenapine-containing layer does not comprise sodium acetate or sodium diacetate. In yet another embodiment, the asenapine-containing layer does not comprise a dicarboxylic acid alkali salt. In yet another embodiment, the asenapine-containing layer does not comprise a maleic acid alkali salt.

In certain embodiments of the invention, the area of release ranges from 5 to 60 cm$^2$, preferably from 10 to 40 cm$^2$. In certain preferred embodiments, the area of release is from 10 to 50 cm$^2$, e.g., from 10 to 25 cm$^2$ or from 25 to 50 cm$^2$. In certain particularly preferred embodiments, the area of release ranges is from 20 to 40 cm$^2$.

In certain embodiments of the invention, the area weight of the asenapine-containing layer ranges from 50 to 120 g/m$^2$, preferably from 70 to 100 g/m$^2$. In certain preferred embodiments, the area weight ranges from 75 to 85 g/m$^2$.

In another embodiment, the asenapine-containing layer comprises:
1. asenapine in an amount of from 2 to 7% by weight based on the total weight of the asenapine-containing layer; and
2. at least one silicone polymer in an amount of from 85 to 98% by weight based on the total weight of the asenapine-containing layer.

Preferably, the asenapine-containing layer is an asenapine-containing matrix-layer, which comprises 1. ascnapinc in an amount of 2 to 7% by weight based on the total weight of the asenapine-containing layer;
2. at least one silicone polymer in an amount of from 85 to 98% by weight based on the total weight of the asenapine-containing layer; and
3. a stabilizer in an amount of from 0.01 to 1.0% by weight based on the total weight of the asenapine-containing layer; and
4. a crystallization inhibitor in an amount of from 0.5 to 10% by weight based on the total weight of the asenapine-containing layer.

The area-weight of the asenapine-containing layer preferably ranges from 70 to 100 g/m². Preferably, the stabilizer is tocopherol, ascorbyl palmitate, or a combination thereof, and the crystallization inhibitor is polyvinylpyrrolidone. Furthermore, it is preferred that the asenapine is in the form of the free base. Moreover, the silicone polymer is preferably obtainable by polycondensation of silanol endblocked polydimethylsiloxane with a silicate resin. More preferably, the ratio of the silanol endblocked polydimethylsiloxane to the silicate resin is in the range of from 70:30 to 50:50, preferably from 56:44 to 54:46, e.g. about 55:45. Particularly preferably, the residual functionality of the at least one silicone polymer is capped with trimethylsiloxy groups. This provides amine compatibility of the silicone polymer.

In yet another embodiment, the asenapine-containing layer comprises
1. asenapine in an amount of from 2 to 15% by weight based on the total weight of the asenapine-containing layer; and
2. at least one polyisobutylene in an amount of from 70 to 98% by weight based on the total weight of the asenapine-containing layer;

Preferably, the asenapine-containing layer is an asenapine-containing matrix-layer, which comprises
1. asenapine in an amount of from 2 to 15% by weight based on the total weight of the asenapine-containing layer; and
2. at least one polyisobutylene in an amount of from 70 to 98% by weight based on the total weight of the asenapine-containing layer; and
3. a hydrophilic polymer in an amount of from 1 to 20% by weight based on the total weight of the asenapine-containing layer.

As indicated above, the amount of the at least one polyisobutylene is the total amount of polyisobutylene(s) contained in the asenapine-containing layer. The area weight of the asenapine-containing layer preferably ranges from 40 to 250 g/m², and is particularly preferably from 40 to 125 g/m² is a dosing interval of from 20 to 30 hours, preferably 24 hours is intended. Preferably, the hydrophilic polymer is polyvinylpyrrolidone. Furthermore, it is preferred that the asenapine is in the form of the free base. The amount of asenapine is preferably in the range of from 4 to 12% by weight, preferably from 6 to 10% by weight based on the total weight of the asenapine-containing layer. Moreover, it is preferred that the at least one polyisobutylene is a combination of a low molecular weight polyisobutylene and a high molecular weight polyisobutylene in a ratio of from 99:1 to 50:50, preferably from 90:10 to 60:40, more preferably from 85:15 to 70:30. Particularly preferably, the low molecular weight polyisobutylene has a viscosity average molecular weight of from 38,000 to 42,000 g/mol and/or a weight average molecular weight of from 34,000 to 40,000 g/mol, and the high molecular weight polyisobutylene has a viscosity average molecular weight of from 1,100,000 to 1,120,000 g/mol and/or a weight average molecular weight of from 1,540,000 to 1,560,000 g/mol. The amount of the at least one polyisobutylene, in particular the above combination of low and high molecular weight polyisobutylenes, is preferably from 70 to 90% by weight, based on the total weight of the asenapine-containing layer.

Asenapine

In accordance with the invention, the self-adhesive layer structure comprises asenapine, in particular in a therapeutically effective amount. Preferably, the therapeutically effective amount of asenapine is provided in the asenapine-containing layer of the self-adhesive layer structure, and is present in the form of the free base.

In one embodiment of the invention, the asenapine-containing layer is obtainable by incorporating the asenapine in the form of the free base.

In one embodiment of the invention, at least 50 mol %, preferably at least 75 mol % of the asenapine in the asenapine-containing layer are present in the form of the free base. In a particular preferred embodiment, at least 90 mol %, preferably at least 95 mol %, more preferably at least 99 mol % of the asenapine in the asenapine-containing layer are present in the form of the free base.

In one embodiment of the invention, at least 50 mol %, preferably at least 75 mol % of the total amount of asenapine in the TTS are present in the form of the free base. In a particular preferred embodiment, at least 90 mol %, preferably at least 95 mol %, more preferably at least 99 mol % of the total amount of asenapine in the TTS are present in the form of the free base.

In one embodiment, the asenapine-containing layer does not comprise asenapine maleate. In certain embodiments, the asenapine-containing layer is free of asenapine salts.

In one embodiment, the TTS of the invention does not comprise asenapine maleate.

The asenapine in the asenapine-containing layer may be present in the form of asenapine particles, preferably constituted of asenapine free base. The particles are preferably homogeneously distributed within the asenapine-containing layer.

As outlined above, the TTS of the invention provides for a high active ingredient utilization. Typically, a therapeutically effective amount of asenapine is released from the TTS over a dosing interval of 24 hours. Due to the high active ingredient utilization, a rather low amount of asenapine in the asenapine-containing layer is sufficient.

In certain embodiments, the amount of asenapine in the asenapine-containing layer ranges from 1 to 10%, preferably from 2 to 7% by weight based on the total weight of the asenapine-containing layer.

In certain embodiments, the amount of asenapine contained in the transdermal therapeutic system ranges from 3 to 21 mg, preferably from 3.5 to 14 mg.

In certain embodiments, the asenapine has a purity of at least 95%, preferably of at least 98% and more preferably of at least 99% as determined by quantitative HPLC. Quantitative HPLC may be performed with Reversed-Phase-HPLC with UV detection. In particular, the following conditions can be used if HPLC is performed isocratically:

Column: Octadecyl phase acc. Ph. Eur. 2.2.29 (USP phase L1) Kromasil C18 125 mm×4.0 mm; 5 µm or equivalent
Mobile phase: $KH_2PO_4$/Methanol/TEA (45:55:0.1; v:v:v); pH 2.5±0.05 (TEA=triethylamine)
Gradient: isocratic
Flux: 1.0 mL
Injection volume: 30 µL Column temperature: 40° C.
Wavelength: 225 nm, 270 nm and 3-D-field; Evaluation is performed at 270 nm
Run time: 10 min
Furthermore, the following conditions can be used if HPLC is performed with a gradient:
Column: Octadecyl phase acc. Ph. Eur. 2.2.29 (USP phase L1) Kinetex C18 EVO 100 mm×4.6 mm; 2.1 µm or equivalent
Mobile phase: A: 0.02 mol $KH_2PO_4$ Buffer/Methanol/TEA (70:30:0.1; v:v:v) adj. to pH 2.5
B: 0.02 mol $KH_2PO_4$ Buffer/Methanol/TEA (30:70:0.1; v:v:v); adj. to pH 2.5 (TEA=triethylamine)
Flux: 1.0 mL
Injection volume: 30 µL
Column temperature: 40° C.
Wavelength: 225 nm, 270 nm and 3-D-field; Evaluation is performed at 225 nm
Run time: 32 min
Gradient profile:

| | | |
|---|---|---|
| 0.00 min: | A: 100% | B: 0% |
| 12.00 min: | A: 40% | B: 60% |
| 18.00 min: | A: 0% | B: 100% |
| 27.00 min: | A: 0% | B: 100% |
| 27.01 min: | A: 100% | B: 0% |
| 32.00 min: | A: 100% | B: 0% |

Polymer

As outlined above, the TTS according to a specific embodiment of the present invention comprises a self-adhesive layer structure comprising an asenapine-containing layer comprising a polymer selected from the group consisting of polysiloxanes and polyisobutylenes in an amount of more than 50% by weight based on the total weight of the asenapine-containing layer. It has been found that the use of a polysiloxane or a polyisobutylene in the asenapine-containing layer is advantageous in terms of the active ingredient utilization and the permeation properties of the TTS. The resulting TTS according to the invention are particularly suitable for dosing intervals of 24 hours.

In certain embodiments, the polymer, i.e. the polysiloxane or the polyisobutylene, is a pressure-sensitive adhesive polymer, so that good adhesive properties are also obtained. This is particularly relevant, if the asenapine-containing layer is an asenapine-containing matrix layer, which is preferred according to the invention. Preferably, an additional skin contact layer is not required, if the asenapine-containing matrix layer comprises a polysiloxane or a polyisobutylene in an amount of more than 50% by weight, wherein said polysiloxane or polyisobutylene is a pressure-sensitive adhesive polymer. In this case, the TTS is preferably based on a monolayer structure with the asenapine-containing matrix layer as the only layer being present on the backing layer. The pressure-sensitive adhesive polymer provides for sufficient cohesion and adhesion of the matrix layer.

In certain embodiments of the invention, the polymer, which is selected from polysiloxanes and polyisobutylenes, is present in the asenapine-containing layer in an amount of at least 55%, preferably at least 70%, more preferably at least 80% by weight based on the total weight of the asenapine-containing layer. Preferably, the amount ranges from 55 to 98%, preferably from 70 to 98% or from 80 to 98% by weight based on the total weight of the asenapine-containing layer. In a preferred embodiment of the invention, the asenapine-containing layer comprises the polymer, which is selected from the group consisting of polysiloxanes and polyisobutylenes, in an amount of from 80 to 98% by weight, preferably from 90 to 98% by weight, more preferably from 92 to 98% by weight. If the polymer, which is present in the asenapine-containing layer in an amount as defined above, is selected from polysiloxanes, it is to be understood that also combinations of polysiloxanes are covered. Preferably, only one type of polysiloxane is present in the asenapine-containing layer. If the polymer, which is present in the asenapine-containing layer in an amount as defined above, is selected from polyisobutylenes, it is to be understood that also combinations of polyisobutylenes are covered. In one embodiment, only one type of polyisobutylene is present in the asenapine-containing layer. In another embodiment, a combination of two different types of polyisobutylenes is present in the asenapine-containing layer.

In addition, at least one further polymer may be present in the asenapine-containing layer. The at least one further polymer may be selected from polysiloxanes, polyisobutylenes, styrene-isoprene-styrene block copolymers and acrylic polymers. For example, the additional polymer may be an acrylic polymer.

In one embodiment, the polymer, which is present in the asenapine-containing layer in an amount of more than 50% by weight, is a polysiloxane or a combination of polysiloxanes. In a preferred embodiment, the polysiloxane or the combination of polysiloxanes is present in an amount of at least 55%, more preferably at least 70%, most preferably at least 80% by weight. In another preferred embodiment, the polysiloxane or the combination of polysiloxanes is present in an amount ranging from 55 to 98%, preferably from 70 to 98% or from 80 to 98% by weight based on the total weight of the asenapine-containing layer. Preferably, the asenapine-containing layer comprises only one polysiloxane in an amount of more than 50% by weight. In a preferred embodiment, the polysiloxane is present in an amount of at least 55%, more preferably at least 70%, most preferably at least 80% by weight. In another preferred embodiment, the polysiloxane is present in an amount ranging from 55 to 98%, preferably from 70 to 98% or from 80 to 98% by weight based on the total weight of the asenapine-containing layer. In an especially preferred embodiment of the invention, the asenapine-containing layer comprises the polysiloxane in an amount of from 80 to 98% by weight, preferably from 90 to 98% by weight, more preferably from 92 to 98% by weight. In certain embodiments, it is preferred that no additional polymer apart from the polysiloxane is present. In other embodiments, especially if the amount of the polysiloxane is in the range of, e.g., from 55 to 80% by weight based on the total weight of the asenapine-containing layer, an additional polymer selected from polyisobutylenes, styrene-isoprene-styrene block copolymers and acrylic polymers may be present in the asenapine-containing layer. It is then preferred that the total amount of all polymers in the asenapine-containing layer is from 80 to 98% by weight based on the total weight of the asenapine-containing layer.

In another embodiment, the polymer, which is present in the asenapine-containing layer in an amount of more than 50% by weight, is a polyisobutylene or a combination of polyisobutylenes. In a preferred embodiment, the polyisobutylene or the combination of polyisobutylenes is present in an amount of at least 55%, more preferably at least 70%, most preferably at least 80% by weight. In another preferred embodiment, the polyisobutylene or the combination of polyisobutylenes is present in an amount ranging from 55 to 98%, preferably from 70 to 98%, especially preferably from 70 to 90% by weight, based on the total weight of the asenapine-containing layer. In certain embodiments, it is preferred that no additional polymer apart from the polyisobutylene is present. In other embodiments, especially if the amount of the polyisobutylene or the combination of polyisobutylenes is in the range of, e.g., from 55 to 80% by weight based on the total weight of the asenapine-containing layer, an additional polymer selected from polysiloxanes, styrene-isoprene-styrene block copolymers and acrylic polymers may be present. It is then preferred that the total amount of all polymers in the asenapine-containing layer is from 80 to 98% by weight based on the total weight of the asenapine-containing layer.

Suitable polymers according to the invention are commercially available e.g. under the brand names BIO-PSAs (polysiloxanes), Oppanol™ (polyisobutylenes), JSR-SIS (a styrene-isoprene-styrene copolymer) or Duro-Tak™ (acrylic polymers).

The term "polysiloxane" as used herein refers to a polymer, which is based on a polysiloxane, and may also be referred to as silicone-based polymer, silicone polymer, or silicone. Pressure-sensitive polysiloxanes, i.e. pressure-sensitive adhesives based on polysiloxanes may also be referred to as silicone-based pressure-sensitive adhesives, or silicone pressure-sensitive adhesives. For the present invention, pressure-sensitive adhesive polysiloxanes are preferred. These pressure-sensitive adhesives provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure sensitive adhesives are based on a resin-in-polymer concept wherein, by condensation reaction of silanol end blocked polydimethylsiloxane with a silicate resin, a polysiloxane is prepared wherein for amine stability the residual silanol functionality is additionally capped with trimethylsiloxy groups. The silanol end blocked polydimethylsiloxane content contributes to the viscous component of the visco-elastic behavior, and impacts the wetting and the spreadability properties of the adhesive. The resin acts as a tackifying and reinforcing agent, and participates in the elastic component. The correct balance between dimethiconol and resin provides for the correct adhesive properties.

In view of the above, the silicone polymers of the invention (herein also referred to as "polysiloxanes") are generally obtainable by polycondensation of silanol endblocked polydimethylsiloxane with a silicate resin. Amine-compatible silicone polymers can be obtained by reacting the silicone polymer with trimethylsilyl (e.g. hexamethyldisilazane) in order to reduce the silanol content of the polymer. As a result, the residual silanol functionality is at least partly, preferably mostly or fully capped with trimethylsiloxy groups.

As indicated above, the tackiness of the silicone polymer may be modified by the resin-to-polymer ratio, i.e. the ratio of the silanol endblocked polydimethylsiloxane to the silicate resin, which is preferably in the range of from 70:30 to 50:50, preferably from 65:35 to 55:45. The tackiness will be increased with increasing amounts of the polymer relative to the resin. High tack silicone polymers preferably have a resin-to-polymer ratio of 55:45, medium tack silicone polymers preferably have a resin-to-polymer ratio of 60:40, and low tack silicone polymers preferably have a resin-to-polymer ratio of 65:35. High tack silicone polymers preferably have a complex viscosity at 0.01 rad/s and 30° C. of $5\times10^6$ Poise, medium tack silicone polymers preferably have a complex viscosity at 0.01 rad/s and 30° C. of $5\times10^7$ Poise, and low tack silicone polymers preferably have a complex viscosity at 0.01 rad/s and 30° C. of $5\times10^8$ Poise. High tack amine-compatible silicone polymers preferably have a complex viscosity at 0.01 rad/s and 30° C. of $5\times10^6$ Poise, medium tack amine-compatible silicone polymers preferably have a complex viscosity at 0.01 rad/s and 30° C. of $5\times10^8$ Poise, and low tack amine-compatible silicone polymers preferably have a complex viscosity at 0.01 rad/s and 30° C. of $5\times10^9$ Poise.

Examples of useful pressure-sensitive adhesives based on polysiloxane which are commercially available include the standard BIO-PSA series (7-4400, 7-4500 and 7-4600 series), the amine compatible (endcapped) BIO-PSA series (7-4100, 7-4200 and 7-4300 series) and the Soft Skin Adhesives series (7-9800) manufactured by Dow Corning. Preferred pressure-sensitive adhesives based on polysiloxane are heptane-solvated pressure-sensitive adhesives including BIO-PSA 7-4201, BIO-PSA 7-4301, BIO-PSA 7-4501. For example, BIO-PSA 7-4201 is characterized by a solution viscosity at 25° C. and about 70% solids content in heptane of 450 mPa s and a complex viscosity at 0.01 rad/s at 30° C. of $1\times10^8$ Poise. BIO-PSA 7-4301 has a solution viscosity at 25° C. and about 70% solids content in heptane of 500 mPa s and a complex viscosity at 0.01 rad/s at 30° C. of $5\times10^6$ Poise.

The silicone polymers are supplied and used in solvents like n-heptane, ethyl acetate or other volatile silicone fluids. For the present invention n-heptane is preferred. The solids content of the silicone polymers in the solvents is usually between 60 and 80%, preferably between 70 and 80% or between 60 and 70%. The skilled person is aware that the solids content may be modified by adding a suitable amount of solvent.

Silicone polymers, which are, e.g., available from Dow Corning, may be obtained according to the following scheme:

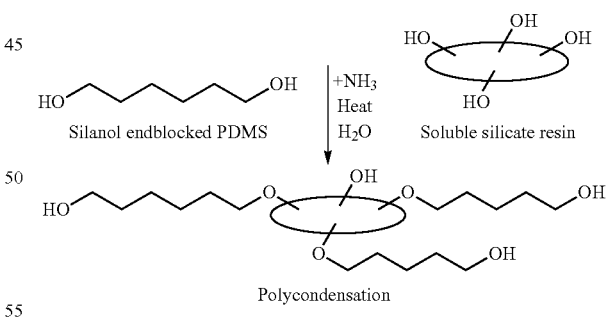

Polycondensation

Such silicone polymers are also referred to as standard silicone adhesive and are available from Dow Corning, e.g., under the tradenames BIO-PSA 7-4401, BIO-PSA-7-4501, or BIO-PSA 7-4601, which are provided in the solvent n-heptane (indicated by the code "01"), or under the tradenames BIO-PSA 7-4402, BIO-PSA 7-4502, and BIO 7-4602, which are provided in the solvent ethyl acetate (indicated by the code "02"). Typical solids contents in the solvent are in the range of from 60 to 75%. The code "44" indicates a resin-to-polymer ratio of 65:35 resulting in a low tackiness, the code "45" indicates a resin-to-polymer ratio of 60:40 resulting in medium tackiness, the code "46" indicates a resin-to-polymer ratio of 55:45 resulting in high tackiness.

Amine-compatible silicone polymers, which are, e.g., available from Dow Corning may be obtained according to the following scheme:

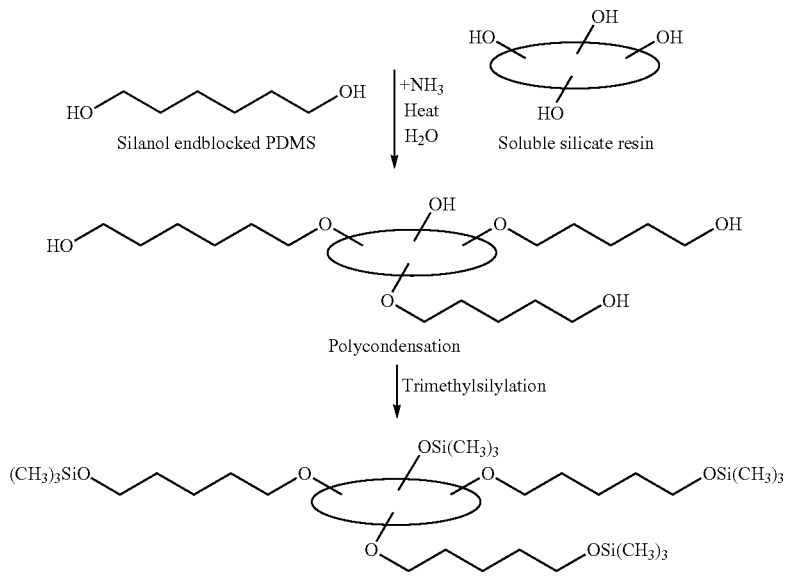

Such amine-compatible silicone polymers are available from Dow Corning, e.g., under the tradenames BIO-PSA 7-4101, BIO-PSA-7-4201, or BIO-PSA 7-4301, which are provided in the solvent n-heptane (indicated by the code "01"), or under the tradenames BIO-PSA 7-4102, BIO-PSA 7-4202, and BIO 7-4302, which are provided in the solvent ethyl acetate (indicated by the code "02"). Typical solids contents in the solvent are in the range of from 60 to 75%. The code "41" indicates a resin-to-polymer ratio of 65:35 resulting in a low tackiness, the code "42" indicates a resin-to-polymer ratio of 60:40 resulting in medium tackiness, the code "43" indicates a resin-to-polymer ratio of 55:45 resulting in high tackiness.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s, preferably as measured using a Brookfield RVT viscometer equipped with a spindle number 5 at 50 rpm. Theses may also be characterized by a complex viscosity at 0.01 rad/s at 30° C. of less than about $1\times10^9$ Poise or from about $1\times10^5$ to about $9\times10^8$ Poise.

The adhesive strength of the polysiloxanes may be sufficient for the desired skin contact. In certain embodiments of the invention a plasticizer or a tackifying agent is incorporated into the formulation to improve the adhesive characteristics of the pressure-sensitive adhesive. It may be advantageous in an individual case to improve the tack by adding small amounts of tackifiers such as polyterpenes, rosin derivatives, or silicone oils. In preferred embodiments, the tackifying agent is a silicone oil (e.g., 360 Medical Fluid, available from Dow Corning Corporation, Midland, Mich.).

The pressure-sensitive adhesives are supplied and used in solvents like n-heptane, ethyl acetate or other volatile silicone fluids. For the present invention n-heptane is preferred. The solids content of polysiloxanes in solvents is usually between 60 and 85%, preferably between 70 and 80%. The solids content of polyisobutylenes in solvents is usually between 30 and 50%, preferably between 35 and 40%. The skilled person is aware that the solids content may be modified by adding a suitable amount of solvent.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s. Theses may also be characterized by a complex viscosity at 0.01 rad/s at 30° C. of less than about $1\times10^9$ Poise or from about $1\times10^5$ to about $9\times10^8$ Poise.

Suitable pressure-sensitive adhesives based on polysiloxanes may be obtained from Dow Corning® BIO-PSA Standard Silicone Adhesives. Preferred is the BIO-PSA 7 4301.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. In particular, it is preferred that the at least one polyisobutylene is a combination of a low molecular weight polyisobutylene and a high molecular weight polyisobutylene in a ratio of from 99:1 to 50:50, preferably from 90:10 to 60:40. Typically, the low molecular weight polyisobutylene has a viscosity average molecular weight of from 10,000 to 70,000 g/mol and/or a weight average molecular weight of from 10,000 to 70,000 g/mol, and the high molecular weight polyisobutylene has a viscosity average molecular weight of from 1,000,000 to 1,200,000 g/mol and/or a weight average molecular weight of from 1,400,000 to 1,600,000 g/mol. Particularly preferably, the low molecular weight polyisobutylene has a viscosity average molecular weight of from 38,000 to 42,000 g/mol and/or a weight average molecular weight of from 34,000 to 40,000 g/mol, and the high molecular weight polyisobutylene has a viscosity average molecular weight of from 1,100,000 to 1,120,000 g/mol and/or a weight average molecular weight of from 1,540,000 to 1,560,000 g/mol. A preferred example for a polyisobutylene combination is B10/B100 in a ratio of 85/15 or 90/10. Oppanol® B100 has a viscosity average molecular weight $M_v$ of 1,110,000, and a weight average molecular weight $M_w$ of 1,550,000. Oppanol® B10 has a viscosity average molecular weight $M_v$ of 40,000, and a weight average molecular weight $M_w$ of 36,000. In certain embodiments, polybutene may be added to the polyisobutylenes.

Additional polymers and additives may also be added to enhance cohesion and/or adhesion.

Certain polymers in particular reduce the cold flow and are thus in particular suitable as additional polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prevented by the addition of certain polymers. A basic acrylate polymer (e.g. Eudragit® E100) may e.g. be used to reduce the cold flow. Thus, in certain embodiments, the matrix layer composition comprises additionally a basic polymer, in particular an amine-functional acrylate as e.g. Eudragit® E100. Eudragit® E100 is a cationic copolymer based on dimethylaminoethyl methacrylate, butyl methacrylate, and methyl methacrylate with a ratio of 2:1:1. The monomers are randomly distributed along the copolymer chain. Based on SEC method, the weight average molar mass (Mw) of Eudragit® E100 is approximately 47,000 g/mol.

Further Additives

The TTS according to the invention, and in particular the asenapine-containing layer may further comprise at least one additive or excipient. Said additives or excipients are preferably selected from the group consisting of crystallization inhibitors, solubilizers, hydrophilic polymers, fillers, substances for skincare, pH regulators, preservatives, tackifiers, softeners, stabilizers, and permeation enhancers, in particular from crystallization inhibitors, substances for skincare, tackifiers, softeners, stabilizers, and permeation enhancers. Furthermore, said additives or excipients are preferably selected from the group consisting of crystallization inhibitors, solubilizers, fillers, substances for skincare, pH regulators, preservatives, tackifiers, softeners, stabilizers, and permeation enhancers, in particular from crystallization inhibitors, substances for skincare, tackifiers, softeners, stabilizers, and permeation enhancers. Such additives may be present in the asenapine-containing layer in an amount of from 0.001% to 20% by weight or from 0.001% to 15% by weight, e.g. from 1 to 10% by weight or from 0.01 to 5% by weight, based on the total weight of the asenapine-containing layer per additive. In certain embodiments, the total amount of all additives is from 0.001% to 25% of the asenapine-containing layer. Hereinafter, where a range for an amount of a specific additive is given, such a range refers to the amount per individual additive.

Particularly preferred additives are selected from crystallization inhibitors and stabilizers. In a preferred embodiment of the invention, the TTS comprises a stabilizer in an amount of from 0.01 to 1.0% by weight and/or a crystallization inhibitor in an amount of from 0.5 to 10% by weight based on the total weight of the asenapine-containing layer. These additives are particularly preferred in connection with a TTS comprising a silicone polymer in the asenapine-containing layer.

In connection with a TTS comprising a polyisobutylene in the asenapine-containing layer, it is preferred that the TTS comprises a hydrophilic polymer in an amount of from 1 to 20% by weight, preferably 5 to 15% by weight. The hydrophilic polymer allow that the TTS takes up water, which may improve the release properties.

It should be noted that in pharmaceutical formulations, the formulation components are categorized according to their physicochemical and physiological properties, and in accordance with their function. This means in particular that a substance or a compound falling into one category is not excluded from falling into another category of formulation component. E.g. a certain polymer can be a crystallization inhibitor but also a tackifier. Some substances may e.g. be a typical softener but at the same time act as a permeation enhancer. The skilled person is able to determine based on his general knowledge in which category or categories of formulation component a certain substance or compound belongs to. In the following, details on the excipients and additives are provided which are, however, not to be understood as being exclusive. Other substances not explicitly listed in the present description may be as well used in accordance with the present invention, and substances and/or compounds explicitly listed for one category of formulation component are not excluded from being used as another formulation component in the sense of the present invention.

In one embodiment, the asenapine-containing layer further comprises a crystallization inhibitor. In some embodiments, the crystallization inhibitor can be present in an amount of from 0.5 to 10% by weight based on the total weight of the asenapine-containing layer. Suitable examples of crystallization inhibitors include polyvinylpyrrolidone, vinyl acetate/vinylpyrrolidone copolymer and cellulose derivatives. The crystallization inhibitor is preferably polyvinylpyrrolidone, more preferably soluble polyvinylpyrrolidone. The crystallization inhibitor may increase the solubility of the active agent or inhibit the crystallization of the active agent.

In one embodiment, the asenapine-containing layer further comprises a stabilizer, wherein the stabilizer is preferably selected from tocopherol and ester derivatives thereof and ascorbic acid and ester derivatives thereof. If the asenapine-containing layer comprises a stabilizer, the stabilizer is present in an amount of from 0.001 to 2.0% by weight, preferably from 0.01 to 1.0% by weight based on the total weight of the asenapine-containing layer. In some embodiments, preferred stabilizers include sodium metabisulfite, ascorbyl esters of fatty acids such as ascorbyl palmitate, ascorbic acid, butylated hydroxytoluene, tocopherol, tocopheryl acetate and tocopheryl linoleate. Preferred stabilizers include ascorbyl esters of fatty acids, ascorbic acid, tocopherol, tocopheryl acetate and tocopheryl linoleate. Particularly preferred is tocopherol. Also particularly preferred is a combination of tocopherol and ascorbyl palmitate.

In one embodiment, the asenapine-containing layer further comprises a softener/plasticizer. Exemplary softeners/plasticizers include linear or branched, saturated or unsaturated alcohols having 6 to 20 carbon atoms, triglycerides and polyethylene glycols.

In one embodiment, the asenapine-containing layer further comprises a solubilizer. Preferred solubilizers include, e.g., glycerol-, polyglycerol-, propylene glycol- and polyoxyethylene-esters of medium chain and/or long chain fatty acids, such as glyceryl monolinoleate, medium chain glycerides and medium chain triglycerides, non-ionic solubilisers made by reacting castor oil with ethylene oxide, and any mixtures thereof which may further contain fatty acids or fatty alcohols; cellulose and methylcellulose and derivatives thereof such as hydroxypropylcellulose and hypromellose acetate succinate; various cyclodextrins and derivatives thereof; non-ionic tri-block copolymers having a central hydrophobic chain of polyoxypropylene flanked by two hydrophilic chains of polyoxyethylene known as poloxamers; a polyethylene glycol, polyvinyl acetate and polyvinylcaprolactame-based graft copolymer, also abbreviated as PVAc-PVCap-PEG and known as Soluplus®; purified grades of naturally derived castor oil, of polyethylene glycol 400, of polyoxyethylene sorbitan monooleate (such as polysorbate 80) or of propylene glycols; diethylene glycol monoethyl ether; as well as any of the below mentioned soluble polyvinylpyrrolidones, but also insoluble/cross-linked polyvinylpyrrolidones also known as crospovidones such as Kollidon® CL, Kollidon® CL-M and Kollidon® CL-SF, and polyvinylpyrrolidone-polyvinyl acetate copolymers, also known as copovidones, such as Kollidon® VA64.

However, also the permeation enhancers mentioned below can act as solubilizers. Furthermore, also crystallization inhibitors may act as solubilizers.

In one embodiment, the asenapine-containing layer further comprises a hydrophilic polymer, which preferably allows that the TTS takes up water. Some of the above-mentioned solubilizers may also be useful as hydrophilic polymers. Preferred hydrophilic polymers include glycerol-, polyglycerol-, propylene glycol- and polyoxyethylene-esters, cellulose and methylcellulose and derivatives thereof such as hydroxypropylcellulose and hypromellose acetate succinate; non-ionic tri-block copolymers having a central hydrophobic chain of polyoxypropylene flanked by two hydrophilic chains of polyoxyethylene known as poloxamers; a polyethylene glycol, polyvinyl acetate and polyvinylcaprolactame-based graft copolymer, also abbreviated as PVAc-PVCap-PEG and known as Soluplus®; purified grades of naturally derived castor oil, of polyoxyethylene sorbitan monooleate (such as polysorbate 80) or of propylene glycols; diethylene glycol monoethyl ether; as well as any of the below mentioned soluble polyvinylpyrrolidones, but also insoluble/cross-linked polyvinylpyrrolidones also known as crospovidones such as Kollidon® CL, Kollidon® CL-M and Kollidon® CL-SF, and polyvinylpyrrolidone-polyvinyl acetate copolymers, also known as crospovidones, such as Kollidon® VA64. A particularly preferred hydrophilic polymer is polyvinylpyrrolidone.

In one embodiment, the asenapine-containing layer further comprises a pH regulator. Suitable pH regulators include mild acids and bases including amine derivatives, inorganic alkali derivatives, and polymers with basic or acidic functionality.

In one embodiment, the asenapine-containing layer further comprises a preservative. Suitable preservatives include parabens, formaldehyde releasers, isothiazolinones, phenoxyethanol, and organic acids such as benzoic acid, sorbic acid, levulinic acid and anisic acid.

In one embodiment, the asenapine-containing layer further comprises a substance for skincare. Such substances may be used to avoid or reduce skin irritation as detectable by the dermal response score. Suitable substances for skincare include sterol compounds such as cholesterol, dexpanthenol, alpha-bisabolol, and antihistamines. Substances for skincare are preferably used in amounts of from 1 to 10% by weight based on the total weight of the asenapine-containing layer.

If the asenapine-containing layer is required to have self-adhesive properties and one or more polymers is/are selected, which does/do not provide sufficient self-adhesive properties, a tackifier is added. Preferred tackifiers include Miglyol, which is a liquid wax ester based on long-chain, unsaturated, even-numbered fatty acids and long-chain, unsaturated, even-numbered fatty alcohols of vegetable origin, and polyethyleneglycols. In particular, the tackifier may be selected from polyvinylpyrrolidone (which, due to its ability to absorb water, is able to maintain the adhesive properties of the matrix layer and thus can be regarded as a tackifier in a broad sense), triglycerides, polyethylene glycols, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone. Preferably, the tackifier may be selected from polyvinylpyrrolidone, triglycerides, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone. In some embodiments, the tackifier can be present in an amount of from 5 to 15% by weight based on the total weight of the asenapine-containing layer.

The term "soluble polyvinylpyrrolidone" refers to polyvinylpyrrolidone, also known as povidone, which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F. The different grades of Kollidon® are defined in terms of the K-Value reflecting the average molecular weight of the polyvinylpyrrolidone grades. Kollidon® 12 PF is characterized by a K-Value range of 10.2 to 13.8, corresponding to a nominal K-Value of 12. Kollidon® 17 PF is characterized by a K-Value range of 15.3 to 18.4, corresponding to a nominal K-Value of 17. Kollidon® 25 is characterized by a K-Value range of 22.5 to 27.0, corresponding to a nominal K-Value of 25. Kollidon® 30 is characterized by a K-Value range of 27.0 to 32.4, corresponding to a nominal K-Value of 30. Kollidon® 90 F is characterized by a K-Value range of 81.0 to 97.2, corresponding to a nominal K-Value of 90. Preferred Kollidon® grades are Kollidon® 12 PF, Kollidon® 30 and Kollidon® 90 F.

Within the meaning of this invention, the term "K-Value" refers to a value calculated from the relative viscosity of polyvinylpyrrolidone in water according to the European Pharmacopoeia (Ph.Eur.) and USP monographs for "Povidone".

In one embodiment, the asenapine-containing layer further comprises a permeation enhancer. Permeation enhancers are substances, which influence the barrier properties of the stratum corneum in the sense of increasing the active agent permeability. Some examples of permeation enhancers are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methylcetylsulfoxide, dimethylaurylamine, dodecyl pyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate.

If the asenapine-containing layer further comprises a permeation enhancer, the permeation enhancer is preferably selected from diethylene glycol monoethyl ether (transcutol), diisopropyl adipate, isopropyl myristate, isopropyl palmitate, lauryl lactate, and dimethylpropylene urea.

In one embodiment, the asenapine-containing layer does not comprise isopropyl palmitate as permeation enhancer.

In one embodiment, the asenapine-containing layer does not comprise a permeation enhancer selected from oleic acids, oleic alcohols, and triglycerides.

In one embodiment, the asenapine-containing layer does not comprise sodium acetate or sodium diacetate. In yet another embodiment, the asenapine-containing layer does not comprise a dicarboxylic acid alkali salt. In yet another embodiment, the asenapine-containing layer does not comprise a maleic acid alkali salt.

It has been found that the TTS provides sufficient permeability of the active agent even if no permeation enhancer is present. Therefore, in certain embodiments of the invention, the asenapine-containing layer does not comprise a permeation enhancer.

Fillers such as silica gels, titanium dioxide and zinc oxide may be used in conjunction with the polymer in order to influence certain physical parameters, such as cohesion and bond strength, in the desired way.

Release Characteristics

The TTS in accordance with the invention are designed for transdermally administering asenapine to the systemic circulation for a predefined extended period of time.

In one embodiment, the TTS according to the invention provides a mean release rate of from 0.5 to 20 mg/day, preferably from 3 to 10 mg/day, more preferably of from 3 to 8 mg/day asenapine over at least 24 hours of administration.

In one embodiment, the TTS according to the invention provides a skin permeation rate of asenapine as measured in a Franz diffusion cell with dermatomed human skin of 0 $\mu g/(cm^2*h)$ to 12 $\mu g/(cm^2*h)$ in the first 4 hours,
1 $\mu g/(cm^2*h)$ to 22 $\mu g/(cm^2*h)$ from hour 4 to hour 8,
6 $\mu g/(cm^2*h)$ to 25 $\mu g/(cm^2*h)$ from hour 8 to hour 12,
5 $\mu g/(cm^2*h)$ to 20 $\mu g/(cm^2*h)$ from hour 12 to hour 16,
4 $\mu g/(cm^2*h)$ to 18 $\mu g/(cm^2*h)$ from hour 16 to hour 20,
2 $\mu g/(cm^2*h)$ to 12 $\mu g/(cm^2*h)$ from hour 20 to hour 24.

In one embodiment, the transdermal therapeutic system according to the invention provides a cumulative permeated amount of asenapine as measured in a Franz diffusion cell with dermatomed human skin of 120 $\mu g/cm^2$ to 380 $\mu g/cm^2$ over a time period of 24 hours.

In one embodiment, the transdermal therapeutic system according to the invention provides a permeated amount of asenapine as measured in a Franz diffusion cell with dermatomed human skin of 0 $\mu g/cm^2$ to 50 $\mu g/cm^2$ in the first 4 hours,
20 $\mu g/cm^2$ to 120 $\mu g/cm^2$ from hour 4 to hour 8,
40 $\mu g/cm^2$ to 220 $\mu g/cm^2$ from hour 8 to hour 12,
60 $\mu g/cm^2$ to 290 $\mu g/cm^2$ from hour 12 to hour 16,
80 $\mu g/cm^2$ to 340 $\mu g/cm^2$ from hour 16 to hour 20,
100 $\mu g/cm^2$ to 380 $\mu g/cm^2$ from hour 20 to hour 24.

Method of Treatment/Medical Use

In accordance with a specific aspect of the present invention, the TTS according to the invention is for use in a method of treatment, and in particular in a method of treating a human patient.

In certain embodiments, the TTS according to the invention is for use in a method of treating psychosis in general, and in particular for use in a method of treating one or more conditions selected from schizophrenia, bipolar disorder, posttraumatic stress disorder, major depressive disorder, dementia related psychosis, agitation and manic disorder in a human patient.

In certain embodiments, the TTS according to the invention is for use in a method of treating schizophrenia and/or bipolar disorder in a human patient, and in particular for use in a method of treating acute manic or mixed episodes of bipolar disorder in a human patient. In certain embodiments, the TTS according to the invention is for use in a method of treating acute manic or mixed episodes of bipolar disorder in an adult or a pediatric patient 10 to 17 years of age.

In certain embodiments, the TTS according to the invention is for use as an adjunctive treatment to lithium or valproate in a method of treating bipolar disorder in a human patient, in particular an adult. In certain embodiments, the TTS according to the invention is for use as a maintenance monotherapy treatment in a method of treating bipolar disorder in a human patient, in particular an adult.

In certain embodiments, the TTS according to the invention is for use in a method of treatment, preferably in a method of treating psychosis in general, and in particular for use in a method of treating one or more conditions selected from schizophrenia, bipolar disorder, posttraumatic stress disorder, major depressive disorder, dementia related psychosis, agitation and manic disorder in a human patient, and especially preferably in a method of treating schizophrenia and/or bipolar disorder, wherein the TTS is applied to the skin of the patient for a dosing interval of at least 20 hours. In one embodiment, the TTS according to the invention is for use in a method of treatment, wherein the TTS is applied to the skin of the patient for a dosing interval of from 20 to 30 hours, preferably about 24 hours. Accordingly, the TTS is preferably for use in a method of treatment, preferably in a method of treating schizophrenia and/or bipolar disorder, wherein an around-the-clock treatment is performed with a once-a-day TTS exchange mode (dosing interval of 24 hours). In connection with the afore-mentioned embodiments, the term "dosing interval" is to be understood as the time period between the time of administering a first TTS of the invention and replacing the TTS by a second TTS of the invention. Thus, the administration time of the TTS preferably corresponds to the time of the dosing interval and is preferably from 20 to 30 hours, particularly preferably about 24 hours. In connection with the above uses and methods of treatment, the TTS according to the invention is preferably applied to at least one body surface on the subject selected from the upper outer art, upper chest, upper hack or the side of the chest for the defined dosing intervals.

It has been found that the TTS of the invention provides blood plasma concentrations of asenapine over 24 hours, which are comparable to the blood plasma concentrations obtained with sublingual asenapine tablets, when administered in dosage strengths of 5 mg or 10 mg twice daily (BID).

Thus, in one embodiment, the TTS according to the invention provides by passive transdermal delivery an $AUC_{0-24}$ of from 5 to 100 (ng/ml)*h. In a preferred embodiment, the TTS provides by passive transdermal delivery an $AUC_{0-24}$ of from 10 to 90 (ng/mL)*h.

Process of Manufacture

The invention further relates to a process of manufacture of an asenapine-containing layer, preferably an asenapine-containing matrix layer, for use in a transdermal therapeutic system.

In accordance with the invention, the process for manufacturing an asenapine-containing layer for use in a transdermal therapeutic system according to the invention comprises the steps of:
1) combining at least the components
   1. asenapine in the form of asenapine base;
   2. a polymer selected from the group consisting of polysiloxanes and polyisobutylenes in an amount of more than 50% by weight based on the total weight of the asenapine-containing layer; and
   3. optionally at least one additive;
   to obtain a coating composition;
2) coating the coating composition onto the backing layer or release liner or any intermediate liner; and
3) drying the coated coating composition to form the matrix layer.

In this process of manufacture, preferably in step 1) the asenapine is preferably dissolved to obtain a coating composition.

In the above described process, the solvent is preferably selected from alcoholic solvents, in particular methanol, ethanol, isopropanol and mixtures thereof, and from non-alcoholic solvents, in particular ethyl acetate, hexane, heptane, petroleum ether, toluene, and mixtures thereof, and is more preferably selected from non-alcoholic solvents, and is most preferably ethyl acetate or n-heptane.

In certain embodiments, the polymer in the above process is polysiloxane, which is provided as a solution and preferably as a solution in n-heptane or ethyl acetate with a solids content of from 60 to 80% by weight.

In step 3), drying is performed preferably at a temperature of from 50 to 90° C., more preferably from 60 to 90° C.

It is to be understood that the process above may be modified in line with the aspects and embodiments of the invention outlined above, in particular with regard to the preferences provided in connection with the asenapine, the polymer and the additives.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Example 1

Coating Composition

The formulation of the asenapine-containing coating composition of Example 1 is summarized in Table 1.1 below.

TABLE 1.1

| Ingredient (Trade Name) | Ex. 1 | | | |
| --- | --- | --- | --- | --- |
| | Solid [g] | Solid [%] | Liquid [g] | Liquid [%] |
| Asenapine Base | 0.4899 | 7.001 | 0.4899 | 4.805 |
| Silicone adhesive in n-heptane. Solids content of 72.40% by weight (DOW CORNING ® BIO-PSA Q7-4301) | 6.508 | 92.999 | 8.9890 | 88.161 |
| Ethyl acetate | | | 0.7172 | 7.034 |
| Total | 6.9979 | 100.00 | 10.1961 | 100.00 |
| Area Weight [g/m$^2$] | | 77.8 | | |
| Loading API [µg/cm$^2$] | | 544.7 | | |

Preparation of the Coating Composition

A beaker was loaded with the asenapine base. The solvent (ethyl acetate) was added, followed by the addition of the silicone pressure sensitive adhesive (DOW CORNING® BIO-PSA Q7-4301). The mixture was stirred at approx. 300 rpm until a homogenous mixture was obtained (at least 60 min).

Coating of the Coating Composition of Example

The resulting asenapine-containing coating composition was coated on a polyethylene terephthalate film (one side fluoropolymer coated, 75 µm thickness, which may function as release liner) and dried for approx. 15 min at approx. room temperature and approx. 25 min at approx. 60° C. The coating thickness gave an area weight of the matrix layer of 77.8 g/m$^2$. The dried film was laminated with a polyethylene terephthalate backing layer (beige lacquered, 23 µm thickness) to provide an asenapine-containing self-adhesive layer structure.

Preparation of the TTS (Concerning all Examples)

The individual systems (TTS) were then punched out from the asenapine-containing self-adhesive layer structure. In specific embodiments a TTS as described above can be provided with a further self-adhesive layer of larger surface area, preferably with rounded corners, comprising a pressure-sensitive adhesive matrix layer which is free of active agent. This is of advantage when the TTS, on the basis of its physical properties alone, does not adhere sufficiently to the skin and/or when the asenapine-containing matrix layer, for the purpose of avoiding waste, has pronounced corners (square or rectangular shapes). The TTS are then punched out and sealed into pouches of the primary packaging material.

Measurement of Skin Permeation Rate

The permeated amount and the corresponding skin permeation rates of TTS prepared according to Example 1 was determined by in vitro experiments in accordance with the OECD Guideline (adopted Apr. 13, 2004) carried out with a 10.0 ml Franz diffusion cell. Split thickness human skin from cosmetic surgeries (e.g., female abdomen, date of birth 1954) was used. A dermatome was used to prepare skin to a thickness of 800 µm, with an intact epidermis for all TTS. Diecuts with an area of 1.15 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 1.2 and FIG. 1.

TABLE 1.2

| Elapsed time [h] | Skin permeation rate with SD [µg/cm²h] Ex. 1 (n = 3) | |
|---|---|---|
| | Rate | SD |
| 0 | 0 | 0 |
| 4 | 2.65 | 2.29 |
| 8 | 20.02 | 0.22 |
| 12 | 23.35 | 0.16 |
| 16 | 18.71 | 0.52 |
| 20 | 13.26 | 0.03 |
| 24 | 8.52 | 0.4 |
| 32 | 8.4 | 0.59 |
| 40 | 3.07 | 0.08 |
| 48 | 1.99 | 0.12 |

Example 2

Coating Composition

The formulation of the asenapine-containing coating composition of Example 2 is summarized in Table 2.1 below.

TABLE 2.1

| Ingredient (Trade Name) | Ex. 2 | | | |
|---|---|---|---|---|
| | Solid [g] | Solid [%] | Liquid [g] | Liquid [%] |
| Asenapine Base | 0.2484 | 3.543 | 0.2484 | 2.436 |
| Silicone adhesive in n-heptane. Solids content of 72.40% by weight (DOW CORNING ® BIO-PSA Q7-4301) | 6.7444 | 96.195 | 9.3155 | 91.343 |
| α-Tocopherol | 0.0184 | 0.262 | 0.0184 | 0.180 |
| Ethyl acetate | | | 0.6161 | 6.041 |
| Total | 7.0112 | 100.00 | 10.1984 | 100.00 |
| Area Weight [g/m²] | | 75.1 | | |
| Loading API [µg/cm²] | | 275.6 | | |

Preparation of the Coating Composition

The coating composition was prepared as described in Example 1, wherein α-tocopherol was added before the addition of the solvent. The mixture was however stirred from approx. 250 rpm to approx. 1000 rpm until a homogenous mixture was obtained (at least 60 min).

Coating of the Coating Composition

See Example 1 for the coating process. The coating was however dried for approx. 10 min at approx. room temperature and approx. 15 min at approx. 60° C. The coating thickness gave an area weight of the matrix layer of 75.1 g/m². The dried film was laminated with a polyethylene terephthalate backing layer (beige lacquered, 23 µm thickness) to provide an asenapine-containing self-adhesive layer structure.

Preparation of the TTS

See Example 1.

Measurement of Skin Permeation Rate

Figure 2:
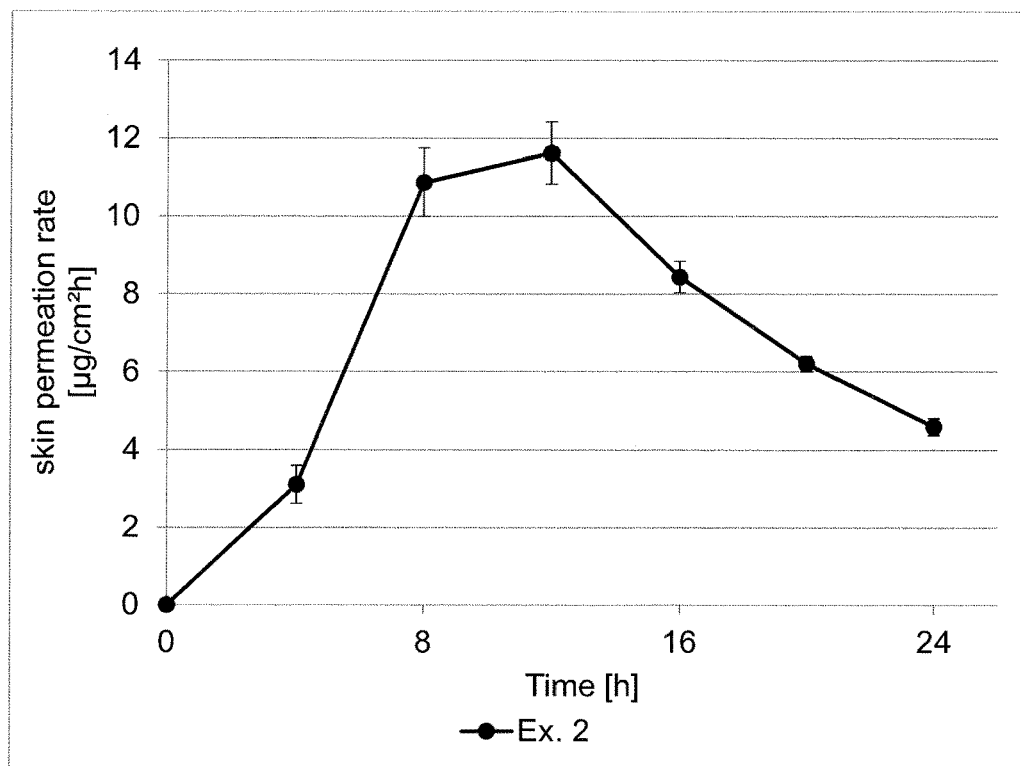
FIG. 2 depicts the asenapine skin permeation rate of TTS prepared according to Example 2.

The permeated amount and the corresponding skin permeation rates of TTS prepared according to Example 2 was determined by in vitro experiments in accordance with the OECD Guideline (adopted Apr. 13, 2004) carried out with a 10.0 ml Franz diffusion cell. Split thickness human skin from cosmetic surgeries (female abdomen, date of birth 1981) was used. A dermatome was used to prepare skin to a thickness of 800 µm, with an intact epidermis for all TTS. Diecuts with an area of 1.15 cm² were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 2.2 and FIG. 2.

TABLE 2.2

| Elapsed time [h] | Skin permeation rate with SD [µg/cm²h] Ex. 2 (n = 3) | |
|---|---|---|
| | Rate | SD |
| 0 | 0 | 0 |
| 4 | 3.11 | 0.49 |
| 8 | 10.87 | 0.87 |
| 12 | 11.62 | 0.79 |
| 16 | 8.43 | 0.4 |
| 20 | 6.2 | 0.19 |
| 24 | 4.58 | 0.22 |

Examples 3AA-BB

Coating Composition

The formulations of the asenapine-containing coating compositions of Examples 3aa-bb are summarized in Tables 3.1a and 3.1b.

TABLE 3.1a

| Ingredient (Trade Name) | Ex. 3aa/3ab | | | |
|---|---|---|---|---|
| | Solid [g] | Solid [%] | Liquid [g] | Liquid [%] |
| Asenapine Base | 0.2484 | 3.543 | 0.2484 | 2.436 |
| Silicone adhesive in n-heptane. Solids content of 72.40% by weight (DOW CORNING ® BIO-PSA Q7-4301) | 6.7444 | 96.195 | 9.3155 | 91.343 |
| α-Tocopherol | 0.0184 | 0.262 | 0.0184 | 0.180 |
| Ethyl acetate | | | 0.6161 | 6.041 |
| Total | 7.0112 | 100.00 | 10.1984 | 100.00 |
| Area Weight [g/m²] | | 75.1 | | |
| Loading API [µg/cm²] | | 275.6 | | |

TABLE 3.1b

| Ingredient (Trade Name) | Ex. 3ba/3bb | | | |
|---|---|---|---|---|
| | Solid [g] | Solid [%] | Liquid [g] | Liquid [%] |
| Asenapine Base | 0.2997 | 2.992 | 0.2997 | 2.054 |
| Silicone adhesive in n-heptane. Solids content of 72.40% by weight (DOW CORNING ® BIO-PSA Q7-4301) | 9.6881 | 96.714 | 13.3814 | 91.702 |
| α-Tocopherol | 0.0295 | 0.294 | 0.0295 | 0.202 |
| Ethyl acetate | | | 0.8817 | 6.042 |
| Total | 10.0173 | 100.00 | 14.5923 | 100.00 |
| Area Weight [g/m²] | | 110.45 | | |
| Loading API [µg/cm²] | | 330.5 | | |

Preparation of the Coating Composition

Figure 3A:
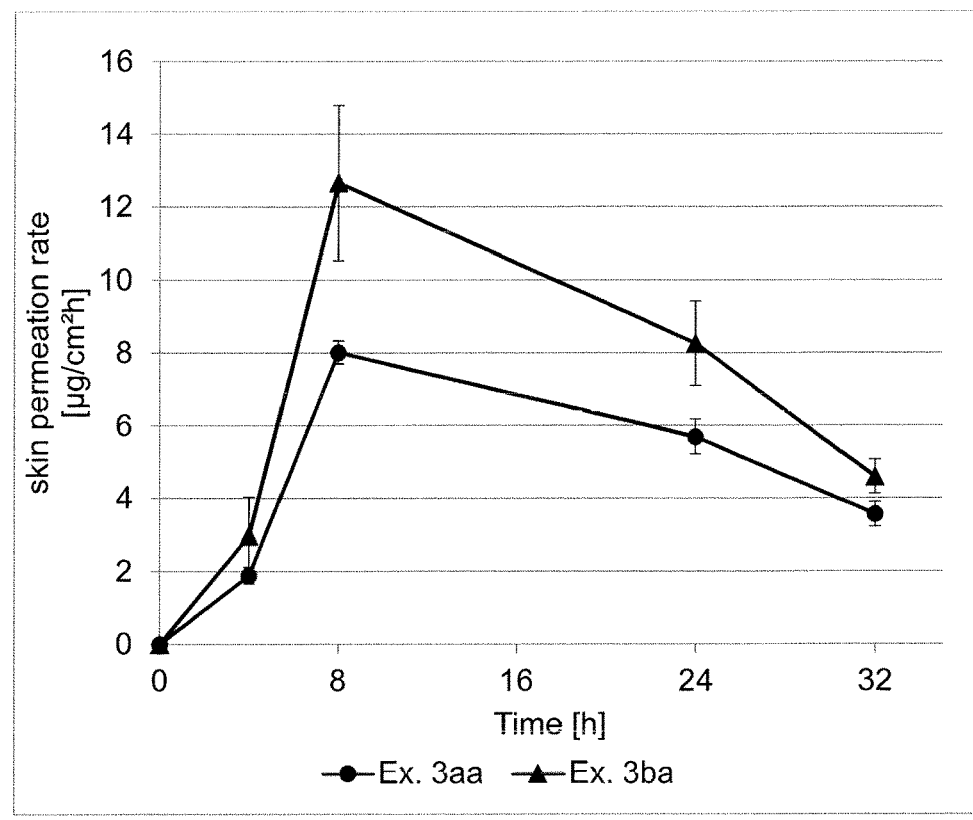
FIG. 3a depicts the asenapine skin permeation rate of TTS prepared according to Examples 3aa and 3ba.
Figure 3B:
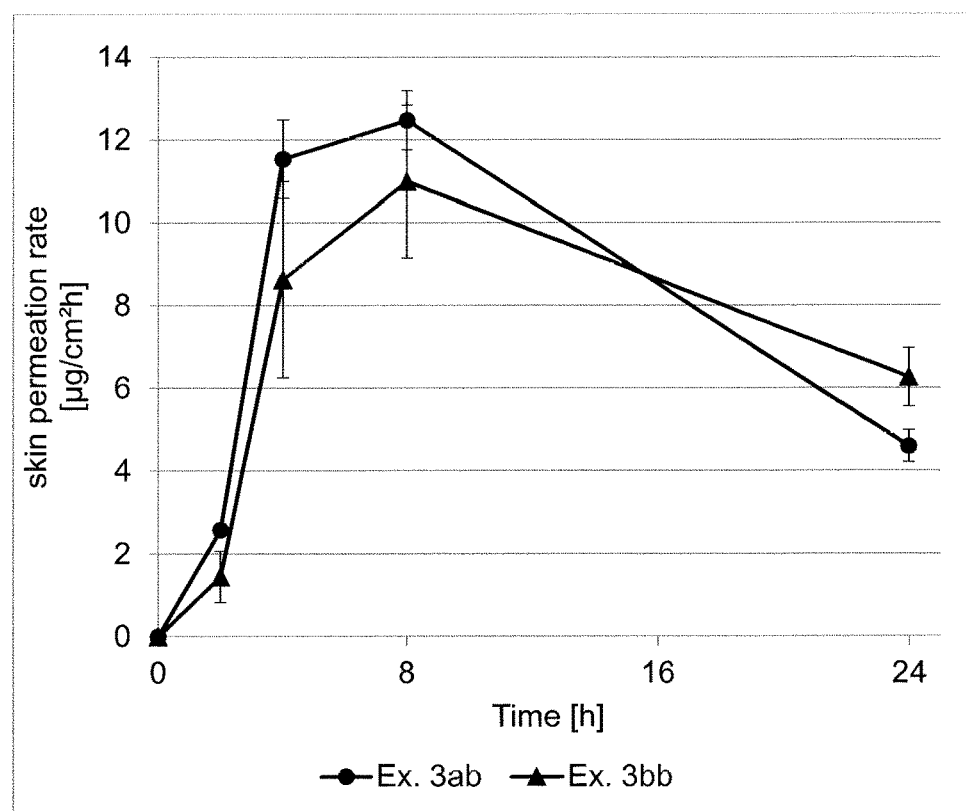
FIG. 3b depicts the asenapine skin permeation rate of TTS prepared according to Examples 3ab and 3bb.

The coating compositions for Examples 3aa and 3ab were prepared as described in Example 2. The coating compositions for Examples 3ba and 3bb were prepared as described in Example 2. The mixture was however stirred from approx. 400 rpm to approx. 1000 rpm until a homogenous mixture was obtained (at least 60 min).
Coating of the Coating Composition For Examples 3aa and 3ab see Example 2 for the coating process. For Examples 3ba and 3bb see Example 1 for the coating process. The coating was however dried for approx. 10 min at approx. room temperature and approx. 20 min at approx. 60° C. The coating thickness gave an area weight of the matrix layer of 75.1 (3aa and 3ab) and 110.45 (3ba and 3bb) g/m² respectively. The dried film was laminated with a polyethylene terephthalate backing layer (beige lacquered, 23 μm thickness) to provide an asenapine-containing self-adhesive layer structure.
Preparation of the TTS See Example 1.
Measurement of Skin Permeation Rate for Examples 3aa and 3ba The permeated amounts and the corresponding skin permeation rates of TTS prepared according to Examples 3aa and 3ba were determined by in vitro experiments in accordance with the OECD Guideline (adopted Apr. 13, 2004) carried out with a 10.0 ml Franz diffusion cell. Split thickness human skin from cosmetic surgeries (male abdomen, date of birth 1955) was used. A dermatome was used to prepare skin to a thickness of 800 μm, with an intact epidermis for all TTS. Diecuts with an area of 1.15 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured. The results are shown in Table 3.2 and FIG. 3a.
Measurement of Skin Permeation Rate for Examples 3ab and 3bb The permeated amounts and the corresponding skin permeation rates of TTS prepared according to Examples 3ab and 3bb were determined by in vitro experiments in accordance with the OECD Guideline (adopted Apr. 13, 2004) carried out with a 10.0 ml Franz diffusion cell. Split thickness human skin from cosmetic surgeries (female abdomen, date of birth 1978) was used. A dermatome was used to prepare skin to a thickness of 800 μm, with an intact epidermis for all TTS. Diecuts with an area of 1.15 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured and the corresponding skin permeation rates calculated. The results are shown in Table 3.2 and FIG. 3b.

TABLE 3.2

| Elapsed time [h] | Skin permeation rate with SD [μg/cm²h] | | | | | | | |
|---|---|---|---|---|---|---|---|---|
| | Ex. 3aa (n = 3) | | Ex. 3ba (n = 3) | | Ex. 3ab (n = 3) | | Ex. 3bb (n = 3) | |
| | Rate | SD | Rate | SD | Rate | SD | Rate | SD |
| 0 | 0 | 0 | 0 | 0 | 0 | 0 | 0 | 0 |
| 2 | / | / | / | / | 2.58 | 0.06 | 1.45 | 0.61 |
| 4 | 1.89 | 0.23 | 2.98 | 1.06 | 11.54 | 0.95 | 8.62 | 2.37 |
| 8 | 8.01 | 0.31 | 12.66 | 2.12 | 12.47 | 0.72 | 10.99 | 1.85 |
| 24 | 5.69 | 0.48 | 8.25 | 1.17 | 4.59 | 0.38 | 6.26 | 0.71 |
| 32 | 3.56 | 0.34 | 4.59 | 0.47 | / | / | / | / |

Examples 4A-C
Coating Composition

The formulations of the asenapine-containing coating compositions of Examples 4a-c are summarized in Tables 4.1a, 4.1b, and 4.1c below.

TABLE 4.1a

| | Ex. 4a | | | |
|---|---|---|---|---|
| Ingredient (Trade Name) | Solid [g] | Solid [%] | Liquid [g] | Liquid [%] |
| Asenapine Base | 0.334 | 6.644 | 0.334 | 4.235 |
| Silicone adhesive in n-heptane. Solids content of 72.40% by weight (DOW CORNING ® BIO-PSA Q7-4301) | 4.29 | 85.34 | 5.93 | 75.19 |
| Transcutol (diethylene glycol monoethyl ether) | 0.403 | 8.017 | 0.403 | 5.110 |
| Petroleum ether, bp 80-110° C. | | | 1.22 | 15.47 |
| Total | 5.027 | 100.00 | 7.887 | 100.01 |
| Area Weight [g/m²] | | 96.2 | | |
| Loading API [μg/cm²] | | 639.2 | | |

TABLE 4.1b

| | Ex. 4b | | | |
|---|---|---|---|---|
| Ingredient (Trade Name) | Solid [g] | Solid [%] | Liquid [g] | Liquid [%] |
| Asenapine Base | 0.330 | 6.565 | 0.330 | 4.163 |
| Silicone adhesive in n-heptane. Solids content of 72.40% by weight (DOW CORNING ® BIO-PSA Q7-4301) | 4.29 | 85.34 | 5.92 | 74.68 |
| Diisopropyladipate | 0.407 | 8.096 | 0.407 | 5.134 |
| Petroleum ether, bp 80-110° C. | | | 1.27 | 16.02 |
| Total | 5.027 | 100.00 | 7.977 | 100.00 |
| Area Weight [g/m²] | | 98.8 | | |
| Loading API [μg/cm²] | | 648.1 | | |

TABLE 4.1c

| | Ex. 4c | | | |
|---|---|---|---|---|
| Ingredient (Trade Name) | Solid [g] | Solid [%] | Liquid [g] | Liquid [%] |
| Asenapine Base | 0.333 | 6.627 | 0.333 | 4.261 |
| Silicone adhesive in n-heptane. Solids content of 72.40% by weight (DOW CORNING ® BIO-PSA Q7-4301) | 4.30 | 85.57 | 5.90 | 75.50 |
| Dimethylpropylene urea | 0.392 | 7.801 | 0.392 | 5.016 |
| Petroleum ether, bp 80-110° C. | | | 1.19 | 15.23 |
| Total | 5.025 | 100.00 | 7.815 | 100.01 |
| Area Weight [g/m²] | | 99.4 | | |
| Loading API [μg/cm²] | | 658.7 | | |

Preparation of the Coating Composition

For the coating compositions of Examples 4a-c, a beaker was loaded with the asenapine base. Dimethylpropylene urea (diisopropyladipate respectively) and the silicone pressure sensitive adhesive (DOW CORNING® BIO-PSA Q7-4301) were added. The mixture was stirred from approx. 200 rpm to approx. 500 rpm for approx. 30 min. Then, for Examples 4a and 4b, the solvent petroleum ether, bp 80-110° C. was added and the mixture was stirred at approx. 500 rpm until a homogenous mixture was obtained for approx. 60 min. For Examples 4c, the solvent petroleum ether, bp 80-110° C. was added while stirring from approx. 500 rpm to approx. 1500 rpm until a homogenous mixture was obtained for approx. 60 min.

Coating of the Coating Composition

For Examples 4a-c see Example 1 for the coating process. The coatings were however dried for approx. 10 min at approx. room temperature and approx. 15 min at approx. 90° C. The coating thickness gave an area weight of the matrix layer of 96.2 (4a), 98.8 (4b), and 99.4 (4c) g/m² respectively. The dried film was laminated with a polyethylene terephthalate backing layer (beige lacquered, 23 µm thickness) to provide an asenapine-containing self-adhesive layer structure.

Preparation of the TTS

See Example 1.

Measurement of Skin Permeation Rate

Figure 4:
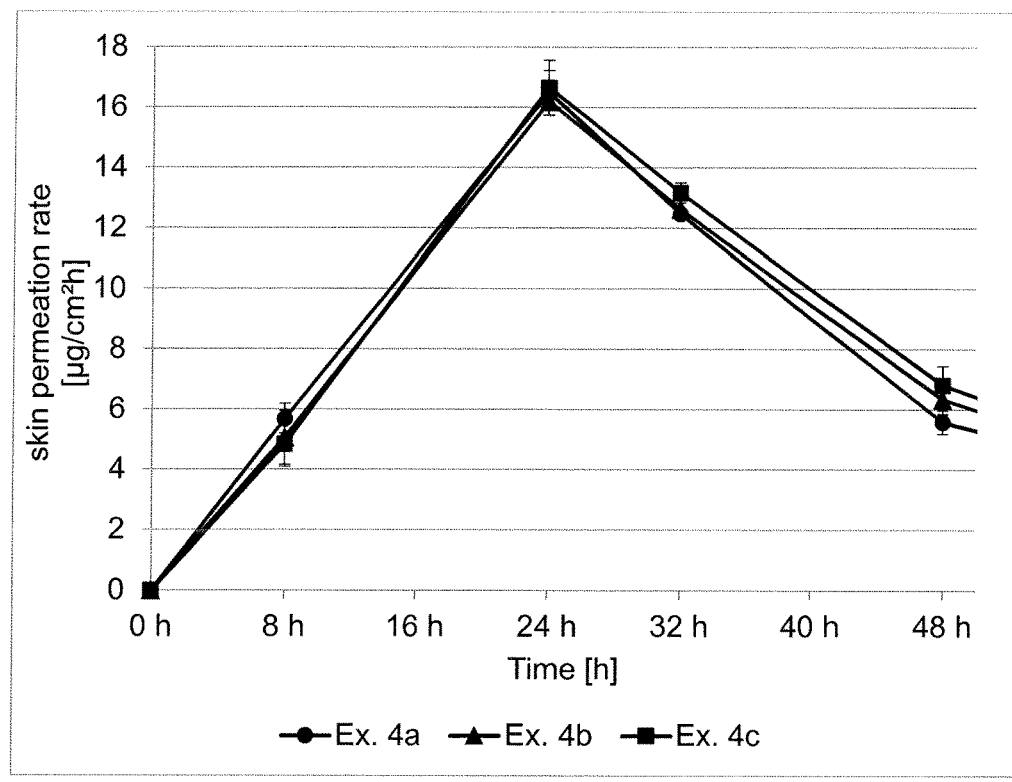
FIG. 4 depicts the asenapine skin permeation rate of TTS prepared according to Examples 4a, 4b and 4c.

The permeated amount and the corresponding skin permeation rates of TTS prepared according to Examples 4a-c was determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 µm, with an intact epidermis for all TTS. Diecuts with an area of 1.15 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured and the corresponding skin permeation rates calculated. The results are shown in Table 4.2 and FIG. 4.

TABLE 4.2

| | Skin permeation rate with SD [µg/cm²h] | | | | | |
|---|---|---|---|---|---|---|
| | Ex. 4a (n = 3) | | Ex. 4b (n = 3) | | Ex. 4c (n = 3) | |
| Elapsed time [h] | Rate | SD | Rate | SD | Rate | SD |
| 0 | 0 | 0 | 0 | 0 | 0 | 0 |
| 8 | 5.69 | 0.5 | 5.06 | 0.9 | 4.85 | 0.75 |
| 24 | 16.48 | 0.74 | 16.19 | 0.44 | 16.65 | 0.91 |
| 32 | 12.47 | 0.14 | 12.63 | 0.35 | 13.17 | 0.33 |
| 48 | 5.58 | 0.39 | 6.34 | 0.49 | 6.81 | 0.62 |

Examples 5A-C

Coating Composition

The formulations of the asenapine-containing coating compositions of Examples 5a-c are summarized in Tables 5.1a, 5.1b, and 5.1c below.

TABLE 5.1a

| | Ex. 5a | | | |
|---|---|---|---|---|
| Ingredient (Trade Name) | Solid [g] | Solid [%] | Liquid [g] | Liquid [%] |
| Asenapine Base | 0.3342 | 6.717 | 0.3342 | 3.74 |
| Silicone adhesive in n-heptane. Solids content of 72.40% by weight (DOW CORNING ® BIO-PSA Q7-4301) | 4.29 | 86.23 | 5.92 | 66.25 |

TABLE 5.1a-continued

| | Ex. 5a | | | |
|---|---|---|---|---|
| Ingredient (Trade Name) | Solid [g] | Solid [%] | Liquid [g] | Liquid [%] |
| Kollidon ® 90 F (polyvinylpyrrolidone) | 0.3511 | 7.057 | 0.3511 | 3.929 |
| Ethanol | | | 2.33 | 26.08 |
| Total | 4.9753 | 100.00 | 8.9353 | 100.00 |
| Area Weight [g/m²] | | 110.5 | | |
| Loading API [µg/cm²] | | 742.23 | | |

TABLE 5.1b

| | Ex. 5b | | | |
|---|---|---|---|---|
| Ingredient (Trade Name) | Solid [g] | Solid [%] | Liquid [g] | Liquid [%] |
| Asenapine Base | 0.3374 | 6.631 | 0.3374 | 2.007 |
| Isobutylene adhesive in petroleum ether, bp 80-110° C. Solids content of 40.85% by weight (Oppanol ® B10/B100 (85:15)) | 4.40 | 86.47 | 10.70 | 63.66 |
| Kollidon ® 90 F (polyvinylpyrrolidone) | 0.3509 | 6.896 | 0.3509 | 2.088 |
| Petroleum ether, bp 80-110° C. | | | 5.42 | 32.25 |
| Total | 5.0883 | 100.00 | 16.8083 | 100.00 |
| Area Weight [g/m²] | | 85.7 | | |
| Loading API [µg/cm²] | | 568.28 | | |

TABLE 5.1c

| | Ex. 5c | | | |
|---|---|---|---|---|
| Ingredient (Trade Name) | Solid [g] | Solid [%] | Liquid [g] | Liquid [%] |
| Asenapine Base | 0.3373 | 6.63 | 0.3373 | 4.315 |
| Silicone adhesive in n-heptane. Solids content of 72.40% by weight (DOW CORNING ® BIO-PSA Q7-4301) | 4.75 | 93.37 | 6.56 | 83.92 |
| Petroleum ether, bp 80-110° C. | | | 0.92 | 11.77 |
| Total | 5.0873 | 100.00 | 7.8173 | 100.01 |
| Area Weight [g/m²] | | 113.5 | | |
| Loading API [µg/cm²] | | 749.52 | | |

Preparation of the Coating Composition

The coating compositions of Examples 5a and 5c were prepared as described in Example 1. Kollidon 90 F (polyvinylpyrrolidone), if any, was added before the addition of the silicone pressure sensitive adhesive, while stirring the mixture from approx. 200 to approx. 500 rpm over approx. 20 min. After addition of the silicone pressure sensitive adhesive, the mixture was then stirred from approx. 200 rpm to approx. 1000 rpm until a homogenous mixture was obtained for further approx. 60 min (for Example 5c, from approx. 1000 rpm to approx. 1500 rpm for further approx. 180 min). For Example 5b, a beaker was loaded with the solvent petroleum ether, bp 80-110° C. The isobutylene pressure sensitive adhesive was added while stirring at approx. 200 rpm, followed by the addition of Kollidon 90 F (polyvinylpyrrolidone) and the asenapine base. The mixture was then stirred from approx. 200 rpm to approx. 1500 rpm until a homogenous mixture was obtained for approx. 160 min.

Coating of the Coating Composition

See Example 4 for the coating process. The coatings of Examples 5b and 5c were however dried for approx. 10 min at approx. room temperature and approx. 20 min at approx. 90° C. The coating thickness gave an area weight of the matrix layer of 110.5 (5a), 85.7 (5b), and 113.5 (5c) g/m² respectively. The dried film was laminated with a polyethylene terephthalate backing layer (beige lacquered, 23 µm thickness) to provide an asenapine-containing self-adhesive layer structure. For Example 5b, a siliconized polyethylene terephthalate release liner having 100 µm thickness is used.

Preparation of the TTS

See Example 1.

Measurement of Skin Permeation Rate

Figure 5:
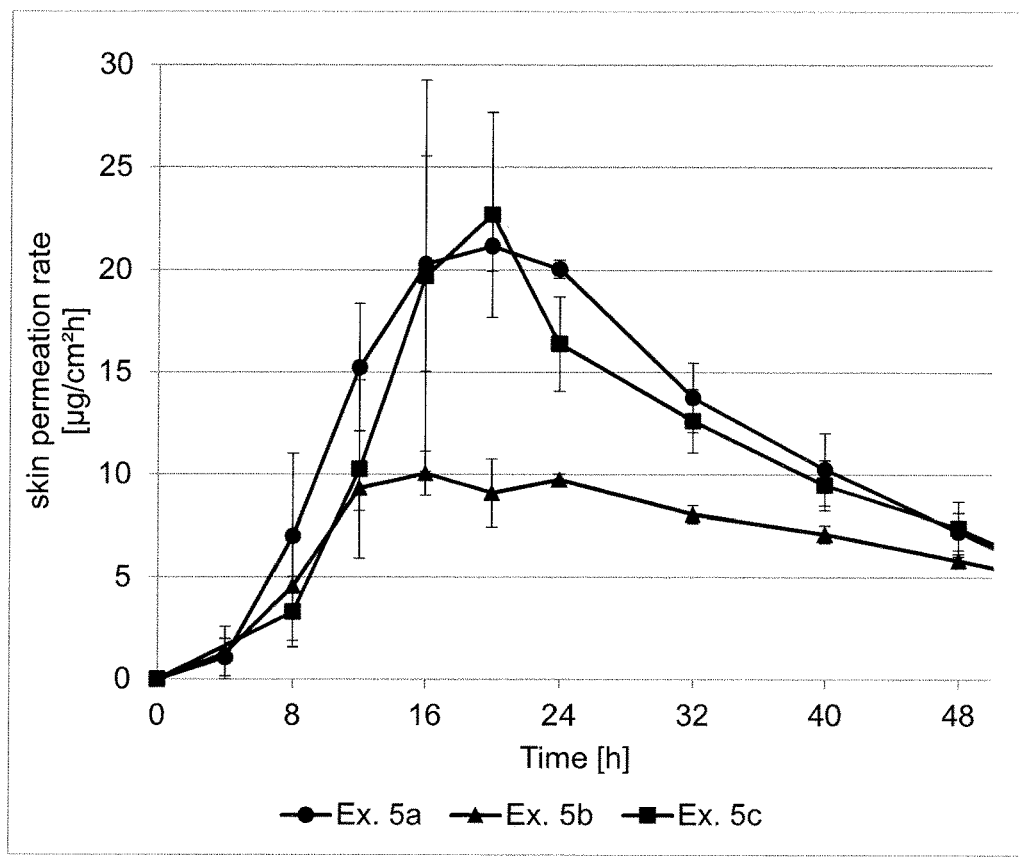
FIG. 5 depicts the asenapine skin permeation rate of TTS prepared according to Examples 5a, 5b and 5c.

The permeated amounts and the corresponding skin permeation rates of TTS prepared according to Examples 5a-c were determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 µm, with an intact epidermis for all TTS. Diecuts with an area of 1.15 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured and the corresponding skin permeation rates calculated. The results are shown in Table 5.2 and FIG. 5.

TABLE 5.2

Skin permeation rate with SD [µg/cm²h]

| Elapsed time [h] | Ex. 5a (n = 3) Rate | SD | Ex. 5b (n = 2) Rate | SD | Ex. 5c (n = 3) Rate | SD |
|---|---|---|---|---|---|---|
| 0 | 0 | 0 | 0 | 0 | 0 | 0 |
| 4 | 1.08 | 0.91 | 1.28 | 1.28 | / | / |
| 8 | 7.02 | 4.01 | 4.58 | 2.7 | 3.31 | 1.73 |
| 12 | 15.24 | 3.11 | 9.34 | 1.12 | 10.26 | 4.34 |
| 16 | 20.29 | 5.26 | 10.06 | 1.08 | 19.7 | 9.55 |
| 20 | 21.15 | 1.21 | 9.1 | 1.65 | 22.67 | 5.01 |
| 24 | 20.03 | 0.45 | 9.74 | 0.27 | 16.38 | 2.31 |
| 32 | 13.76 | 1.71 | 8.07 | 0.44 | 12.61 | 1.55 |
| 40 | 10.25 | 1.76 | 7.11 | 0.41 | 9.47 | 1.22 |
| 48 | 7.23 | 0.9 | 5.83 | 0.19 | 7.42 | 1.28 |

Examples 6A-C

Coating Composition

The formulations of the asenapine-containing coating compositions of Examples 6a-c are summarized in Tables 6.1a, 6.1b, and 6.1c below.

TABLE 6.1a

| | Ex. 6a | | | |
|---|---|---|---|---|
| Ingredient (Trade Name) | Solid [g] | Solid [%] | Liquid [g] | Liquid [%] |
| Asenapine Base | 0.3335 | 6.733 | 0.3335 | 3.371 |
| Silicone adhesive in n-heptane. Solids content of 72.40% by weight (DOW CORNING® BIO-PSA Q7-4301) | 3.53 | 71.26 | 4.88 | 49.33 |

TABLE 6.1a-continued

| | Ex. 6a | | | |
|---|---|---|---|---|
| Ingredient (Trade Name) | Solid [g] | Solid [%] | Liquid [g] | Liquid [%] |
| Acrylate adhesive in ethyl acetate. Solids content of 50.50% by weight (DURO-TAK® 387-2287) | 1.09 | 22.00 | 2.15 | 21.73 |
| Petroleum ether, bp 80-110° C. | | | 2.53 | 25.57 |
| Total | 4.9535 | 99.99 | 9.8935 | 100.00 |
| Area Weight [g/m²] | | 93.7 | | |
| Loading API [µg/cm²] | | 630.66 | | |

TABLE 6.1b

| | Reference Ex. 6b | | | |
|---|---|---|---|---|
| Ingredient (Trade Name) | Solid [g] | Solid [%] | Liquid [g] | Liquid [%] |
| Asenapine Base | 0.3399 | 6.731 | 0.3399 | 3.216 |
| Silicone adhesive in n-heptane. Solids content of 72.40% by weight (DOW CORNING® BIO-PSA Q7-4301) | 2.34 | 46.34 | 3.23 | 30.56 |
| Acrylate adhesive in ethyl acetate. Solids content of 50.50% by weight (DURO-TAK® 387-2287) | 2.37 | 46.93 | 4.69 | 44.37 |
| Ethyl acetate | | | 2.31 | 21.85 |
| Total | 5.0499 | 100.00 | 10.5699 | 100.00 |
| Area Weight [g/m²] | | 130.2 | | |
| Loading API [µg/cm²] | | 876.38 | | |

TABLE 6.1c

| | Reference Ex. 6c | | | |
|---|---|---|---|---|
| Ingredient (Trade Name) | Solid [g] | Solid [%] | Liquid [g] | Liquid [%] |
| Asenapine Base | 0.3357 | 6.097 | 0.3357 | 2.587 |
| Silicone adhesive in n-heptane. Solids content of 72.40% by weight (DOW CORNING® BIO-PSA Q7-4301) | 1.17 | 21.25 | 1.62 | 12.48 |
| Acrylate adhesive in ethyl acetate. Solids content of 50.50% by weight (DURO-TAK® 387-2287) | 4.0 | 72.65 | 7.00 | 53.95 |
| Ethyl acetate | | | 4.02 | 30.98 |
| Total | 5.5057 | 100.00 | 12.9757 | 100.00 |
| Area Weight [g/m²] | | 105.3 | | |
| Loading API [µg/cm²] | | 641.81 | | |

Preparation of the Coating Composition

A beaker was loaded with the asenapine base. The acrylic pressure sensitive adhesive was added, followed by the silicone pressure sensitive adhesive. Then the solvent was added while stirring from approx. 200 rpm to approx. 500 rpm (for Example 6b, to approx. 1000 rpm). The mixture was then stirred at approx. 1500 rpm until a homogenous mixture was obtained for approx. 150 min. For Example 6c, the solvent was added while stirring from approx. 200 rpm to approx. 1500 rpm. The mixture was then stirred at approx. 1500 rpm until a homogenous mixture was obtained for approx. 120 min.

Coating of the Coating Composition

See Example 5c for the coating process. The coating thickness gave an area weight of the matrix layer of 93.7 (6a), 130.2 (6b), and 105.3 (6c) g/m² respectively. The dried film was laminated with a polyethylene terephthalate backing layer (beige lacquered, 23 µm thickness) to provide an asenapine-containing self-adhesive layer structure.

Preparation of the TTS

See Example 1.

Measurement of Skin Permeation Rate

Figure 6:
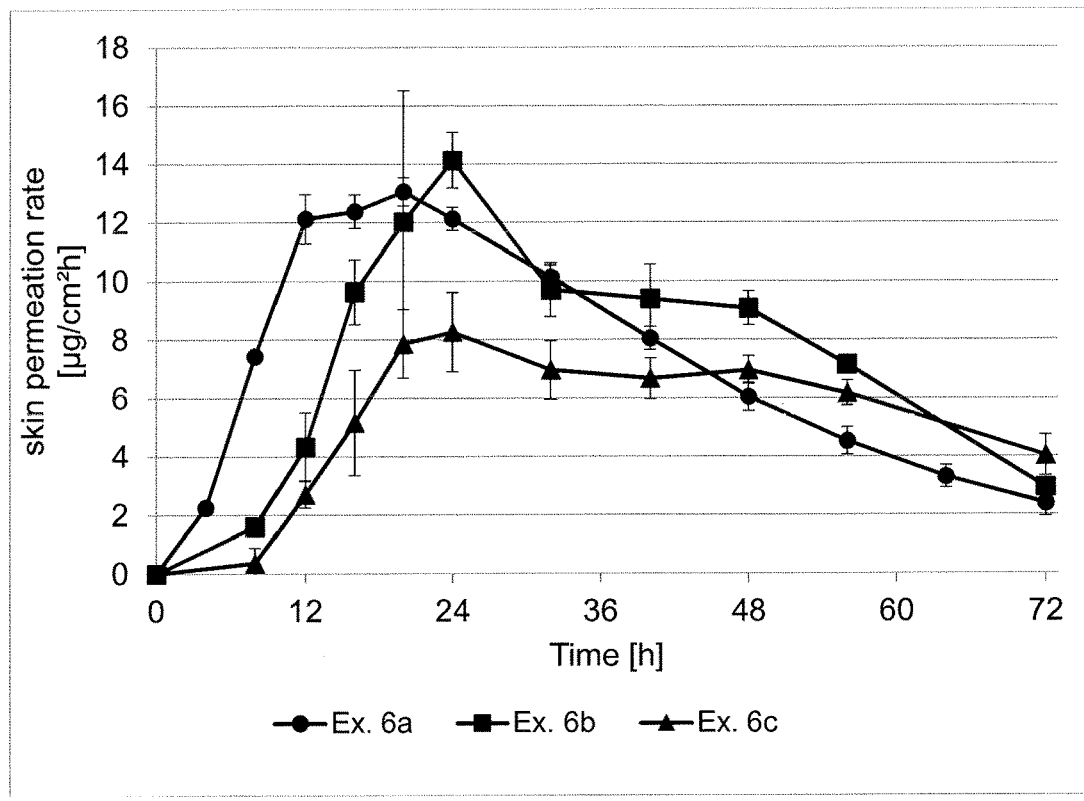
FIG. 6 depicts the asenapine skin permeation rate of TTS prepared according to Examples 6a, 6b and 6c.

The permeated amounts and the corresponding skin permeation rates of TTS prepared according to Examples 6a-c were determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 µm, with an intact epidermis for all TTS. Diecuts with an area of 1.15 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured and the corresponding skin peimeation rates calculated. The results are shown in Table 6.2 and FIG. 6.

TABLE 6.2

Skin permeation rate with SD [µg/cm²h]

| Elapsed time [h] | Ex. 6a (n = 3) Rate | SD | Ex. 6b (n = 3) Rate | SD | Ex. 6c (n = 3) Rate | SD |
|---|---|---|---|---|---|---|
| 0 | 0 | 0 | 0 | 0 | 0 | 0 |
| 4 | 2.26 | 0.19 | / | / | / | / |
| 8 | 7.43 | 0.04 | 1.61 | 0.2 | 0.37 | 0.52 |
| 12 | 12.12 | 0.84 | 4.33 | 1.16 | 2.7 | 0.45 |
| 16 | 12.38 | 0.57 | 9.63 | 1.1 | 5.16 | 1.81 |
| 20 | 13.05 | 0.48 | 12.02 | 4.49 | 7.86 | 1.18 |
| 24 | 12.12 | 0.39 | 14.12 | 0.95 | 8.26 | 1.36 |
| 32 | 10.13 | 0.42 | 9.71 | 0.92 | 6.96 | 1.01 |
| 40 | 8.05 | 0.4 | 9.4 | 1.17 | 6.67 | 0.69 |
| 48 | 6.04 | 0.48 | 9.07 | 0.58 | 6.96 | 0.47 |
| 56 | 4.52 | 0.46 | 7.16 | 0.2 | 6.17 | 0.43 |
| 64 | 3.3 | 0.39 | / | / | / | / |
| 72 | 2.39 | 0.44 | 2.94 | 0.26 | 4.03 | 0.7 |

Examples 7A, 7B

Coating Composition

The formulations of the asenapine-containing coating compositions of Examples 7a and 7b are summarized in Tables 7.1a and 7.1b below.

TABLE 7.1a

| Ingredient (Trade Name) | Ex. 7a Solid [g] | Solid [%] | Liquid [g] | Liquid [%] |
|---|---|---|---|---|
| Asenapine Base | 0.3683 | 7.268 | 0.3683 | 4.822 |
| Silicone adhesive in n-heptane. Solids content of 72.40% by weight (DOW CORNING ® BIO-PSA Q7-4301) | 4.12 | 81.31 | 5.69 | 74.50 |
| Transcutol (diethylene glycol monoethyl ether) | 0.4039 | 7.971 | 0.4039 | 5.289 |
| Kollidon 90 F (polyvinylpyrrolidone) | 0.1750 | 3.454 | 0.1750 | 2.291 |
| Ethanol | | | 1.00 | 13.09 |
| Total | 5.0672 | 100.00 | 7.6372 | 99.99 |
| Area Weight [g/m²] | | 105.5 | | |
| Loading API [µg/cm²] | | 766.8 | | |

TABLE 7.1b

| Ingredient (Trade Name) | Ex. 7b Solid [g] | Solid [%] | Liquid [g] | Liquid [%] |
|---|---|---|---|---|
| Asenapine Base | 0.3384 | 6.604 | 0.3384 | 4.822 |
| Silicone adhesive in n-heptane. Solids content of 72.40% by weight (DOW CORNING ® BIO-PSA Q7-4301) | 2.92 | 56.98 | 5.78 | 74.50 |
| Isobutylene adhesive in petroleum ether, bp 80-110° C. Solids content of 40.85% by weight (Oppanol ® B10/B100 (85:15) | 1.46 | 28.49 | 4.12 | 5.289 |
| Transcutol (diethylene glycol mono ethyl ether) | 0.4061 | 7.925 | 0.4061 | 2.291 |
| Ethyl acetate | | | 1.50 | 13.09 |
| Total | 5.1245 | 100.00 | 12.1445 | 99.99 |
| Area Weight [g/m²] | | 98.4 | | |
| Loading API [µg/cm²] | | 649.8 | | |

Preparation of the Coating Composition

For Example 7a, the coating compositions were prepared as described in Example 1. Transcutol (diethylene glycol monoethyl ether) was added before addition of the solvent. Kollidon 90 K (polyvinylpyrrolidone), was added before the addition of the silicone pressure sensitive adhesive. The mixture was stirred at approx. 200 rpm for approx. 180 min and then at approx. 1000 rpm until a homogenous mixture was obtained for approx. 50 min. For Example 7b, a beaker was loaded with the isobutylene pressure sensitive adhesive, followed by addition of the acrylic pressure sensitive adhesive. Transcutol was added while stirring at approx. 200 rpm, followed by the addition of the solvent while stirring at approx. 100 rpm. Then the asenapine base was added and the mixture was stirred at approx. 1000 rpm until a homogenous mixture was obtained for approx. 40 min.

Coating of the Coating Composition

For Example 7a, see Example 4 for the coating process. For Example 7b, see Example 5b for the coating process. The coating thickness gave an area weight of the matrix layer of 105.5 (7a) and 98.4 (7b) g/m² respectively. The dried film was laminated with a polyethylene terephthalate backing layer (beige lacquered, 23 µm thickness) to provide an asenapine-containing self-adhesive layer structure.

Preparation of the TTS

See Example 1.

Measurement of Skin Permeation Rate

Figure 7:
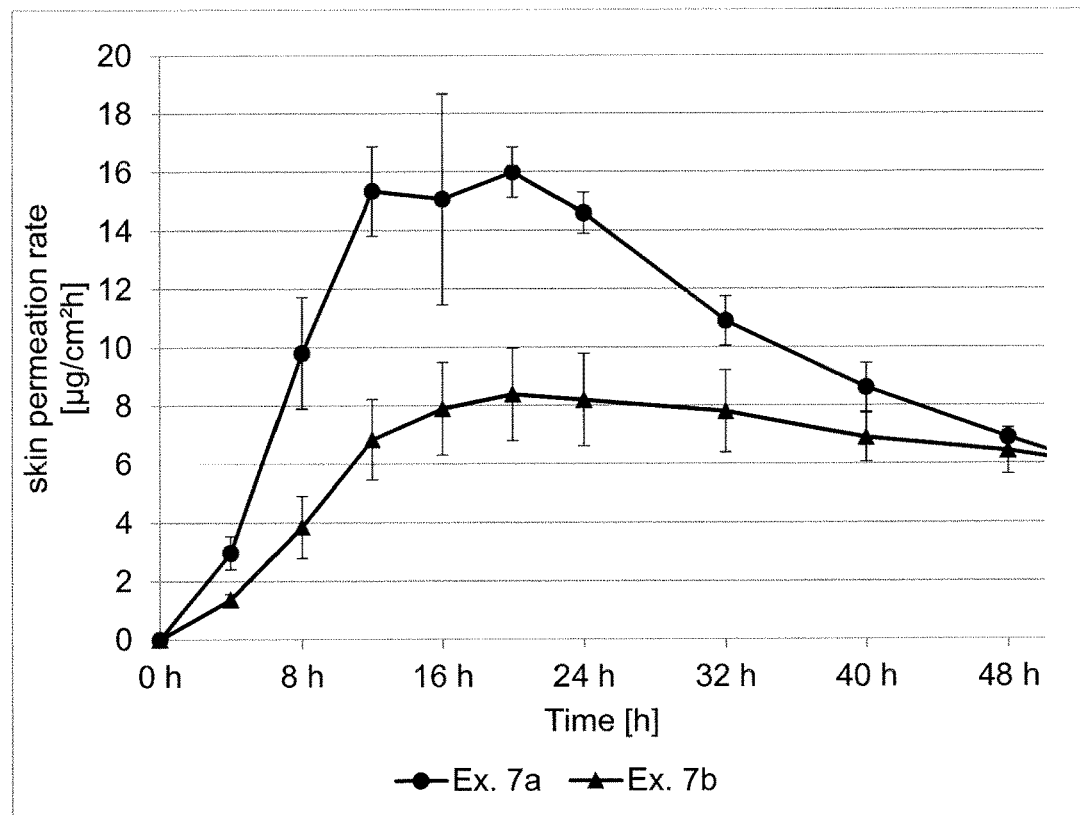
FIG. 7 depicts the asenapine skin permeation rate of TTS prepared according to Examples 7a and 7b.

The permeated amounts and the corresponding skin permeation rates of TTS prepared according to Examples 7a and 7b were determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 µm, with an intact epidermis for all TTS. Diecuts with an area of 1.16 cm² were punched from the TTS. The asenapine permeated amounts in the receptor medium of the Franz cell (phosphate buffer solution pH 5.5 with 0.1% saline azide as antibacteriological agent) at a temperature of 32±1° C. were measured and the corresponding skin permeation rates calculated. The results are shown in Table 7.2 and FIG. 7.

TABLE 7.2

| | Skin permeation rate with SD [μg/cm²h] | | | |
|---|---|---|---|---|
| Elapsed | Ex. 7a (n = 3) | | Ex. 7b (n = 3) | |
| time [h] | Rate | SD | Rate | SD |
| 0 | 0 | 0 | 0 | 0 |
| 4 | 2.97 | 0.56 | 1.37 | 0.18 |
| 8 | 9.8 | 1.92 | 3.85 | 1.06 |
| 12 | 15.34 | 1.53 | 6.83 | 1.38 |
| 16 | 15.06 | 3.6 | 7.88 | 1.59 |
| 20 | 15.98 | 0.87 | 8.38 | 1.59 |
| 24 | 14.59 | 0.7 | 8.18 | 1.59 |
| 32 | 10.89 | 0.85 | 7.79 | 1.41 |
| 40 | 8.6 | 0.84 | 6.89 | 0.84 |
| 48 | 6.9 | 0.11 | 6.42 | 0.79 |

Examples 8A, 8B

Coating Composition

The formulations of the asenapine-containing coating compositions of Examples 8a and 8b are summarized in Table 8.1a and 8.1b below.

TABLE 8.1a

| | Ex. 8a | | | |
|---|---|---|---|---|
| Ingredient (Trade Name) | Solid [g] | Solid [%] | Liquid [g] | Liquid [%] |
| Asenapine Base | 0.6711 | 6.72 | 0.6711 | 4.613 |
| Silicone adhesive in n-heptane. Solids content of 72.40% by weight (DOW CORNING ® BIO-PSA Q7-4301) | 9.3149 | 93.28 | 12.8659 | 88.444 |
| Ethyl acetate | | | 1.01 | 6.94 |
| Total | 9.986 | 100.00 | 14.547 | 100.00 |
| Area Weight [g/m²] | | 134.25 (95.2 + 39.05) | | |
| Loading API [μg/cm²] | | 902.16 | | |

TABLE 8.1b

| | Ex. 8b | | | |
|---|---|---|---|---|
| Ingredient (Trade Name) | Solid [g] | Solid [%] | Liquid [g] | Liquid [%] |
| Asenapine Base | 0.6711 | 6.72 | 0.6711 | 4.613 |
| Silicone adhesive in n-heptane. Solids content of 72.40% by weight (DOW CORNING ® BIO-PSA Q7-4301) | 9.3149 | 93.28 | 12.8659 | 88.444 |
| Ethyl acetate | | | 1.01 | 6.94 |
| Total | 9.986 | 100.00 | 14.547 | 100.00 |
| Area Weight [g/m²] | | 134.25 (95.2 + 39.05) | | |
| Loading API [μg/cm²] | | 902.16 | | |

Preparation of the Coating Composition

The coating compositions were prepared as described in Example 1. The mixture was however stirred at approx. 500 rpm until a homogenous mixture was obtained for approx. 90 min.

Coating of the Coating Composition

See Example 5c for the coating process. Two asenapine-containing matrix layer having different area weights were prepared. The thickness gave an area weight of the first matrix layer of 95.2 g/m² and an area weight of the second matrix layer of 39.05 g/m². A first and a second asenapine-containing self-adhesive layer structure were prepared.

The first layer structure was laminated with a polyethylene terephthalate backing layer (beige lacquered, 23 μm thickness) to provide an asenapine-containing self-adhesive layer structure. The second layer structure was laminated with the EVA (19%, VA) membrane 9712 (for Example 8b, EVA (9%, VA) membrane 9702 respectively). The release liner of the first layer structure was removed and this adhesive side was laminated on the EVA side of the second layer structure. This results in an asenapine-containing self-adhesive layer structure with an area weight of the matrix layer of 134.25 g/m², with a backing layer and a release liner.

Preparation of the TTS

See Example 1.

Measurement of Skin Permeation Rate

Figure 8:
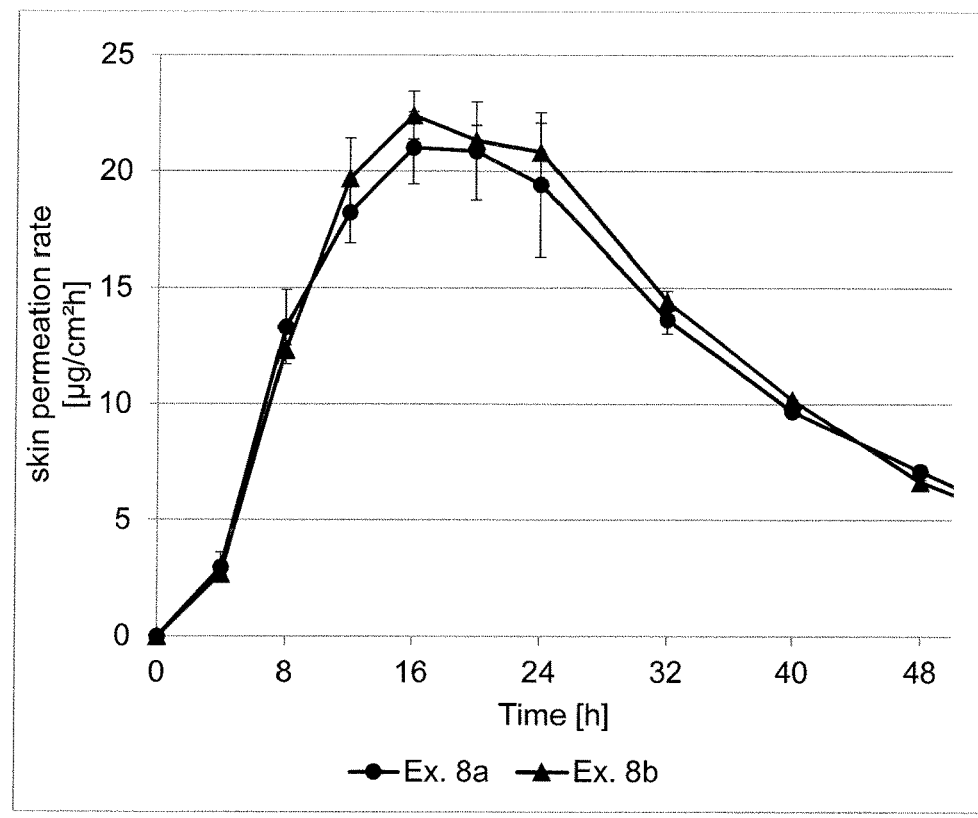
FIG. 8 depicts the asenapine skin permeation rate of TTS prepared according to Examples 8a and 8b.

The permeated amounts and the corresponding skin permeation rates of TTS prepared according to Examples 8a and 8b were determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 μm, with an intact epidermis for all TTS. Diecuts with an area of 1.15 cm² were punched from the TTS. The asenapine permeated amount in the receptor medium of the Franz cell (phosphate buffer solution pH 5.5 with 0.1% saline azide as antibacteriological agent) at a temperature of 32±1° C. were measured and the corresponding skin permeation rates calculated. The results are shown in Table 8.2 and FIG. 8.

TABLE 8.2

| | Skin permeation rate with SD [μg/cm²h] | | | |
|---|---|---|---|---|
| Elapsed | Ex. 8a (n = 3) | | Ex. 8b (n = 2) | |
| time [h] | Rate | SD | Rate | SD |
| 0 | 0 | 0 | 0 | 0 |
| 4 | 2.98 | 0.64 | 2.7 | 0.04 |
| 8 | 13.32 | 1.6 | 12.33 | 0.21 |
| 12 | 18.23 | 1.33 | 19.69 | 1.72 |
| 16 | 21.01 | 1.55 | 22.41 | 1.04 |
| 20 | 20.87 | 2.11 | 21.33 | 0.64 |
| 24 | 19.42 | 3.09 | 20.82 | 1.25 |
| 32 | 13.63 | 0.62 | 14.42 | 0.43 |
| 40 | 9.67 | 0.11 | 10.17 | 0.03 |
| 48 | 7.12 | 0.26 | 6.65 | 0.1 |

Examples 9A, 9B

Coating Composition

The formulations of the asenapine-containing coating compositions of Examples 9a and 9b are summarized in Table 9.1a and 9.1b below.

TABLE 9.1a

| | Ex. 9b | | | |
|---|---|---|---|---|
| Ingredient (Trade Name) | Solid [g] | Solid [%] | Liquid [g] | Liquid [%] |
| Asenapine Base | 0.6693 | 6.692 | 0.6693 | 4.591 |
| Silicone adhesive in n-heptane. Solids content of 72.40% by weight (DOW CORNING ® BIO-PSA Q7-4301) | 9.3328 | 93.308 | 12.8906 | 88.414 |
| Ethyl acetate | | | 1.02 | 7.00 |
| Total | 10.0021 | 100.00 | 14.5799 | 100.01 |
| Asenapine Base | 0.6693 | 6.692 | 0.6693 | 4.591 |
| Silicone adhesive in n-heptane. Solids content of 72.40% by weight (DOW CORNING ® BIO-PSA Q7-4301) | 9.3328 | 93.308 | 12.8906 | 88.414 |
| Ethyl acetate | | | 1.02 | 7.00 |
| Total | 10.0021 | 100.00 | 14.5799 | 100.01 |
| Area Weight [g/m$^2$] | 132.05 (94.15 + 37.9) | | | |
| Loading API [µg/cm$^2$] | 883.7 | | | |

TABLE 9.1b

| | Ex. 9b | | | |
|---|---|---|---|---|
| Ingredient (Trade Name) | Solid [g] | Solid [%] | Liquid [g] | Liquid [%] |
| Asenapine Base | 0.6657 | 13.154 | 0.6657 | 9.099 |
| Silicone adhesive in n-heptane. Solids content of 72.40% by weight (DOW CORNING ® BIO-PSA Q7-4301) | 4.3953 | 86.846 | 6.0708 | 82.974 |
| Ethyl acetate | | | 0.58 | 7.93 |
| Total | 5.061 | 100.00 | 7.3165 | 100.00 |
| Asenapine Base | 0.6787 | 13.577 | 0.6787 | 5.849 |
| Acrylate adhesive in ethyl acetate. Solids content of 50.50% by weight (DURO-TAK ® 387-2287) | 4.3202 | 86.423 | 8.5548 | 73.726 |
| Ethyl acetate | | | 2.37 | 20.42 |
| Total | 4.9989 | 100.00 | 11.6035 | 100.00 |
| Area Weight [g/m$^2$] | 191.2 (100.9 + 90.3) | | | |
| Loading API [µg/cm$^2$] | 2557.72 | | | |

Preparation of the Coating Composition

The coating compositions were prepared as described in Example 1. The mixture was however stirred at approx. 400 rpm until a homogenous mixture was obtained for approx. 240 min.

Coating of the Coating Composition of Example 9a

See Example 8 for the coating composition. The second matrix layer was however dried for approx. 10 min at approx. room temperature and approx. 10 min at approx. 90° C. The thickness gave an area weight of the first matrix layer of 94.15 g/m$^2$ and an area weight of the second matrix layer of 37.9 g/m$^2$. The ethylene vinyl acetate (EVA) (2% VA) membrane Co Trans 9726 was used. This results in an asenapine-containing self-adhesive layer structure with an area weight of the matrix layer of 132.05 g/m$^2$, with a backing layer and a release liner.

Coating of the Coating Composition of Example 9b

See Example 9a for the coating process, wherein the first asenapine-containing self-adhesive layer structure comprises DOW CORNING® BIO-PSA Q7-4301 (one side fluoropolymer coated, 75 µm thickness as release liner) and the second asenapine-containing self-adhesive layer structure comprises Duro-Tak™ 387-2287 (PET siliconized, 100 thickness as release liner). The coating thickness of the acrylate layer gave an area weight of the matrix layer of 100.9 g/m$^2$ and is the skin contact layer, wherein no EVA membrane is used. The coating thickness of the silicone layer gave an area weight of the matrix layer of 90.3 g/m$^2$. This results in an asenapine-containing self-adhesive layer structure with an area weight of the matrix layer of 191.2 g/m$^2$, with a backing layer and a release liner.

Preparation of the TTS

See Example 1.

Measurement of Skin Permeation Rate

Figure 9:
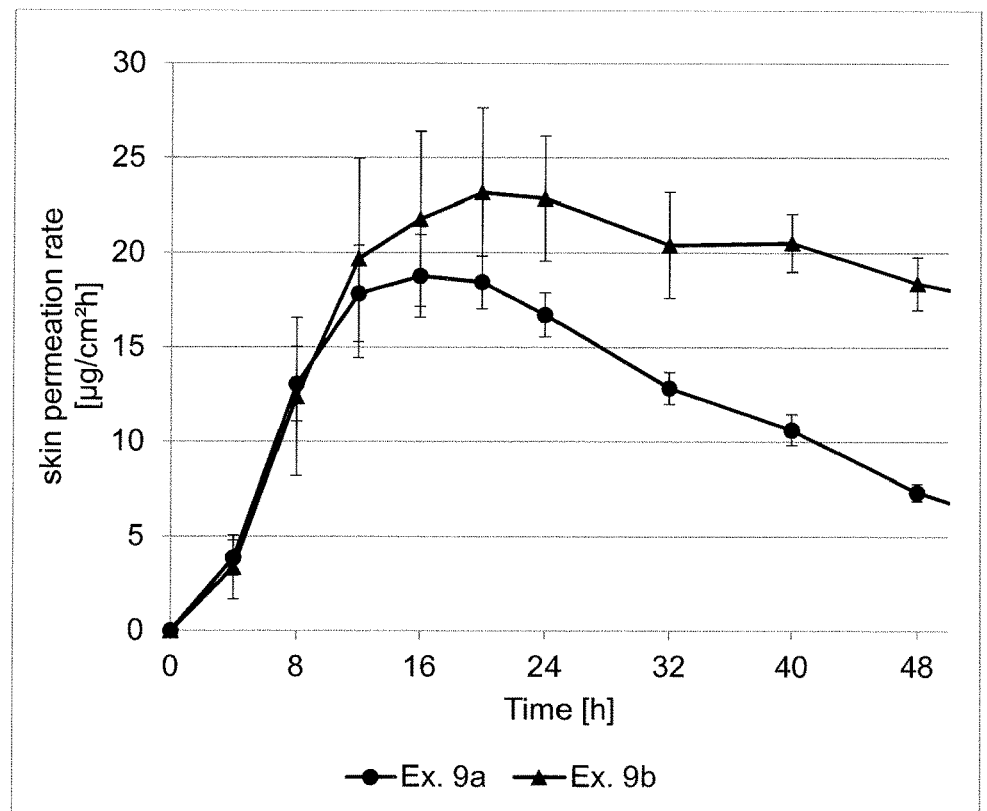
FIG. 9 depicts the asenapine skin permeation rate of TTS prepared according to Examples 9a and 9b.

The permeated amounts and the corresponding skin permeation rates of TTS prepared according to Examples 9a and 9b were determined by in vitro experiments in accordance with the OECD Guideline (adopted Apr. 13, 2004) carried out with a 10.0 ml Franz diffusion cell. Split thickness Goettingen minipig skin (female) was used. A dermatome was used to prepare skin to a thickness of 800 µm, with an intact epidermis for all TTS. Diecuts with an area of 1.16 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. were measured. The results are shown in Table 9.2 and FIG. 9.

TABLE 9.2

| | Skin permeation rate with SD [µg/cm$^2$h] | | | |
|---|---|---|---|---|
| Elapsed | Ex. 9a (n = 3) | | Ex. 9b (n = 3) | |
| time [h] | Rate | SD | Rate | SD |
| 0 | 0 | 0 | 0 | 0 |
| 4 | 3.87 | 0.93 | 3.35 | 1.69 |
| 8 | 13.04 | 1.98 | 12.37 | 4.18 |
| 12 | 17.83 | 2.56 | 19.68 | 5.27 |
| 16 | 18.76 | 2.19 | 21.77 | 4.63 |
| 20 | 18.43 | 1.39 | 23.17 | 4.47 |
| 24 | 16.71 | 1.17 | 22.85 | 3.29 |
| 32 | 12.82 | 0.85 | 20.4 | 2.79 |
| 40 | 10.63 | 0.82 | 20.52 | 1.54 |
| 48 | 7.34 | 0.45 | 18.38 | 1.4 |

Example 10

Reservoir Composition

The formulation of the asenapine-containing reservoir composition of Examples 10 is summarized in Table 10.1 below.

TABLE 10.1

| | Ex. 10 | | | |
|---|---|---|---|---|
| Ingredient (Trade Name) | Solid [g] | Solid [%] | Liquid [g] | Liquid [%] |
| Asenapine Base | 0.7224 | 3.612 | 0.7224 | 3.612 |
| Silicone Oil Q7-9120 350 CST | 16.4009 | 82.008 | 16.4009 | 82.008 |
| Transcutol (diethylene glycol monoethyl ether) | 2.8758 | 14.38 | 2.8758 | 14.38 |
| Total | 19.9991 | 100.00 | 19.9991 | 100.00 |

Preparation of the Reservoir Composition

A beaker was loaded with the asenapine base. Transcutol (diethylene glycol monoethyl ether) was added, followed by the addition of the silicone oil Q7-9120 350 CST. The mixture was first stirred at approx. room temperature at approx. 400 rpm for approx. 10 min. Then the mixture was stirred at approx. 80° C. at approx. 400 rpm until a homogenous mixture was obtained for approx. 10 min.

Preparation of the Reservoir-Type TTS

A reservoir-type TTS is formed comprising a backing layer, a strip of paper, a foam with an adhesive layer, a membrane with an adhesive layer, and a release liner. The foam is chemically inert and forms the reservoir room for the active agent. The membrane is made of PP and/or PE (Celgard 24000) with a pore size of 0.028 to 0.5%. The membrane is not a rate-controlling membrane. Thus, the liquid reservoir composition is directly applied without using a rate-controlling membrane.

In Vivo Study Using Goettingen Minipigs

The in vivo releases and the corresponding skin permeation rates of the reservoir-type TTS prepared according to Example 10 were determined by in vivo experiments using Goettingen minipigs (female, about 6 months, randomized by simple random sample method). Reservoir-type TTS with an area of 10 cm$^2$ were used, and one Goettingen minipig was used for one TTS formulation. Three drug containing and one placebo reservoir-type TTS (each 10 cm$^2$) were used per minipig. The total wear time of all 4 patches per minipig (3 active and 1 placebo) patches was 84 h.

During the study, the minipigs were kept at 22±3° C., at a relative humidity of 40±15%, lighted from 6 am to 6 pm with calorie reduced breeding food, ssniff, twice daily of about 140-200 g per animal, and with water ad libitum.

Figure 10:
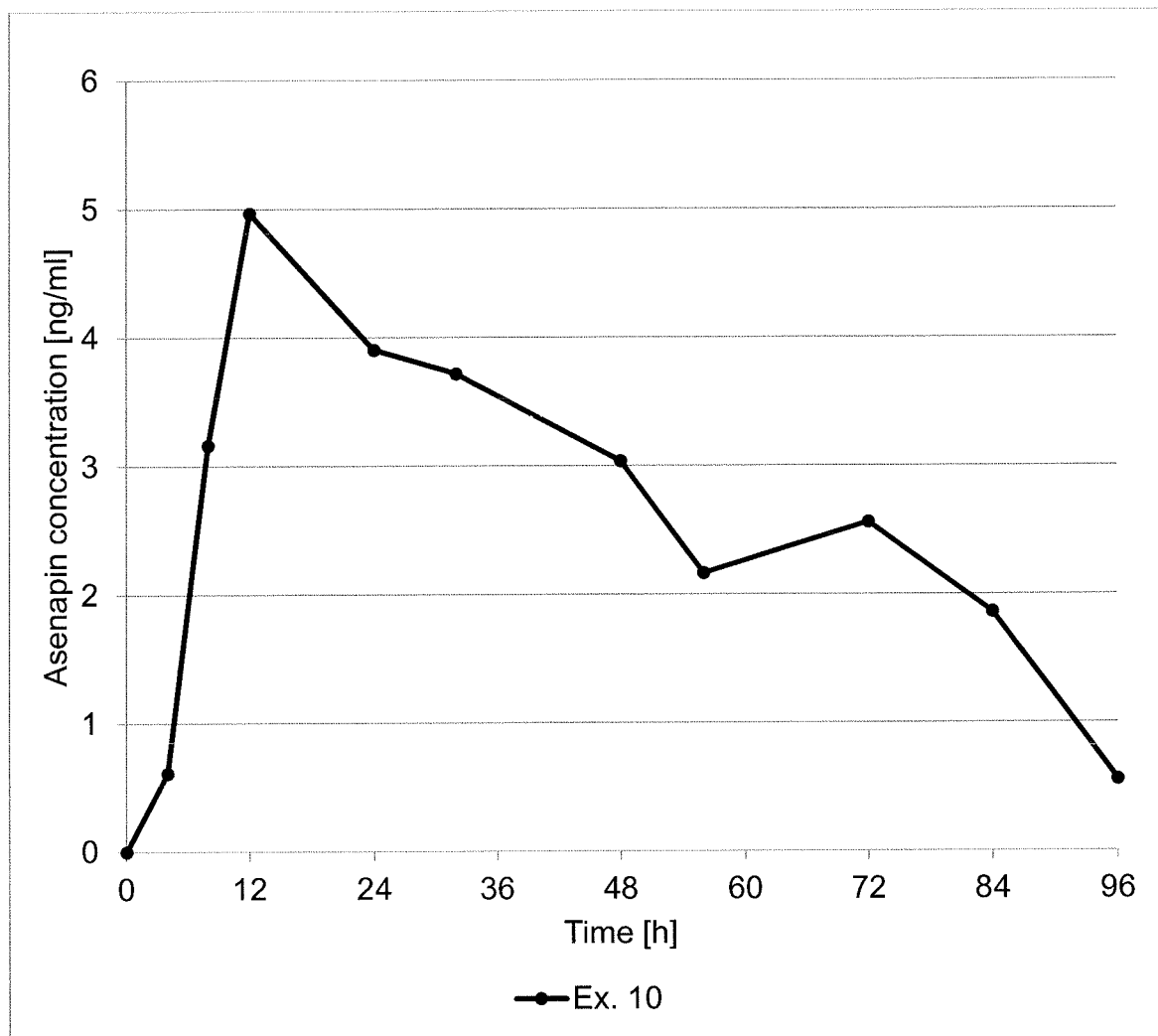
FIG. 10 depicts the ascnapinc blood plasma concentrations provided by a reservoir system comprising silicone oil prepared according to Example 10 in minipigs.

Following the above single dose application of the reservoir-type TTS (3*verum and 1 placebo, each 10 cm$^2$), 3 ml blood samples were taken at 0 h, 4 h, 8 h, 12 h, 24 h, 32 h, 48 h, 56 h, 72 h, 84 h and 96 h, and the blood samples were centrifuged 10 minutes at 2000×g in order to obtain blood plasma. The asenapine blood plasma concentration was determined by an LC method with MS/MS detection. AUC values were calculated from the blood plasma concentration. After removal of the TTS, the skin condition was macroscopically determined and a Draize score obtained based on the score scheme below. Histopathological examination of the epidermis and the dermis revealed no morphological or pathological transformation indicating an irritation of the deeper tissue layers. Histological results also show no lesion or removal of stratum corneum. The residual amount of asenapine was determined in the removed reservoir-type TTS by quantitative HPLC (see above) and the dermally delivered amount of asenapine calculated as the difference to the initial amount of asenapine included in the reservoir-type TTS. The results are shown in Table 10.2 and FIG. 10.

TABLE 10.2

| Values | Ex. 10 |
|---|---|
| AUC$_{(0-24\ h)}$ [ng/ml*h] | 78.2 |
| AUC$_{(0-96\ h)}$ [ng/ml*h] | 262.4 |
| c$_{max}$ [ng/ml] | 5.0 |
| Histopathological assessment | no important finding |
| Draize Score (3*verum/1*placebo) | 1/1/1/0 |
| Content of API in minipig skin [mg] | 0.5 |
| API content of preclinical sample [mg] | 73.9 |
| API dermal delivered [%/amount in mg] after 84 h | 69/50.7* |

*One of the three 10 cm$^2$ patches was leaking after 8 h

Example 11A-B

Coating Composition

The formulations of the asenapine-containing coating compositions of Examples 11a and Example 11b is summarized in Tables 11.1a and 11.1b below.

TABLE 11.1a

| | Ex. 11a | | | |
|---|---|---|---|---|
| Ingredient (Trade Name) | Solid [g] | Solid [%] | Liquid [g] | Liquid [%] |
| Asenapine Base | 2.1001 | 2.995 | 2.1001 | 2.056 |
| Silicone adhesive in n-heptane. Solids content of 72.40% by weight (DOW CORNING ® BIO-PSA Q7-4301) | 67.99 | 96.95 | 93.91 | 91.96 |
| α-Tocopherol | 0.0414 | 0.059 | 0.0414 | 0.041 |
| n-Heptane | | | 6.0721 | 5.946 |
| Total | 70.1315 | 100.00 | 102.1236 | 100.00 |
| Area Weight [g/m$^2$] | | 91.1 | | |
| Loading API [μg/cm$^2$] | | 272.94 | | |

TABLE 11.1b

| | Ex. 11b | | | |
|---|---|---|---|---|
| Ingredient (Trade Name) | Solid [g] | Solid [%] | Liquid [g] | Liquid [%] |
| Asenapine Base | 22.499 | 3.000 | 22.499 | 2.060 |
| Silicone adhesive in n-heptane. Solids content of 72.40% by weight (DOW CORNING ® BIO-PSA Q7-4301) | 727.21 | 96.95 | 998.92 | 91.46 |
| α-Tocopherol | 0.3739 | 0.050 | 0.3739 | 0.034 |
| n-Heptane | | | 70.40 | 6.45 |
| Total | 750.0829 | 100.00 | 1092.193 | 100.00 |
| Area Weight [g/m$^2$] | | 82.0 | | |
| Loading API [μg/cm$^2$] | | 245.9 | | |

Preparation of the Coating Composition

The coating composition was prepared in a beaker as described in Example 1, wherein, in Example 11a, the α-tocopherol was added to the asenapine before the addition of the solvent and the silicone adhesive, while in Example 11b, the asenapine is added to the α-tocopherol followed by the addition of the solvent, and then the silicone adhesive is added. The mixture was in each case stirred from approx. 250 rpm to approx. 1,000 rpm until a homogenous mixture was obtained (at least 60 min).

Coating of the Coating Composition

See Example 1 for the coating process. The coating was however dried for approx. 10 min at approx. room temperature and approx. 15 min at approx. 60° C. in case of Example 11a, and for approx. 10 min at approx. 60° C. in case of Example 11b. The coating thickness gave an area weight of the matrix layer of 91.1 g/m² in case of Example 11a and 82.0 g/m² in case of Example 11b. The dried film was in each case laminated with a polyethylene terephthalate backing layer (beige lacquered, 23 μm thickness) to provide an asenapine-containing self-adhesive layer structure.

Preparation of the TTS

See Example 1.

Measurement of Skin Permeation Rate

Figure 11:
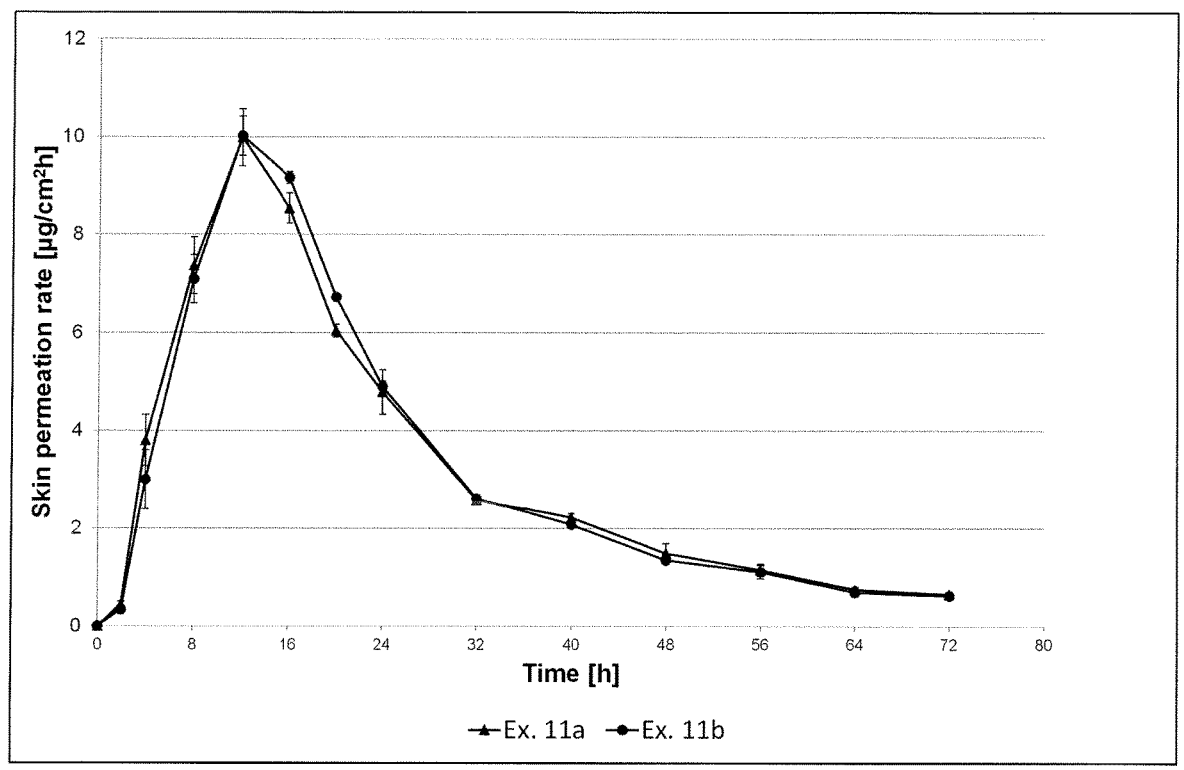
FIG. 11 depicts the asenapine skin permeation rate of TTS prepared according to Examples 11a and 11b.

The permeated amount and the corresponding skin permeation rates of TTS prepared according to Example 11a and 11b were determined by in vitro experiments in accordance with the OECD Guideline (adopted Apr. 13, 2004) carried out with a 10.0 ml Franz diffusion cell. Split thickness human skin from cosmetic surgeries (female abdomen, date of birth 1986) was used. A dermatome was used to prepare skin to a thickness of 800 μm, with an intact epidermis for all TTS. Diecuts with an area of 1.15 cm² were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 11.2 and FIG. 11.

TABLE 11.2

| Elapsed time [h] | Skin permeation rate with SD [μg/cm²h] | | | |
|---|---|---|---|---|
| | Ex. 11a (n = 3) | | Ex. 11b (n = 3) | |
| | Rate | SD | Rate | SD |
| 2 | 0.44 | 0.06 | 0.34 | 0.09 |
| 4 | 3.81 | 0.52 | 3.00 | 0.61 |
| 8 | 7.37 | 0.58 | 7.09 | 0.49 |
| 12 | 10.00 | 0.58 | 10.02 | 0.40 |
| 16 | 8.54 | 0.58 | 9.17 | 0.12 |
| 20 | 6.04 | 0.31 | 6.72 | 0.05 |
| 24 | 4.79 | 0.46 | 4.90 | 0.11 |
| 32 | 2.59 | 0.00 | 2.62 | 0.80 |
| 40 | 2.22 | 0.08 | 2.08 | 0.02 |
| 48 | 1.49 | 0.20 | 1.34 | 0.04 |
| 56 | 1.15 | 0.13 | 1.11 | 0.13 |
| 64 | 0.75 | 0.05 | 0.69 | 0.09 |
| 72 | 0.65 | 0.06 | 0.62 | 0.04 |

Example 12A-B

Coating Composition

The formulations of the asenapine-containing coating compositions of Examples 12a and Example 12b is summarized in Tables 12.1a and 12.1b below.

TABLE 12.1a

| Ingredient (Trade Name) | Ex. 12a | | | |
|---|---|---|---|---|
| | Solid [g] | Solid [%] | Liquid [g] | Liquid [%] |
| Asenapine Base | 12.0069 | 3.001 | 12.0069 | 2.040 |
| Silicone adhesive in n-heptane. Solids content of 72.40% by weight (DOW CORNING ® BIO-PSA Q7-4301) | 375.86 | 93.95 | 516.29 | 87.73 |
| α-Tocopherol | 0.1988 | 0.05 | 0.1988 | 0.034 |
| Polyvinyl-pyrrolidone (Povidone K90 F) | 12.01 | 3.00 | 12.01 | 2.04 |
| Ethanol | | | 47.9894 | 8.155 |
| Total | 400.0757 | 100.00 | 588.4951 | 100.00 |
| Area Weight [g/m²] | | 81.0 | | |
| Loading API [μg/cm²] | | 243.08 | | |

TABLE 12.1b

| Ingredient (Trade Name) | Ex. 12b | | | |
|---|---|---|---|---|
| | Solid [g] | Solid [%] | Liquid [g] | Liquid [%] |
| Asenapine Base | 12.0005 | 2.999 | 12.0005 | 2.041 |
| Silicone adhesive in n-heptane. Solids content of 72.40% by weight (DOW CORNING ® BIO-PSA Q7-4301) | 375.87 | 93.95 | 517.02 | 87.92 |
| α-Tocopherol | 0.2154 | 0.054 | 0.2154 | 0.037 |
| Polyvinyl-pyrrolidone (Povidone K90 F) | 12.0 | 3.00 | 12.00 | 2.04 |
| Ethanol | | | 46.8241 | 7.962 |
| Total | 400.0855 | 100.00 | 588.06 | 100.00 |
| Area Weight [g/m²] | | 78.9 | | |
| Loading API [μg/cm²] | | 236.52 | | |

Preparation of the Coating Composition

The coating composition was prepared in a beaker. In Example 12a, the asenapine is added to the α-tocopherol followed by the addition of the solvent, and then first the polyvinylpyrrolidone, and then the silicone adhesive is added, while in Example 12b, the silicone adhesive is added to the α-tocopherol followed by the addition of the polyvinylpyrrolidone, and then the first the asenapine, and then the solvent was added. The mixture was in each case stirred from approx. 200 rpm to approx. 2000 rpm until a homogenous mixture was obtained (at least 60 min).

Coating of the Coating Composition

See Example 1 for the coating process. The coating was however dried for approx. 10 min at approx. 80° C. in case of Example 12a, and for approx. 10 min at room temperature and for approx. 10 min at approx. 80° C. in case of Example 12b. The coating thickness gave an area weight of the matrix layer of 81.0 g/m² in case of Example 12a and 78.9 g/m² in case of Example 12b. The dried film was in each case laminated with a polyethylene terephthalate backing layer (beige lacquered, 23 μm thickness) to provide an asenapine-containing self-adhesive layer structure.

Preparation of the TTS

See Example 1.

Measurement of Skin Permeation Rate

Figure 12:
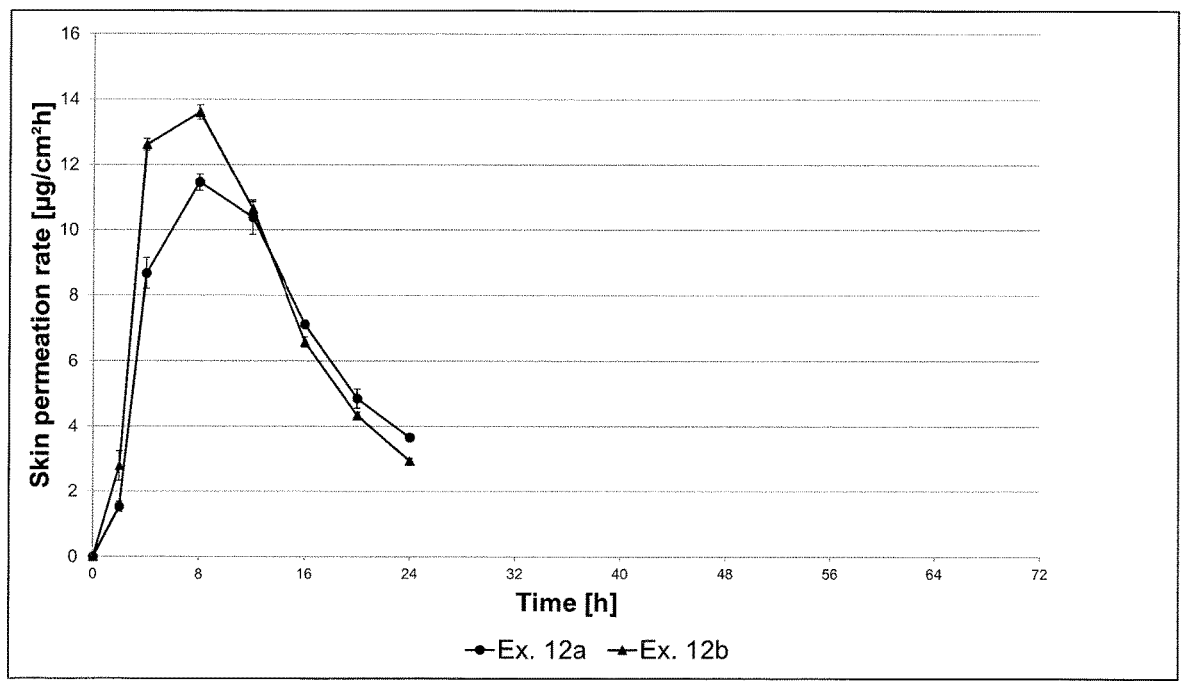
FIG. 12 depicts the asenapine skin permeation rate of TTS prepared according to Examples 12a and 12b.

The permeated amount and the corresponding skin permeation rates of TTS prepared according to Examples 12 a and 12 b were deteiinined by in vitro experiments in accordance with the OECD Guideline (adopted Apr. 13, 2004) carried out with a 10.0 ml Franz diffusion cell. Split thickness human skin from cosmetic surgeries (female leg, date of birth 1965) was used. A dermatome was used to prepare skin to a thickness of 800 μm, with an intact epidermis for all TTS. Diecuts with an area of 1.15 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 12.2 and FIG. 12.

TABLE 12.2

| | Skin permeation rate with SD [μg/cm$^2$h] | | | |
|---|---|---|---|---|
| Elapsed | Ex. 12a (n = 3) | | Ex. 12b (n = 3) | |
| time [h] | Rate | SD | Rate | SD |
| 2 | 1.53 | 0.16 | 2.79 | 0.46 |
| 4 | 8.67 | 0.46 | 12.62 | 0.18 |

TABLE 12.2-continued

| | Skin permeation rate with SD [μg/cm$^2$h] | | | |
|---|---|---|---|---|
| Elapsed | Ex. 12a (n = 3) | | Ex. 12b (n = 3) | |
| time [h] | Rate | SD | Rate | SD |
| 8 | 11.46 | 0.26 | 13.61 | 0.22 |
| 12 | 10.38 | 0.52 | 10.64 | 0.22 |
| 16 | 7.11 | 0.09 | 6.57 | 0.15 |
| 20 | 4.85 | 0.29 | 4.34 | 0.10 |
| 24 | 3.66 | 0.12 | 2.94 | 0.08 |

Examples 13A-F

Coating Composition

The formulations of the asenapine-containing coating compositions of Examples 13a-f are summarized in Table 13.1 below. The formulations are based on weight percent, as also indicated in Table 13.1.

TABLE 13.1

| | Examples 13a, 13b and 13c | | Examples 13d, 13e and 13f | |
|---|---|---|---|---|
| Ingredient (Trade Name) | Amounts [g] | Solids [%] | Amounts [g] | Solids [%] |
| Asenapine Base | 2.40 | 5.97 | 4.00 | 10.01 |
| Polyisobutylene adhesive in petroleum ether, bp 80-110° C. Solids content by 40.8% (Oppanol B10/B100 = 85/15) | 82.91 | 84.06 | 78.38 | 79.98 |
| Polyvinyl-pyrrolidone (Killidon ® 90F) | 4.01 | 9.97 | 4.01 | 10.01 |
| Ethanol | 12.03 | — | 12.18 | — |
| n-heptane | 8.15 | — | 7.47 | — |
| Total | 109.51 | — | 106.04 | — |

| | Ex. 13a | Ex. 13b | Ex. 13c | Ex. 13d | Ex 13e | Ex. 13f |
|---|---|---|---|---|---|---|
| Area Weight [g/m$^2$] | 52.8 | 129.6 | 188.4 | 51.6 | 128.2 | 185.9 |
| Asenapine content [mg/cm$^2$] | 0.32 | 0.77 | 1.12 | 0.52 | 1.28 | 1.86 |

Preparation of the Coating Composition

For Examples 13a-f, the beaker was loaded with the polyvinylpyrrolidone (Kollidon® 90 F) first and ethanol was added while stirring at approx. 100-200 rpm. The polyisobutylene adhesive was then added while stirring at approx. 400 rpm. Further, the asenapine base was added while stirring at approx. 400 rpm and finally, n-heptane was added while stirring at approx. 400-500 rpm until a homogeneous mixture was obtained.

Coating of the Coating Composition, Examples 13a-f

The resulting asenapine-containing coating composition was coated on a polyethylene terephthalate film (siliconised, 75 μm thickness, which may function as release liner) and dried for approx. 10 min-20 min at room temperature and 20 min-25 min at 80° C. The coating thickness gave an area weight of the matrix layer of 52.8 g/m$^2$ (Example 13a), 129.6 g/m$^2$ (Example 13b), 188.4 g/m$^2$ (Example 13c), 51.6 g/m$^2$ (Example 13d), 128.2 g/m$^2$ (Example 13e), and 185.9 g/m$^2$ (Example 13f), respectively. The dried film was laminated with a polyethylene terephthalate backing layer (23 μm thickness) to provide an asenapine-containing self-adhesive layer structure.

Preparation of the TTS

See Example 1.

Measurement of Skin Permeation Rate

Figure 13A:
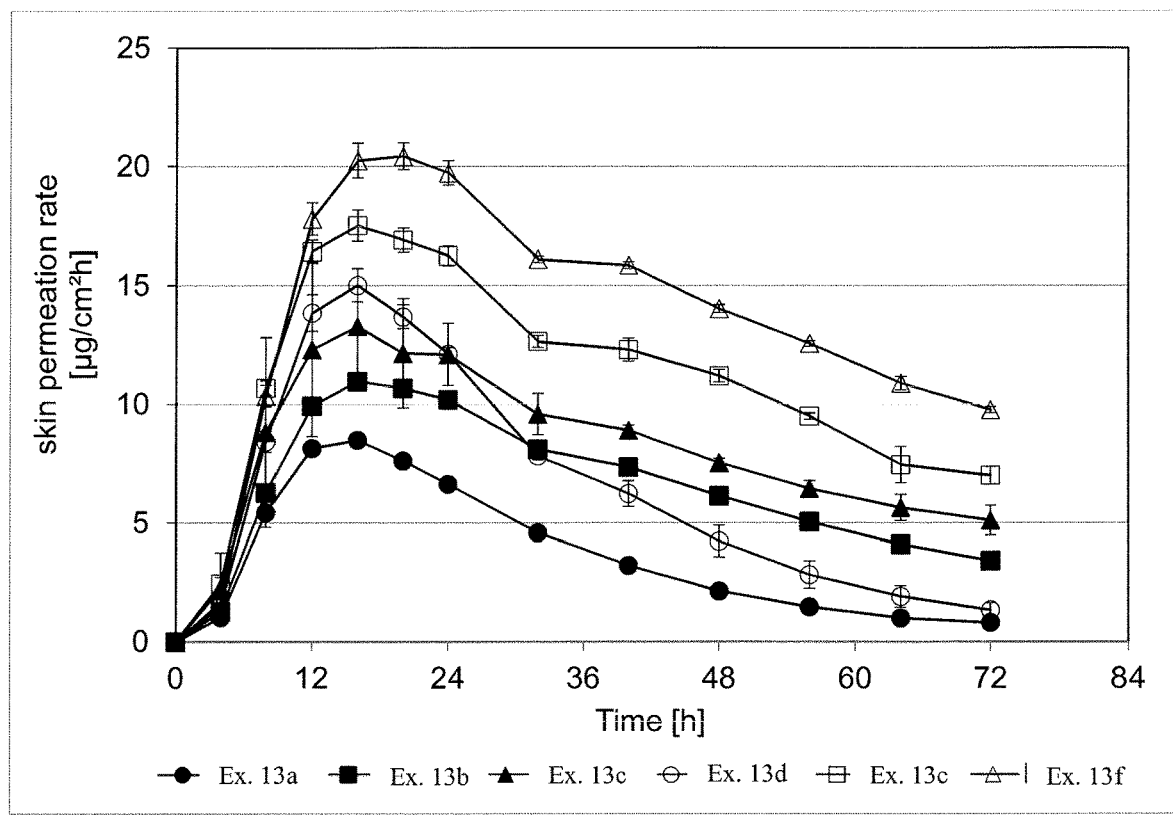
FIG. 13a and FIG. 13b depict the asenapine skin permeation rate and the substance utilization of TTS prepared according to Examples 13a-f

The permeated amount and the corresponding skin permeation rates of TTS prepared according to Examples 13a to 13f were determined by in vitro experiments in accordance with the OECD Guideline (adopted Apr. 13, 2004) carried out with a 7.0 ml Franz diffusion cell. Split thickness human skin from cosmetic surgeries (female abdomen, date of birth 1969) was used. A dermatome was used to prepare skin to a thickness of 800 μm, with an intact epidermis for all TTS. Diecuts with an area of 1.151 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Tables 13.2 and 13.3 and FIG. 13a.

TABLE 13.2

| | Skin permeation rate with SD [μg/(cm$^2$h)] | | | | | |
|---|---|---|---|---|---|---|
| Elapsed | Ex. 13a (n = 3) | | Ex. 13b (n = 3) | | Ex. 13c (n = 3) | |
| time [h] | Rate | SD | Rate | SD | Rate | SD |
| 0 | 1.04 | 0.11 | 1.28 | 0.16 | 2.25 | 1.50 |
| 4 | 5.44 | 0.18 | 6.27 | 0.31 | 8.82 | 3.99 |
| 8 | 8.15 | 0.09 | 9.93 | 0.19 | 12.31 | 3.68 |
| 12 | 8.49 | 0.21 | 10.97 | 0.07 | 13.27 | 2.44 |
| 16 | 7.62 | 0.18 | 10.68 | 0.12 | 12.15 | 2.30 |
| 20 | 6.64 | 0.06 | 10.19 | 0.14 | 12.09 | 1.31 |
| 24 | 4.59 | 0.15 | 8.10 | 0.24 | 9.59 | 0.87 |
| 32 | 3.22 | 0.18 | 7.36 | 0.05 | 8.90 | 0.21 |
| 40 | 2.14 | 0.13 | 6.14 | 0.11 | 7.53 | 0.19 |
| 48 | 1.47 | 0.12 | 5.05 | 0.04 | 6.44 | 0.33 |
| 56 | 1.01 | 0.06 | 4.11 | 0.07 | 5.65 | 0.55 |
| 64 | 0.81 | 0.02 | 3.42 | 0.08 | 5.11 | 0.63 |
| 72 | 1.04 | 0.11 | 1.28 | 0.16 | 2.25 | 1.50 |

TABLE 13.3

| | Skin permeation rate with SD [μg/(cm$^2$h)] | | | | | |
|---|---|---|---|---|---|---|
| Elapsed | Ex. 13d (n = 3) | | Ex. 13e (n = 3) | | Ex. 13f (n = 3) | |
| time [h] | Rate | SD | Rate | SD | Rate | SD |
| 0 | 1.51 | 0.28 | 2.47 | 0.27 | 1.68 | 0.12 |
| 4 | 8.42 | 0.44 | 10.69 | 0.31 | 10.35 | 0.45 |
| 8 | 13.86 | 0.77 | 16.43 | 0.48 | 17.79 | 0.68 |
| 12 | 15.01 | 0.69 | 17.51 | 0.66 | 20.25 | 0.73 |
| 16 | 13.69 | 0.50 | 16.90 | 0.51 | 20.42 | 0.56 |
| 20 | 12.12 | 0.28 | 16.25 | 0.42 | 19.73 | 0.51 |
| 24 | 7.81 | 0.17 | 12.65 | 0.25 | 16.11 | 0.14 |
| 32 | 6.23 | 0.54 | 12.31 | 0.49 | 15.86 | 0.15 |
| 40 | 4.23 | 0.67 | 11.20 | 0.26 | 14.03 | 0.16 |
| 48 | 2.82 | 0.57 | 9.50 | 0.14 | 12.56 | 0.12 |
| 56 | 1.91 | 0.45 | 7.45 | 0.77 | 10.90 | 0.28 |
| 64 | 1.35 | 0.29 | 7.00 | 0.37 | 9.77 | 0.13 |
| 72 | 1.51 | 0.28 | 2.47 | 0.27 | 1.68 | 0.12 |

Utilization of Asenapine

Figure 13B:
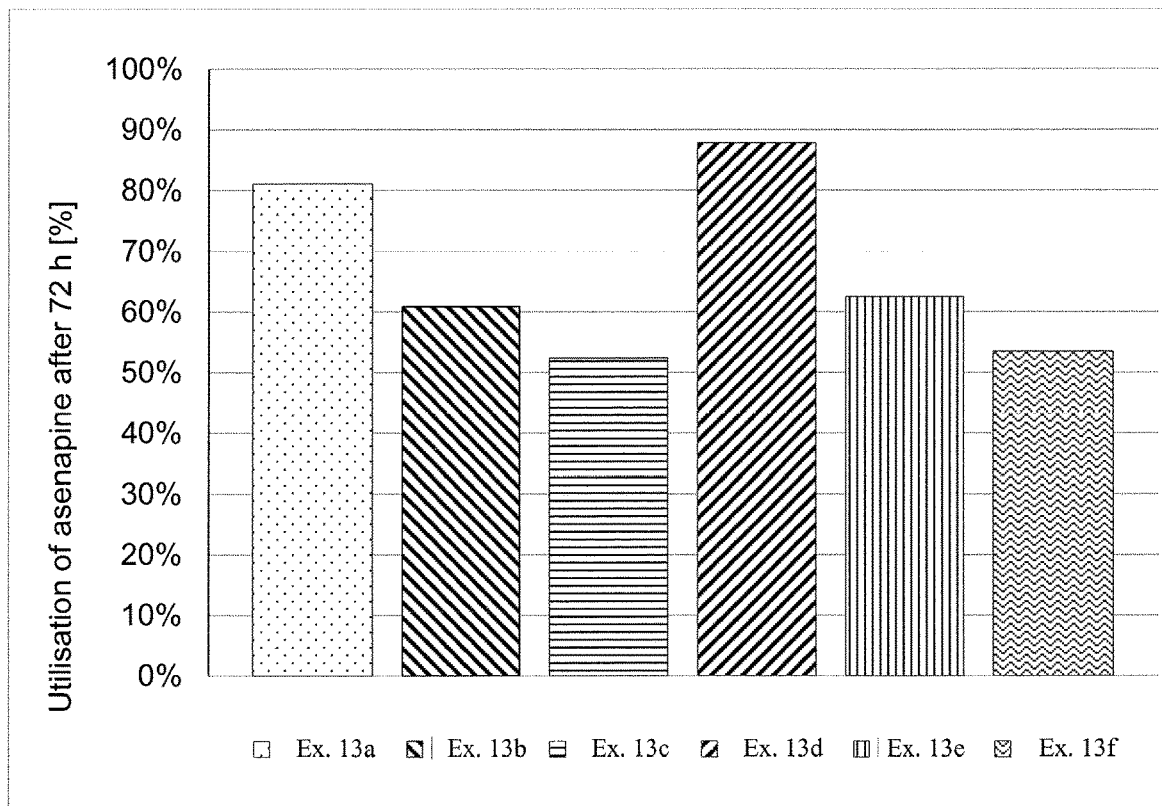

The utilization of asenapine at 72 h was calculated based on the cumulative permeated amount at 72 h and the initial asenapine content. The results are shown in Table 13.4 and in FIG. 13b.

TABLE 13.4

| Utilization of asenapine after 72 h [%] | | | | | |
|---|---|---|---|---|---|
| Example 13a (n = 3) | Example 13b (n = 3) | Example 13c (n = 3) | Example 13d (n = 3) | Example 13e (n = 3) | Example 13f (n = 3) |
| 81.02 | 60.84 | 52.40 | 87.78 | 62.49 | 53.46 |

The Invention Relates in Particular to the Following Further Items

1. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      1. asenapine in the form of the free base; and
      2. a polymer selected from the group consisting of polysiloxanes and polyisobutylenes in an amount of more than 50% by weight based on the total weight of the asenapine-containing layer;
   and
   C) optionally an additional skin contact layer.
2. Transdermal therapeutic system according to item 1, wherein the asenapine-containing layer is an asenapine-containing matrix layer.
3. Transdermal therapeutic system according to item 1, wherein the asenapine-containing layer is an asenapine-containing reservoir layer.
4. Transdermal therapeutic system according to any one of items 1 to 3, wherein the asenapine-containing layer is obtainable by incorporating the asenapine in the form of the free base.
5. Transdermal therapeutic system according to any one of items 1 to 4, wherein at least 90 mol %, preferably at least 95 mol %, more preferably at least 99 mol % of the asenapine in the asenapine-containing layer are present in the form of the free base.

6. Transdermal therapeutic system according to any one of items 1 to 5, wherein the amount of asenapine in the asenapine-containing layer ranges from 1 to 10%, preferably from 2 to 7% by weight based on the total weight of the asenapine-containing layer.

7. Transdermal therapeutic system according to any one of items 1 to 6, wherein the amount of asenapine contained in the transdermal therapeutic system ranges from 3 to 21 mg, preferably from 3.5 to 14 mg.

8. Transdermal therapeutic system according to any one of items 1 to 7, wherein the asenapine has a purity of at least 95%, preferably at least 98% and more preferably at least 99% as determined by quantitative HPLC.

9. Transdermal therapeutic system according to any one of items 1 to 8, wherein the amount of the polymer ranges from 55 to 98%, preferably from 70 to 98% or from 80 to 98% by weight based on the total weight of the asenapine-containing layer.

10. Transdermal therapeutic system according to any one of items 1 to 9, wherein the polymer is a pressure-sensitive adhesive polymer.

11. Transdermal therapeutic system according to any one of items 1 to 10, wherein the polymer is a polysiloxane.

12. Transdermal therapeutic system according to any one of items 1 to 10, wherein the polymer is a polyisobutylene.

13. Transdermal therapeutic system according to any one of items 1 to 12, wherein the asenapine-containing layer further comprises at least one additive or excipient selected from crystallization inhibitors, solubilizers, fillers, substances for skincare, pH regulators, preservatives, tackifiers, softeners, stabilizers, and permeation enhancers, in particular from crystallization inhibitors, substances for skincare, tackifiers, softeners, stabilizers, and permeation enhancers.

14. Transdermal therapeutic system according to any one of items 1 to 13, wherein the asenapine-containing layer further comprises a crystallization inhibitor, wherein the crystallization inhibitor is preferably polyvinylpyrrolidone, more preferably soluble polyvinylpyrrolidone.

15. Transdermal therapeutic system according to any one of items 1 to 14, wherein the asenapine-containing layer further comprises a stabilizer, wherein the stabilizer is preferably selected from tocopherol and ester derivatives thereof and ascorbic acid and ester derivatives thereof.

16. Transdermal therapeutic system according to any one of items 1 to 15, wherein the asenapine-containing layer further comprises a permeation enhancer, wherein the permeation enhancer is preferably selected from diethylene glycol monoethyl ether (transcutol), diisopropyl adipate, isopropyl myristate, isopropyl palmitate, lauryl lactate, and dimethylpropylene urea.

17. Transdermal therapeutic system according to any one of items 1 to 16, wherein the asenapine-containing layer does not comprise isopropyl palmitate.

18. Transdermal therapeutic system according to any one of items 1 to 17, wherein the asenapine-containing layer does not comprise a permeation enhancer selected from oleic acids, oleic alcohols, and triglycerides.

19. Transdermal therapeutic system according to any one of items 1 to 18, wherein the asenapine-containing layer does not comprise a permeation enhancer.

20. Transdermal therapeutic system according to any one of items 1 to 19, wherein the asenapine-containing layer further comprises a copolymer based on dimethylaminoethyl methacrylate, butyl methacrylate and methyl methacrylate.

21. Transdermal therapeutic system according to any one of items 1 to 20, wherein the area of release ranges from 5 to 60 cm$^2$, preferably from 10 to 40 cm$^2$.

22. Transdermal therapeutic system according to any one of items 1 to 21, wherein the area weight of the asenapine-containing layer ranges from 50 to 120 g/m$^2$, preferably from 70 to 100 g/m$^2$.

23. Transdermal therapeutic system according to any one of items 1 to 22, wherein the transdermal therapeutic system provides a skin permeation rate of asenapine as measured in a Franz diffusion cell with dermatomed human skin of
   0 μg/(cm$^2$*h) to 12 μg/(cm$^2$*h) in the first 4 hours,
   1 μg/(cm$^2$*h) to 22 μg/(cm$^2$*h) from hour 4 to hour 8,
   6 μg/(cm$^2$*h) to 25 μg/(cm$^2$*h) from hour 8 to hour 12,
   5 μg/(cm$^2$*h) to 20 μg/(cm$^2$*h) from hour 12 to hour 16,
   4 μg/(cm$^2$*h) to 18 μg/(cm$^2$*h) from hour 16 to hour 20,
   2 μg/(cm$^2$*h) to 12 μg/(cm$^2$*h) from hour 20 to hour 24.

24. Transdermal therapeutic system according to any one of items 1 to 23, wherein the transdermal therapeutic system provides a cumulative permeated amount of asenapine as measured in a Franz diffusion cell with dermatomed human skin of 120 μg/cm$^2$ to 380 μg/cm$^2$ over a time period of 24 hours.

25. Transdermal therapeutic system according to any one of items 1 to 24, wherein the transdermal therapeutic system provides a permeated amount of asenapine as measured in a Franz diffusion cell with dermatomed human skin of
   0 μg/cm$^2$ to 50 μg/cm$^2$ in the first 4 hours,
   20 μg/cm$^2$ to 120 μg/cm$^2$ from hour 4 to hour 8,
   40 μg/cm$^2$ to 220 μg/cm$^2$ from hour 8 to hour 12,
   60 μg/cm$^2$ to 290 μg/cm$^2$ from hour 12 to hour 16,
   80 μg/cm$^2$ to 340 μg/cm$^2$ from hour 16 to hour 20,
   100 μg/cm$^2$ to 380 μg/cm$^2$ from hour 20 to hour 24.

26. Transdermal therapeutic system according to any one of items 1 to 25, wherein the transdermal therapeutic system provides a mean release rate of from 0.5 to 20 mg/day, preferably from 3 to 10 mg/day, more preferably of from 3 to 8 mg/day asenapine over at least 24 hours of administration.

27. Transdermal therapeutic system according to any one of items 1 to 26, wherein the transdermal therapeutic system provides by passive transdermal delivery an $AUC_{0\text{-}24}$ from 5 to 100 (ng/mL)*h.

28. Transdermal therapeutic system according to any one of items 1 to 27, wherein the transdermal therapeutic system provides by passive transdermal delivery an $AUC_{0\text{-}24}$ from 10 to 90 (ng/mL)*h.

29. Transdermal therapeutic system according to any one of items 1 to 28, wherein the transdermal therapeutic system further comprises a release liner.

30. Transdermal therapeutic system according to any one of items 1 to 29, wherein the transdermal therapeutic system further comprises an adhesive overlay.

31. Transdermal therapeutic system according to any one of items 1 to 30, wherein the backing layer is substantially asenapine-impermeable.

32. Transdermal therapeutic system according to any one of items 1 to 31, wherein the transdermal therapeutic system comprises an additional skin contact layer.

33. Transdermal therapeutic system according to any one of items 1 to 32, wherein the transdermal therapeutic system does not comprise an additional skin contact layer.

34. Transdermal therapeutic system according to any one of items 1 to 33 for use in a method of treating a human patient.

35. Transdermal therapeutic system according to any one of items 1 to 34 lbr use in a method of treating bipolar disorder and/or schizophrenia, preferably bipolar disorder and in particular acute manic or mixed episodes of bipolar disorder.

36. Transdermal therapeutic system for use according to item 34 or 35, wherein the transdermal therapeutic system is applied to the skin of the patient for a dosing interval of from 20 to 30 hours, preferably of about 24 hours.

37. Method of treating a human patient by applying a transdermal therapeutic system as defined in any one of items 1 to 33 to the skin of the patient.

38. Method of treating bipolar disorder and/or schizophrenia, preferably bipolar disorder and in particular acute manic or mixed episodes of bipolar disorder by applying a transdermal therapeutic system as defined in any one of items 1 to 33 to the skin of the patient.

39. Method of treatment according to item 37 or 38, wherein the transdermal therapeutic system is applied to the skin of the patient for a dosing interval of from 20 to 30 hours, preferably of about 24 hours.

40. A process for manufacturing an asenapine-containing layer for use in a transdermal therapeutic system according to any one of items 1 to 33 comprising the steps of:
   1) combining at least the components
      1. asenapine in the form of asenapine base;
      2. a polymer selected from the group consisting of polysiloxanes and polyisobutylenes in an amount of more than 50% by weight based on the total weight of the asenapine-containing layer; and
      3. optionally at least one additive;
      to obtain a coating composition;
   2) coating the coating composition onto the backing layer or release liner or any intermediate liner; and
   3) drying the coated coating composition to form the asenapine-containing layer.

41. Process for manufacturing an asenapine-containing layer according to item 40, wherein the polymer is provided as a solution, wherein the solvent is selected from alcoholic solvents, in particular methanol, ethanol, isopropanol and mixtures thereof, and from non-alcoholic solvents, in particular ethyl acetate, hexane, heptane, petroleum ether, toluene, and mixtures thereof, and more preferably is selected from non-alcoholic solvents and most preferably is ethyl acetate or n-heptane.

42. Process for manufacturing an asenapine-containing layer according to item 40 or 41, wherein the polymer is polysiloxane, which is provided as a solution preferably as a solution in n-heptane or ethyl acetate with a solids content of from 60 to 80% by weight.

43. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing matrix layer comprising:
      1. asenapine in the form of the free base;
      2. a polysiloxane in an amount of at least 50% by weight based on the total weight of the asenapine-containing layer; and
      3. a stabilizer; and
      4. a crystallization inhibitor;
   and
   C) optionally an additional skin contact layer.

44. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing matrix layer comprising:
      1. asenapine in the form of the free base in an amount of 2 to 7% by weight based on the total weight of the asenapine-containing layer;
      2. a polysiloxane in an amount of from 85 to 98% by weight based on the total weight of the asenapine-containing layer; and
      3. a stabilizer in an amount of from 0.01 to 1.0% by weight based on the total weight of the asenapine-containing layer; and
      4. crystallization inhibitor in an amount of from 0.5 to 10% by weight based on the total weight of the asenapine-containing layer;
   and
   C) optionally an additional skin contact layer;
   wherein the area weight of the matrix layer ranges from 70 to 100 g/m².

45. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing matrix layer comprising:
      1. asenapine in the form of the free base in an amount of 2 to 7% by weight based on the total weight of the asenapine-containing layer;
      2. a polysiloxane in an amount of from 85 to 98% by weight based on the total weight of the asenapine-containing layer; and
      3. tocopherol in an amount of from 0.01 to 1.0% by weight based on the total weight of the asenapine-containing layer; and
      4. polyvinylpyrrolidone in an amount of from 0.5 to 10% by weight based on the total weight of the asenapine-containing layer;
   and
   C) optionally an additional skin contact layer;
   wherein the area weight of the matrix layer ranges from 70 to 100 g/m².

46. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      1. asenapine in an amount of from 2 to 7% by weight based on the total weight of the asenapine-containing layer; and
      2. at least one silicone polymer in an amount of from 85 to 98% by weight based on the total weight of the asenapine-containing layer;
   and
   C) optionally an additional skin contact layer.

47. The transdermal therapeutic system according to item 46, wherein the self-adhesive layer structure comprises
   A) a backing layer;
   B) an asenapine-containing layer, which is an asenapine-containing matrix layer, comprising:
      1. asenapine in an amount of 2 to 7% by weight based on the total weight of the asenapine-containing layer;
      2. at least one silicone polymer in an amount of from 85 to 98% by weight based on the total weight of the asenapine-containing layer; and
      3. a stabilizer in an amount of from 0.01 to 1.0% by weight based on the total weight of the asenapine-containing layer; and
      4. a crystallization inhibitor in an amount of from 0.5 to 10% by weight based on the total weight of the asenapine-containing layer;
   and
   C) optionally an additional skin contact layer.

48. The transdermal therapeutic system according to item 47, wherein the area weight of the asenapine-containing layer ranges from 50 to 120 g/m², preferably from 70 to 100 g/m².

49. The transdermal therapeutic system according to item 48, wherein the stabilizer is tocopherol, ascorbyl palmitate or a combination thereof, and/or the crystallization inhibitor is polyvinylpyrrolidone.

50. The transdermal therapeutic system according to any one of items 46 to 49, wherein the asenapine is in the form of the free base.

51. The transdermal therapeutic system according to any one of items 46 to 50, wherein the silicone polymer is obtainable by polycondensation of silanol endblocked polydimethylsiloxane with a silicate resin.

52. The transdermal therapeutic system according to item 51, wherein the ratio of the silanol endblocked polydimethylsiloxane to the silicate resin is in the range of from 70:30 to 50:50, preferably from 56:44 to 54:46, e.g. about 55:45.

53. The transdermal therapeutic system according to item 51 or 52, wherein the residual functionality of the at least one silicone polymer is capped with trimethylsiloxy groups.

54. The transdermal therapeutic system according to any one of items 46 to 53, which is for use in a method of treating a human patient.

55. The transdermal therapeutic system according to any one of items 46 to 53, which is for use in a method of treating bipolar disorder and/or schizophrenia, preferably bipolar disorder and in particular acute manic disorder or mixed episodes of bipolar disorder.

56. The transdermal therapeutic system for use according to item 54 or 55, wherein the transdermal therapeutic system is applied to the skin of the patient for a dosing interval of from 20 to 30 hours, preferably of about 24 hours.

57. A process for manufacturing an asenapine-containing layer for use in a transdermal therapeutic system according to any one of items 46 to 53 comprising the steps of:
   1) combining at least the components
      1. asenapine in an amount of from 2 to 7% by weight based on the total weight of the asenapine-containing layer;
      2. at least one silicone polymer in an amount of from 85 to 98% by weight based on the total weight of the asenapine-containing layer; and
      3. optionally a stabilizer; and
      4. optionally a crystallization inhibitor;
      to obtain a coating composition;
   2) coating the coating composition onto the backing layer or release liner or any intermediate liner; and
   3) drying the coated coating composition to form the asenapine-containing layer.

58. Transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      1. asenapine in an amount of from 2 to 15% by weight based on the total weight of the asenapine-containing layer; and
      2. at least one polyisobutylene in an amount of from 70 to 98% by weight based on the total weight of the asenapine-containing layer;
   and
   C) optionally an additional skin contact layer.

59. The transdermal therapeutic system according to item 58, wherein the self-adhesive layer structure comprises
   A) a backing layer;
   B) an asenapine-containing layer, which is an asenapine-containing matrix layer, comprising:
      1. asenapine in an amount of from 2 to 15% by weight based on the total weight of the asenapine-containing layer; and
      2. at least one polyisobutylene in an amount of from 70 to 98% by weight based on the total weight of the asenapine-containing layer; and
      3. a hydrophilic polymer in an amount of from 1 to 20% by weight based on the total weight of the asenapine-containing layer;
   and
   C) optionally an additional skin contact layer.

60. The transdermal therapeutic system according to item 58 or 59, wherein the self-adhesive layer structure comprises
   A) a backing layer;
   B) an asenapine-containing layer, which is an asenapine-containing matrix layer, comprising:
      1. asenapine in an amount of from 4 to 12% by weight based on the total weight of the asenapine-containing layer; and
      2. at least one polyisobutylene in an amount of from 70 to 90% by weight based on the total weight of the asenapine-containing layer; and
      3. a hydrophilic polymer in an amount of from 5 to 15% by weight based on the total weight of the asenapine-containing layer;
   and
   C) optionally an additional skin contact layer.

61. The transdermal therapeutic system according to any one of items 58 to 60, wherein the area weight of the asenapine-containing layer ranges from 40 to 250 g/m².

62. The transdermal therapeutic system according to any one of items 59 to 61, wherein the hydrophilic polymer is polyvinylpyrrolidone.

63. The transdermal therapeutic system according to any one of items 58 to 62, wherein the asenapine is in the form of the free base.

64. The transdermal therapeutic system according to any one of items 58 to 63, wherein the at least one polyisobutylene is a combination of a low molecular weight polyisobutylene and a high molecular weight polyisobutylene in a ratio of from 99:1 to 50:50, preferably from 90:10 to 60:40.

65. The transdermal therapeutic system according to item 64, wherein the low molecular weight polyisobutylene has a viscosity average molecular weight of from 38,000 to 42,000 g/mol and/or a weight average molecular weight of from 34,000 to 40,000 g/mol, and wherein the high molecular weight polyisobutylene has a viscosity average molecular weight of from 1,100,000 to 1,120,000 g/mol and/or a weight average molecular weight of from 1,540,000 to 1,560,000 g/mol.

66. The transdermal therapeutic system according to any one of items 58 to 65, which is for use in a method of treating a human patient.

67. The transdermal therapeutic system according to any one of items 58 to 65, which is for use in a method of treating bipolar disorder and/or schizophrenia, preferably bipolar disorder and in particular acute manic disorder or mixed episodes of bipolar disorder.

68. The transdermal therapeutic system for use according to item 66 or 67, wherein the transdermal therapeutic system has an area weight of from 40 to 125 g/m², preferably from 60 to 100 g/m², and is applied to the skin of the patient for a dosing interval of from 20 to 30 hours, preferably of about 24 hours.

69. The transdermal therapeutic system for use according to item 66 or 67, wherein the transdermal therapeutic system has an area weight of from more than 125 to 250 g/m², preferably from 150 to 250 g/m² and is applied to the skin of the patient for a dosing interval of at least 72 hours, preferably of about 84 hours.
70. A process for manufacturing an asenapine-containing layer for use in a transdermal therapeutic system according to any one of items 58 to 65 comprising the steps of:
1) combining at least the components
   1. asenapine in an amount of from 2 to 15% by weight based on the total weight of the asenapine-containing layer;
   2. at least one polyisobutylene in an amount of from 70 to 98% by weight based on the total weight of the asenapine-containing layer; and
   3. optionally a hydrophilic polymer;
   to obtain a coating composition;
2) coating the coating composition onto the backing layer or release liner or any intermediate liner; and
3) drying the coated coating composition to form the asenapine-containing layer.

The Invention Further Relates in Particular to the Following Embodiments

1. Transdeiiiial therapeutic system for the transdermal administration of asenapine comprising a self-adhesive layer structure comprising a therapeutically effective amount of asenapine, said self-adhesive layer structure comprising:
   a) a backing layer;
   b) an asenapine-containing layer comprising:
      (i) asenapine in the form of the free base; and
      (ii) more than 50% by weight of a polymer selected from the group consisting of polysiloxanes and polyisobutylenes;
   and
   c) optionally an additional skin contact layer.
2. Transdermal therapeutic system according to embodiment 1, wherein the asenapine-containing layer is an asenapine-containing matrix layer.
3. Transdermal therapeutic system according to embodiment 1, wherein the asenapine-containing layer is an asenapine-containing reservoir layer.
4. Transdermal therapeutic system according to any one of embodiments 1 to 3, wherein the asenapine-containing layer is obtainable by incorporating the asenapine in the foiiu of the free base.
5. Transdermal therapeutic system according to any one of embodiments 1 to 4, wherein at least 90 mol %, preferably at least 95 mol %, more preferably at least 99 mol % of the asenapine in the asenapine-containing layer are present in the form of the free base.
6. Transdermal therapeutic system according to any one of embodiments 1 to 5, wherein the amount of asenapine in the asenapine-containing layer ranges from 1 to 10%, preferably from 2 to 7% by weight based on the total weight of the asenapine-containing layer.
7. Transdeiinal therapeutic system according to any one of embodiments 1 to 6, wherein the amount of asenapine contained in the transdermal therapeutic system ranges from 3 to 21 mg, preferably from 3.5 to 14 mg.
8. Transdermal therapeutic system according to any one of embodiments 1 to 7, wherein the amount of the polymer ranges from 55 to 98%, preferably from 70 to 98% or from 80 to 98% by weight based on the total weight of the asenapine-containing layer.
9. Transdermal therapeutic system according to any one of embodiments 1 to 8, wherein the polymer is a pressure-sensitive adhesive polymer.
10. Transdermal therapeutic system according to any one of embodiments 1 to 9, wherein the polymer is a polysiloxane.
11. Transdermal therapeutic system according to any one of embodiments 1 to 9, wherein the polymer is a polyisobutylene.
12. Transdermal therapeutic system according to any one of embodiments 1 to 11 for use in a method of treating a human patient.
13. Transdermal therapeutic system according to any one of embodiments 1 to 12 for use in a method of treating bipolar disorder and/or schizophrenia, preferably bipolar disorder and in particular acute manic or mixed episodes of bipolar disorder.
14. Transdermal therapeutic system for use according to embodiment 12 or 13, wherein the transdermal therapeutic system is applied to the skin of the patient for a dosing interval of from 20 to 30 hours, preferably of about 24 hours.
15. A process for manufacturing an asenapine-containing layer for use in a transdermal therapeutic system according to any one of embodiments 1 to 11 comprising the steps of:
1) combining at least the components
   (i) asenapine in the form of asenapine base;
   (ii) a polymer selected from the group consisting of polysiloxanes and polyisobutylenes in an amount of more than 50% by weight based on the total weight of the asenapine-containing layer; and
   (iii) optionally at least one additive;
   to obtain a coating composition;
2) coating the coating composition onto the backing layer or release liner or any intermediate liner; and
3) drying the coated coating composition to form the asenapine-containing layer.
16. Transdermal therapeutic system according to any one of embodiments 1-14, wherein the asenapine-containing layer further comprises at least one excipient selected from the group consisting of crystallization inhibitors, solubilizers, fillers, substances for skincare, pH regulators, preservatives, tackifiers, softeners, stabilizers, and permeation enhancers.
17. Transdermal therapeutic system according to embodiment 16, wherein the asenapine-containing layer comprises a stabilizer in an amount of 0.01 to 1.0% by weight based on the total weight of the asenapine-containing layer, and a crystallization inhibitor in an amount of 0.5 to 10% by weight based on the total weight of the asenapine-containing layer.
18. Transdermal therapeutic system according to embodiment 2, wherein the asenapine-containing matrix layer comprises:
   (ii) asenapine in the form of the free base;
   (iii) a polysiloxane in an amount of at least 50% by weight based on the total weight of the asenapine-containing layer;
   (iv) tocopherol; and
   (v) polyvinylpyrrolidone.
19. Transdermal therapeutic system according to embodiment 18, wherein the asenapine-containing matrix layer comprises:
   (ii) asenapine in the form of the free base in an amount of 2 to 7% by weight based on the total weight of the asenapine-containing matrix layer;
   (iii) a polysiloxane in an amount of 85 to 98% by weight based on the total weight of the asenapine-containing matrix layer;

(iv) tocopherol in an amount of 0.01 to 1.0% by weight based on the total weight of the asenapine-containing matrix layer; and (v) polyvinylpyrrolidone in an amount of 0.5 to 10% by weight based on the total weight of the asenapine-containing matrix layer;

wherein the area weight of the matrix layer ranges from 70 to 100 g/m².

20. A method of treating schizophrenia in a patient in need thereof, the method comprising administering to the patient a transdermal therapeutic system comprising an asenapine-containing self-adhesive layer structure, said self-adhesive layer structure comprising:

a) a backing layer; and b) an asenapine-containing matrix layer comprising:

(i) a therapeutically effective amount of asenapine free base; and (ii) at least 50% by weight of a polymer selected from the group consisting of polysiloxanes and polyisobutylenes.

21. The method according to embodiment 20, wherein the asenapine-containing matrix layer further comprises at least one excipient selected from the group consisting of crystallization inhibitors, solubilizers, fillers, substances for skincare, pH regulators, preservatives, tackifiers, softeners, stabilizers, and permeation enhancers.

22. The method according to any of embodiments 20 or 21, wherein the asenapine-containing matrix layer comprises:

(i) asenapine in the form of the free base in an amount of 2 to 7% by weight based on the total weight of the asenapine-containing matrix layer;

(ii) a polysiloxane in an amount of 85 to 98% by weight based on the total weight of the asenapine-containing matrix layer;

(iii) tocopherol in an amount of 0.01 to 1.0% by weight based on the total weight of the asenapine-containing matrix layer; and (iv) polyvinylpyrrolidone in an amount of 0.5 to 10% by weight based on the total weight of the asenapine-containing matrix layer.

23. The method according to any of embodiments 20-22, wherein the transdermal therapeutic system is administered once a day.

24. The method according to any of embodiments 20-23, wherein the transdermal therapeutic system provides an asenapine $AUC_{0-24}$ of from about 5 to about 100 (ng/ml)*h.

25. The method according to embodiment 24, wherein the transdermal therapeutic system provides an asenapine $AUC_{0-24}$ of from about 10 to about 90 (ng/ml)*h.

26. A method of treating bipolar disorder in a patient in need thereof, the method comprising administering to the patient a transdermal therapeutic system comprising an asenapine-containing self-adhesive layer structure, said self-adhesive layer structure comprising:

a) a backing layer; and b) an asenapine-containing matrix layer comprising:

(i) a therapeutically effective amount of asenapine free base; and (ii) at least 50% by weight of a polymer selected from the group consisting of polysiloxanes and polyisobutylenes.

27. The method according to embodiment 26, wherein the bipolar disorder is acute manic bipolar disorder.

28. The method according to embodiment 26, wherein the bipolar disorder is mixed episodes of bipolar disorder.

29. The method according to any of embodiments 26-28, wherein the asenapine-containing matrix layer further comprises at least one excipient selected from the group consisting of crystallization inhibitors, solubilizers, fillers, substances for skincare, pH regulators, preservatives, tackifiers, softeners, stabilizers, and permeation enhancers.

30. The method according to any of embodiments 26-28, wherein the asenapine-containing matrix layer comprises:

(i) 2 to 7% by weight of asenapine in the form of the free base;

(ii) 85 to 98% by weight of a polysiloxane;

(iii) 0.01 to 1.0% by weight of tocopherol; and (iv) 0.5 to 10% by weight of polyvinylpyrrolidone.

31. The method according to any of embodiments 26-29, wherein the transdermal therapeutic system is administered once a day.

32. The method according to any of embodiments 26-30, wherein the transdermal therapeutic system provides an asenapine $AUC_{0-24}$ of from about 5 to about 100 (ng/ml)*h.

33. The method according to any of embodiment 32, wherein the transdermal therapeutic system provides an asenapine $AUC_{0-24}$ of from about 10 to about 90 (ng/ml)*h.

The invention claimed is:

1. A transdermal therapeutic system for the transdermal administration of asenapine comprising a self-adhesive layer structure comprising a therapeutically effective amount of asenapine, said self-adhesive layer structure comprising:

A) a backing layer;

B) an asenapine-containing layer comprising:

a) asenapine free base; and b) a polymer selected from the group consisting of polysiloxanes and polyisobutylenes in an amount of more than 50% by weight based on the total weight of the asenapine-containing layer; and C) optionally an additional skin contact layer;

wherein the asenapine-containing layer comprises a crystallization inhibitor in an amount of 0.5 to 10% by weight based on the total weight of the asenapine-containing layer.

2. The transdermal therapeutic system according to claim 1, wherein the asenapine-containing layer is an asenapine-containing matrix layer; and/or wherein the area weight of the asenapine-containing layer ranges from 50 to 120 g/m², or from 70 to 100 g/m².

3. The transdermal therapeutic system according to claim 1, wherein the amount of asenapine in the asenapine-containing layer ranges from 1 to 10%, or from 2 to 7% by weight based on the total weight of the asenapine-containing layer, and/or wherein the amount of asenapine contained in the transdermal therapeutic system ranges from 3 to 21 mg, or from 3.5 to 14 mg.

4. The transdermal therapeutic system according to claim 1, wherein the amount of the polymer ranges from 55 to 98%, from 70 to 98%, from 80 to 98% or from 92 to 98% by weight based on the total weight of the asenapine-containing layer.

5. The transdermal therapeutic system according to claim 1, wherein the polymer is a polysiloxane.

6. The transdermal therapeutic system according to claim 1, wherein the asenapine-containing layer comprises a stabilizer in an amount of 0.01 to 1.0% by weight based on the total weight of the asenapine-containing layer.

7. The transdermal therapeutic system according to claim 1, wherein the asenapine-containing layer is an asenapine-containing matrix layer comprising:

a) asenapine free base in an amount of 2 to 7% by weight based on the total weight of the asenapine-containing matrix layer;

b) polysiloxane in an amount of from 92 to 98% by weight based on the total weight of the asenapine-containing layer;
c) a stabilizer in an amount of from 0.01 to 1.0% by weight based on the total weight of the asenapine-containing layer; and/or
d) a crystallization inhibitor in an amount of from 0.5 to 10% by weight based on the total weight of the asenapine-containing layer.

8. The transdermal therapeutic system according to claim 1, wherein the asenapine-containing layer is an asenapine-containing matrix layer comprising:
   a) asenapine free base in an amount of 2 to 7% by weight based on the total weight of the asenapine-containing matrix layer;
   b) a polysiloxane in an amount of 92 to 98% by weight based on the total weight of the asenapine-containing matrix layer;
   c) tocopherol in an amount of 0.01 to 1.0% by weight based on the total weight of the asenapine-containing matrix layer; and/or
   d) polyvinylpyrrolidone in an amount of 0.5 to 10% by weight based on the total weight of the asenapine-containing matrix layer;
wherein the matrix layer has an area weight ranging from 70 to 100 g/m$^2$.

9. A transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      a) asenapine in an amount of from 2 to 7% by weight based on the total weight of the asenapine-containing layer;
      b) at least one silicone polymer in an amount of from 85 to 98% by weight based on the total weight of the asenapine-containing layer;
      c) a stabilizer in an amount of from 0.01 to 1.0% by weight based on the total weight of the asenapine-containing layer; and
      d) a crystallization inhibitor in an amount of from 0.5 to 10% by weight based on the total weight of the asenapine-containing layer; and
   C) optionally an additional skin contact layer.

10. The transdermal therapeutic system according to claim 9, wherein the stabilizer is tocopherol and the crystallization inhibitor is polyvinylpyrrolidone.

11. The transdermal therapeutic system according to claim 9, wherein the asenapine-containing layer has an area weight ranging from 50 to 120 g/m$^2$, or from 70 to 100 g/m$^2$.

12. The transdermal therapeutic system according to claim 9, wherein the silicone polymer is obtainable by polycondensation of silanol endblocked polydimethylsiloxane with a silicate resin, wherein the ratio of the silanol endblocked polydimethylsiloxane to the silicate resin is in the range of from 70:30 to 50:50, and wherein a residual functionality of the at least one silicone polymer is capped with trimethylsiloxy groups.

13. A transdermal therapeutic system for the transdermal administration of asenapine comprising a self-adhesive layer structure comprising a therapeutically effective amount of asenapine, said self-adhesive layer structure comprising:
   A) a backing layer;
   B) an asenapine-containing layer comprising:
      a) asenapine in an amount of from 2 to 15% by weight based on the total weight of the asenapine-containing layer;
      b) at least one polyisobutylene in an amount of from 70 to 98% by weight based on the total weight of the asenapine-containing layer; and
      c) a hydrophilic polymer in an amount of from 1 to 20% by weight based on the total weight of the asenapine-containing layer; and
   C) optionally an additional skin contact layer.

14. The transdermal therapeutic system according to claim 13, wherein the self-adhesive layer structure comprises
   A) a backing layer;
   B) an asenapine-containing layer, which is an asenapine-containing matrix layer, comprising:
      a) asenapine in an amount of from 4 to 12% by weight based on the total weight of the asenapine-containing layer;
      b) at least one polyisobutylene in an amount of from 70 to 90% by weight based on the total weight of the asenapine-containing layer; and
      c) polyvinylpyrrolidone in an amount of from 1 to 20% by weight based on the total weight of the asenapine-containing layer; and
   C) optionally an additional skin contact layer.

15. The transdermal therapeutic system according to claim 13, wherein the asenapine-containing layer has an area weight ranging from 40 to 250 g/m$^2$, or from 40 to 125 g/m$^2$.

16. The transdermal therapeutic system according to claim 13, wherein the at least one polyisobutylene is a combination of a low molecular weight polyisobutylene and a high molecular weight polyisobutylene in a ratio of from 99:1 to 50:50, and wherein the low molecular weight polyisobutylene has a viscosity average molecular weight of from 38,000 to 42,000 g/mol and/or a weight average molecular weight of from 34,000 to 40,000 g/mol, and wherein the high molecular weight polyisobutylene has a viscosity average molecular weight of from 1,100,000 to 1,120,000 g/mol and/or a weight average molecular weight of from 1,540,000 to 1,560,000 g/mol.

17. A method of treating bipolar disorder and/or schizophrenia in a patient in need thereof, comprising administering to the patient the transdermal therapeutic system according to claim 1.

18. The method according to claim 17, wherein the transdermal therapeutic system is applied to the skin of the patient for a dosing interval of from 20 to 30 hours.

19. A process for manufacturing an asenapine-containing layer for use in a transdermal therapeutic system according to claim 1 comprising:
   A) combining
      a) asenapine;
      b) a polymer selected from the group consisting of polysiloxanes and polyisobutylenes in an amount of more than 50% by weight based on the total weight of the asenapine-containing layer; and
      c) a crystallization inhibitor in an amount of 0.5 to 10% by weight based on the total weight of the asenapine-containing layer;
   to obtain a coating composition;
   B) coating the coating composition onto the backing layer, a release liner, or any intermediate liner; and
   C) drying the coated coating composition to form the asenapine-containing layer.

* * * * *